(12) United States Patent
Koberstein et al.

(10) Patent No.: US 8,263,192 B2
(45) Date of Patent: Sep. 11, 2012

(54) METHODS FOR MODIFYING SURFACES

(75) Inventors: Jeffrey T. Koberstein, Storrs, CT (US);
Peng Wang, Ann Arbor, MI (US); Feng Pan, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1503 days.

(21) Appl. No.: 11/454,652

(22) Filed: Jun. 16, 2006

(65) Prior Publication Data
US 2007/0134420 A1 Jun. 14, 2007

Related U.S. Application Data

(63) Continuation of application No. PCT/US2004/042363, filed on Dec. 16, 2004.

(60) Provisional application No. 60/530,809, filed on Dec. 18, 2003.

(51) Int. Cl.
*B05D 5/00* (2006.01)
*B05D 3/06* (2006.01)
*C08J 7/18* (2006.01)

(52) U.S. Cl. ..... 427/553; 427/2.13; 427/333; 427/407.1

(58) Field of Classification Search ............ 427/2.1, 427/2.13, 551–553, 271, 272, 282, 333, 407.1
See application file for complete search history.

(56) References Cited

U.S. PATENT DOCUMENTS

| | | | |
|---|---|---|---|
| 4,539,061 A | 9/1985 | Sagiv et al. | |
| 5,466,557 A | 11/1995 | Haley et al. | |
| 5,514,501 A * | 5/1996 | Tarlov | 430/5 |
| 5,580,697 A * | 12/1996 | Keana et al. | 430/296 |
| 5,840,467 A | 11/1998 | Kitatani et al. | |
| 5,852,127 A | 12/1998 | Belfort et al. | |
| 5,885,753 A | 3/1999 | Crooks et al. | |
| 6,180,288 B1 | 1/2001 | Everhart et al. | |
| 6,200,646 B1 | 3/2001 | Neckers et al. | |
| 6,306,584 B1 * | 10/2001 | Bamdad | 435/6.12 |
| 6,413,587 B1 | 7/2002 | Hawker et al. | |
| 6,423,465 B1 | 7/2002 | Hawker et al. | |
| 6,492,096 B1 | 12/2002 | Liu et al. | |
| 6,586,158 B2 | 7/2003 | Dobisz et al. | |
| 6,630,404 B1 | 10/2003 | Babcock | |
| 6,682,988 B1 | 1/2004 | Babcock | |
| 6,881,836 B2 * | 4/2005 | McGall et al. | 536/25.3 |
| 2002/0107159 A1 | 8/2002 | DeSimone et al. | |
| 2003/0091752 A1 | 5/2003 | Nealey et al. | |
| 2004/0253536 A1 | 12/2004 | Park et al. | |
| 2006/0165912 A1 | 7/2006 | Koberstein et al. | |

OTHER PUBLICATIONS

Patchornik et al., "Photosensitive Protecting Groups," J. Am. Chem Soc., 92:21, Oct. 21, 1970, pp. 6333-6335.*
Kiederowski, "Light-Directed Parallel Synthesis of Up to 250 000 Different Oligopeptides and Oligonucleotides," Angew. Chem. Int. Ed. Engl. 30 (1991) No. 7, pp. 822-823.*
Dulcey et al., "Deep UV Photochemistry of Chemisorbed Monolayers: Patterned Coplanar Molecular Assemblies," Science 252:551-554 (1991).*
Stenger et al., "Coplanar Molecular Assemblies of Amino- and Perfluorinated Alkylsilanes: Characterization of Geometric Definition of Mammalian Cell Adhesion and Growth," J. Am. Chem. Soc. 1992, 114, 8435-8442.*
Rozsnyai et al., "Photolithographic Immobilization of Biopolymers on Solid Supports," Angew. Chem. Int. Ed. Engl. 31 (1992) No. 6, pp. 759-761.*
Frisbie et al., "Secondary ion mass spectrometry for characterizing photopatterned, self-assembled monolayers on gold," J. Vac. Sci. Technol. A 11(4), Jul./Aug. 1993, pp. 2368-2372.*
Delamarche et al., "Immobilization of Antibodies on a Photoactive Self-Assembled Monolayer on Gold," Langmuir 1996, 12, 1997-2006.*
Dulcey et al., "Photochemistry and Patterning of Self-Assembled Monolayer Films Containing Aromatic Hydrocarbon Functional Groups," Langmuir 1996, 12, 1638-1650.*
International Search Report mailed on Jul. 12, 2005 for International Application No. PCT/US04/42363 filed Dec. 16, 2004.
Written Opinion mailed on Jul. 12, 2005 for International Application No. PCT/US04/42363 filed Dec. 16, 2004.
Abbott, Nicholas L. et al. "Manipulation of the Wettability of Surfaces on the 0.1—to 1-Micrometer Scale Through Micromachining and Molecular Self-Assembly." Science, 257:1380-1382. (Sep. 4, 1992).
Abuchowski, Abraham et al. "Cancer Therapy with Chemically Modified Enzymes. I. Antitumor Properties of Polyethylene Glycol-Asparaginase Conjugates." Cancer Biochem. Biophys., 7:175-186. (1984).
Aizenberg, Joanna et al. "Control of crystal nucleation by patterned self-assembled monolayers." Nature, 398:495-498. (1999).
Aizenberg, Joanna et al. "Patterned Colloidal Deposition Controlled by Electrostatic and Capillary Forces." Physical Review Letters, 84(13):2997-3000. (Mar. 27, 2000).
Akritopoulou-Zanze, Irini et al. "Configuration of Heptopyranoside and Heptofuranoside Side Chains: 2-Anthroate, a Powerful Chromophore for Exciton Coupled CD." Chirality, 9:699-712. (1997).
Anastasiadis, S. H. et al. "Neutron Reflectivity Studies of the Surface-Induced Ordering of Diblock Copolymer Films." Physical Review Letters, 62(16):1852-1855. (Apr. 17, 1989).
Andrade J.D. *Surface interfacial aspects of biomedical polymer* v1 1985, Plenum Press, New York, Chpt. 5, P178.

(Continued)

*Primary Examiner* — William Phillip Fletcher, III
(74) *Attorney, Agent, or Firm* — Wilmer Cutler Pickering Hale and Dorr, LLP

(57) ABSTRACT

The invention is directed to methods for coating monolayer films of surface-active polymers onto substrates of arbitrary shape, and molecular-based methods and processes to control the chemical and physical nature of surfaces and interfaces. The invention is also directed to methods for modifying a surface of a monolayer comprising a) coating a monolayer on a substrate, wherein the monolayer is formed by self-assembly of end-surfactant molecules, thereby positioning a photoactive functional group at the air-monolayer interface; and b) exposing the monolayer to radiation, wherein each organic group of the monolayer contains a first functionality that is not converted to a second functionality upon exposure to acid.

15 Claims, 62 Drawing Sheets

OTHER PUBLICATIONS

Andrade, Joseph D. "X-ray Photoelectron Spectroscopy (XPS)." Surface and Interfacial Aspects of Biomedical Polymers, vol. 1, pp. 105-195. (1985).

Avrameas, Stratis. "Natural Antibodies." Academic Press, pp. 1134-1135. (1991).

Bain, Colin D. et al. "Formation of Monolayer Films by the Spontaneous Assembly of Organic Thiols from Solution onto Gold." J. Am. Chem. Soc., 111:321-335. (1989).

Bain, Collin D. and George M. Whitesides. "Attenuation Lengths of Photoelectrons in Hydrocarbon Films." J. Phys. Chem., 93:1670-1673. (1989).

Bates, Frank S. and Glenn H. Fredrickson. "Block Copolymer Thermodynamics: Theory and Experiment." Annu. Rev. Phys. Chem., 41:525-557. (1990).

Beamson, G. and D. Briggs. High Resolution XPS of Organic Polymers. The Scienta ESCA300 Database, Chichester, England. (1992).

Berek, Claudia and Cesar Milstein. "The Dynamic Nature of the Antibody Repertoire." Immunological Reviews, No. 105, pp. 5-26. (1988).

Bernard, Andre et al. "Printing Patterns of Proteins." Langmuir, 14(9):2225-2229. (Apr. 28, 1998).

Bhatia, Qamardeep S. et al. "Preferential Surface Adsorption in Miscible Blends of Polystyrene and Poly (vinyl methyl ether)." Macromolecules, 21:2166-2175. (1988).

Blawas et al., "Protein patterning," , Biomaterials, 19, 595-609 (1998).

Bourg, Marie-Caroline et al. "Gold-Sulfur Bonding in 2D and 3D Self-Assembled Monolayers: XPS Characterization." J. Phys. Chem., 104:6562-6567. (2000).

Bow, Sing-Tze. Pattern Recognition and Image Preprocessing, Marcel Dekker, Inc., New York. (1992).

Brandrup, J. et al. Polymer Handbook, John Wiley & Sons, Inc., New York. (1999).

Briggs, David and Graham Beamson. "XPS Studies of the Oxygen 1s and 2s Levels in a Wide Range of Functional Polymers." Anal. Chem., 65:1517-1523. (1993).

Brown, Glenn H. Techniques of Chemistry, vol. III, Photochromism, Wiley-Interscience, New York. (1971).

Brown, Gregory et al. "Layering Phase Separation of Densely Grafted Diblock Copolymers." Macromolecules, 28:7817-7821. (1995).

Brown, Michael P. S. et al. "Knowledge-based analysis of microarray gene expression data by using support vector machines." PNAS, 97(1):262-267. (Jan. 4, 2000).

Burges, Christopher J. C. "A Tutorial on Support Vector Machines for Pattern Recognition." Data Mining and Knowledge Discovery, 2:121-167. (1998).

Burmeister, Frank et al. "Colloid Monolayers as Versatile Lithographic Masks." Langmuir, 13:2983-2987. (1997).

Cameron, James F. et al. "Photogeneration of Amines from α-Keto Carbamates: Photochemical Studies." J. Am. Chem. Soc., 118:12925-12937. (1996).

Castner, David G. et al. "X-ray Photoelectron Spectroscopy Sulfur 2p Study of Organic Thiol and Disulfide Binding Interactions with Gold Surfaces." Langmuir, 12:5083-5086. (1996).

Clackson, Tim et al. "Making antibody fragments using phage display libraries." Nature, 352:624-628. (Aug. 15, 1991).

Coessens, Veerle et al. "Functionalization of polymers prepared by ATRP using radical addition reactions." Macromol. Rapid Commun., 21:103-109. (2000).

Corrie, John E. T. and David R. Trentham. "Caged Nucleotides and Neurotransmitters." Bioorganic Photochemistry, 2:243-305. (1993).

Coulon, G. et al. "Surface-Induced Orientation of Symmetric, Diblock Copolymers: A Secondary Ion Mass Spectrometry Study." Macromolecules, 22:2581-2589. (1989).

Dannenberger, O. et al. "An orientation analysis of differently endgroup-funtionalised alkanethiols adsorbed on Au substrates." Thin Sold Films, 307:183-191. (1997).

Day, William H. E. and Herbert Edelsbrunner. "Efficient Algorithms for Agglomerative Hierarchical Clustering Methods." Journal of Classification 1:7-24. (1984).

Delamarche, E. et al. "Immobiliation of Antibodies on a Photoactive Self-Assembled Monolayer on Gold." Langmuir, 12:1997-2006. (1996).

Deng, Chao et al. "Normalization of cDNA Microarray Data By using Neural Networks." Proceedings of the 2002 International Joint Conference on Neural Networks. May 12-17, 2002.

DeSimone, J. M. et al. "Dispersion Polymerizations in Supercritical Carbon Dioxide." Science, 265:356-359. (Jul. 15, 1994).

Dewez, J. L. et al. "Adhesion of mammalian cells to polymer surfaces: from physical chemistry of surfaces to selective adhesion on definied patterns." Biomaterials, 19:1441-1445. (1998).

Deye, Jerry F. et al. "Nile Red as a Solvatochromic Dye for Measuring Solvent Strength in Normal Liquids and Mixtures of Normal Liquids with Supercritical and Near Critical Fluids." Anal. Chem., 62:615-622. (1990).

Dhirani, Al-Amin et al. "Self-Assembly of Conjugated Molecular Rods: A High-Resolution STM Study." J. Am. Chem. Soc., 118:3319-3320. (1996).

Dorman, Gyorgy and Glenn D. Prestwich. "Using photolabile ligands in drug discovery and development." Tibtech, 18:64-77. (Feb. 2000).

Dorman, Gyorgy and Glenn D. Prestwick. "Benzophenone Photophores in Biochemistry." Biochemistry, 33(19):5661-5673. (May 17, 1994).

Douvas et al., "Biocompatible photolithographic process for the patterning of biomolecules," Biosensors & Bioeletronics, vol. 17, pp. 269-278 (2002).

Duda, Richard O. et al. Pattern Classification. John Wiley & Sons, Inc., New York. (2001).

Dulcey, Charles S. et al. "Photochemistry and Patterning of Self-Assembled Monolayer Films Containing Aromatic Hydrocarbon Functional Groups." Langmuir, 12:1638-1650. (1996).

Eynde, X. Vanden and P. Bertrand. "Combined XPS and ToF-SIMS Study of Miscible Polymer Blend Surfaces: Polystyrene/Poly(2,6-dimethyl-1,4-phenylene oxide) (PS/PDMPO)." Surface and Interface Analysis, 27:157-164. (1999).

Ezzell, John W. et al. "Identification of *Bacillus anthracis* by Using Monoclonal Antibody to Cell Wall Galactose-N-Acetylglucosamine Polysaccharide." Journal of Clinical Microbiology, 28(2):223-231. (Feb. 1990).

Fadley, Charles S. "Solid State-and Surface-Analysis by Means of Angular-Dependent X-Ray Photoelectron Spectroscopy." Progress in Solid State Chemistry, 11:265-343. (1976).

Flounders, A. W. et al. "Patterning of immobilized antibody layers via photolithography and oxygen plasma exposure." Biosensors & Bioelectronics, 12(6):447-456. (1997).

Fodor, Stephen P. A. et al. "Light-Directed, Spatially Addressable Parallel Chemical Synthesis." Science, 251:767-773. (Feb. 15, 1991).

Forster, T. "Delocalized Excitation and Excitation Transfer." Section III. B Light and Organic Crystals, Academic Press, London, pp. 93-137. (1965).

Frechet, Jean M. J. et al. "Photogenerated Base in Resist and Imaging Materials: Design of Functional Polymers Susceptible to Base Catalyzed Decarboxylation." Chem. Mater., 9:2887-2893. (1997).

Frey, S. et al. "Structure of Thioaromatic Self-Assembled Monolayers on Gold and Silver." Langmuir, 17:2408-2415. (2001).

Fried, Roland et al. "Online Pattern Recognition in Intensive Care Medicine." AMIA, pp. 184-188. (2001).

Furey, Terrence S. et al. "Support vector machine classification and validation of cancer tissue samples using microarray expression data." Bioinformatics, 16(10):906-914. (2000).

Gabor, Allen H. et al. "Lithographic Properties of Poly(tert-butyle methacrylate)-Based Block and Random Coopolymer Resists Designed for 193 nm Wavelength Exposure Tools." Chem. Mater., 8:2282-2290. (1996).

Geyer, W. et al. "Electron-induced crosslinking of aromatic self-assembled monolayers: Negative resists for nanolothography." Applied Physics Letters, 75(16):2401-2403. (2001).

Gillen et al., "Molecular imaging secondary Ion Mass Spectrometry for the Characterization of patterned Self-assembled monolayers on Silver and Gold," Anal. Chem., 66, 2170-2174 (1994).

Gillen, Greg et al. "Patterning of self-assembled alkanethiol monolayers on silver by microfocus ion and electron beam bombardment." Appl. Phys. Lett., 65(5):534-536. (Aug. 1, 1994).

Gillmor, S. D. et al. "Hydrophilic/Hydrophobic Patterned Surfaces as Templates for DNA Arrays." Langmuir, 16:7223-7228. (2000).

Guiomar, A. Jorge et al. "Use of Mixed Self-Assembled Monolayers in a Study of the Effect of the Microenvironment on Immobilized Glucose Oxidase." Langmuir, 15:1198-1207. (1999).

Han, Sang Woo et al. "Azobenzene-Incorporated Alkanethiol Monolayer Film on Au(111): Reflection-Absorption Infrared Spectroscopy and Atomic Force Microscopy Study." Langmuir, 15:1579-1583. (1999).

Harrison, Kristi L. et al. "Effect of Surfactants on the Interfacial Tension between Supercritical Carbon Dioxide and Polyethylene Glycol." Langmuir, 12:2637-2644. (1996).

Hata, K. et al. "Selective adsorption and patterning of Si nanoparticles fabricated by laser ablation on functionalized self-assembled monolayer." Applied Physics Letters, 79(5):692-694. (Jul. 30, 2001).

Hayashi, Sadao et al. "Imaging by Polystyrene Latex Particles." Journal of Colloid and Interface Science, 144(2):538-547. (Jul. 2, 1991).

Hengsakul, Manchumas and Anthony E. G. Cass. "Protein Patterning with a Photoactivatable Derivative of Biotin." Bioconjugate Chem., 7:249-254. (1996).

Henkee, Chris S. et al. "The effect of surface constraints on the ordering of block copolymer domains." Journal of Materials Science, 23:1685-1694. (1988).

Hern, Diane L. and Jeffrey A. Hubbell. "Incorporation of adhesion peptides into nonadhesive hydrogels useful for tissue resurfacing." J. Biomed. Mater. Res, 39:266-276. (1998).

Heyer, Laurie et al. DIMACS Workshop on Analysis of Gene Expression Data. Oct. 24-26, 2001. Rutgers University, Piscataway, NJ.

Himmelhaus, M. and H. Takei. "Self-assembly of polystyrene nano particles into patterns of random-close-packed monolayers via chemically induced adsorption." Phys. Chem. Chem. Phys., 4:496-506. (2002).

Holden, D. A. et al. "Studies of Singlet Energy Transfer in Polymers by Time-Resolved Fluorescence Spectroscopy." Annals New York Academy of Science, 366:11-23. (1981).

Holmes-Farley, Stephen Randall et al. "Acid-Base Behavior of Carboxylic Acid Groups Covalently Attached at the Surface of Polyethylene: The Usefullness of Contact Angle in Following the Ionization of Surface Functionality." Langmuir, 1:725-740. (1985).

Hu, S. et al., "Photochemical Reactions of Alkyl Phenylglyoxylates," J. Org. Chem. 1996, 61, 6407-6415.

Huang et al., "Photooxidation of Thiols in Sefl-Assembled monolayers on GOld," . J. Am. Chem. Soc., 115, 3342-3343 (1993).

Huang, Jingyu et al. "Photopatterning of Self-Assembled Alkanethiolate Monolayers on Gold: A Simple Monolayer Photoresist Utilizing Adueous Chemistry." Langmuir, 10:626-628. (1994).

Huang, Shao-Chie et al. "Site-Specific Immobilization of Monoclonal Antibodies Using Spacer-Mediated Antibody Attachment." Langmuir, 12:4292-4298. (1996).

Husemann et al., "Manipulation of surface properties by patterning of cvalently bound polymer brushes," J. Am. Chem. Soc., vol. 122, pp. 1844-1845 (2000).

Husemann, Marc et al. "Surface-Initiated Polymerization for Amplification of Self-Assembled Monolayers Patterned by microcontact Printing." Angew. Chem. Int. Ed., 38(5):647-649. (1999).

Hyun, Jinho and Ashutosh Chilkoti. "Micropatterning Biological Molecules on a Polymer Surface Using Elastomeric Microwells." J. Am. Chem. Soc., 123:6943-6944. (2001).

Hyun, Jinho et al. "Micropatterns of a Cell-Adhesive Peptide on an Amphiphilic Comb Polymer Film." Langmuir, 18:2975-2979. (2002).

Hyun, Jinho et al. "Microstamping on an Activated Polymer Surface: Patterning Biotin and Streptavidin onto Common Polymeric Biomaterials." Langmuir, 17:6358-6367. (2001).

Infelta, P. P. et al. "Luminescence Decay of Hydrophobic Molecules Solubilized in Aqueous Micellar Systems. A Kinetic Model." The Journal of Physical Chemistry, 79(2):190-195. (1974).

International Search Report issued for International Application No. PCT/US2003/04214.

Ishida, Takao and Nami Choi. "High-Resolution X-ray Photoelectron Spectra of Organosulfur Monolayers on Au(111): S(2p) Spectral Dependence on Molecular Species." Langmuir, 15:6799-6806. (1999).

Ito H.; Ueda M.; Ebina M.; "Copolymer Approach to Design of sensitive Deep-UV Resist Systems with High Thermal Stability and Dry Etch Resistance," Polymers in Microlithography: Materials and processes; ACS Symposium Series 412; American Chemical Society: Washington, DC, 1989; p57.

Jain, Anil K. et al. "Statistical Pattern Recognition: A Review." IEEE Transactions on Pattern Analysis and Machine Intelligence, 22(1):4-37. (Jan. 2000).

Jain, L. C. et al. Intelligent Biometric Techniques in Fingerprint and Face Recognition. CRC Press, Boca Raton, FL. (1999).

Jolliffe, I. T. Principal Component Analysis, Springer-Verlag, New York. (1986).

Jonas, Ulrich et al. "Colloidal assemblies on patterned silane layers." PNAS, 99(8):5034-5039. (Apr. 16, 2002).

Ju, Jingyue et al. "Cassette labeling for facile construction of energy transfer fluorescent primers." Nucleic Acids Research, 24(6):1144-1148. (1996).

Ju, Jingyue et al. "Energy transfer primers: A new fluorescence labeling paradigm for DNA sequencing and analysis." Nature Medicine, 2(2): 246-249. (Feb. 1996).

Ju, Jingyue et al. "Fluorescence energy transfer dye-labeled primers for DNA sequencing and analysis." Proc. Natl. Acad. Sci., 92:4347-4351. (May 1995).

Karim, A. et al. "Phase separation of ultrathin polymer-blend films on patterned substrates." 57(6):R6273-R6276. (Jun. 1998).

Kaski, Samuel. "Dimensionality Reduction by Random Mapping: Fast Similarity Computation for Clustering." IEEE, pp. 413-418. (1998).

Kim, Chi S. et al. "Preparation of anthracene-labelled poly(methyl methacrylate) via atom transfer radical polymerization." Macromol. Rapid Comun., 19:191-196. (1998).

Kim, Seungchan et al. "General nonlinear framework for the analysis of gene interaction via multivariate expression arrays." Journal of Biomedical Optics, 5 4):411-424. (Oct. 2000).

Kim, Sunwook and K. P. Johnston. "Effects of Supercritical Solvents on the Rates of Homogeneous Chemical Reactions." Supercritical Fluids Chemical Engineering Principles and Applications, American Chemical Society, Symposium Series, Washington, DC, 329:42-55. (1987).

Koberstein et al., "Creating smart polymer surfaces with selective adhesion properties," J. Adhesion, vol. 66, pp. 229-249 (1998).

Koberstein, J. T. "Polymer Surfaces and Interfaces." MRS Bulletin, pp. 16-18. (Jan. 1996).

Kohler, G. and C. Milstein. "Continuous cultures of fused cells secreting antibody of predefined specificity." Nature, 256:495-497. (Aug. 7, 1975).

Kokkoli, Efrosini et al. "Surface Pattern Recognition by a Colloidal Particle." Langmuir, 17:369-376. (2001).

Kondo, Toshihiro et al. "Determination of Thickness of a Self-Assembled Monolayers of Dodecanethiol on Au(111) by Angle-Resolved X-ray Photoelectron Spectroscopy." Langmuir, 14:5656-5658. (1998).

Kumar et al., "Patterned condensation figures as optical diffraction gratings," Science, 263 60-62 (1994).

Kumar, Amit and George M. Whitesides. "Features of gold having micrometer to centimeter dimensions can be formed through a combination of stamping with an elastomeric stamp and an alkanethiol 'ink' followed by chemical etching." Appl. Phys. Lett., 63(14):2002-2004. (Oct. 1993).

Kumar, Amit et al. "Patterned Self-Assembled Monolayers and Meso-Scale Phenomena." Acc. Chem. Res., 28:219-226. (1995).

Kumar, Amit et al. "Patterning Self-Assembled Monolayers: Applications in Materials Science." Langmuir, 10:1498-1511. (1994).

Laibinis, Paul E. et al. "Attenuation of Photoelectrons in Monolayers of n-Alkanethiols Adsorbed on Copper, Silver and Gold." J. Phys. Chem., 95:7017-7021. (1991).

Lee, Milton L. and Karin E. Markides. Analytical Supercritical Fluid Chromatography and Extraction. Chromatography Conferences, Inc., Provo, Utah. (1990).

Lepilleur, Carole and Eric J. Beckman. "Dispersion Polymerization of Methyl Methacrylate in Supercritical CO2." Macromolecules, 30:745-756. (1997).

Li, Jintong et al. "Dynamics of Pressure-Induced Phase Separation in Polymer Solutions. The Dependence of the Demixing Pressures on the Rate of Pressure Quench in Solutions of Poly(dimethylsiloxane) in Supercritical Carbon Dioxide." Ind. Eng. Chem. Res., 38:4486-4490. (1999).

Li, Xinsong et al. "An observation on excimer formation in pyrenyl-labelled polystyrene: concentrated solution and solvent-plasticized film." Polymer International, 48:630-632. (1999).

Lopez, Gabriel P. et al. "Imaging of Features on Surfaces by Condensation Figures." Science, 260:647-649. (Apr. 30, 1993).

Luo, Laibin and Adi Eisenberg. "Thermodynamic Stabilization Mechanism of Block Copolymer Vesicles." J. Am. Chem. Soc., 123:1012-1013. (2001).

MacBeath, Gavin and Stuart L. Schreiber. "Printing Proteins as Microarrays for High- Throughput Function Determination." Science, 289:1760-1763. (Sep. 8, 2000).

MacDonald, Scott A. et al. "Chemical Amplification in High-Resolution Imaging Systems." Accounts of Chemical Research, 27(6):151-158. (Jun. 1994).

Mansky, P. et al. "Ordered Diblock Copolymer Films on Random Copolymer Brushes." Macromolecules, 30:6810-6813. (1997).

Marks, James D. et al. "By-passing Immunization Human Antibodies from V-gene Libraries Displayed on Phage." J. Mol. Biol., 222:581-597. (1991).

McGhee, Jerry R. "Regulation of IgA Synthesis and Immune Response by T Cells and Interleukins." Journal of Clinical Immunology, 9(3):175-199. (1989).

McHugh, M. A. et al. "Cosolvent effect alkyl acrylates on the phase behaviour of poly(alkyl acrylates)—supercritical CO2 mixtures." Polymer, 39(24):6049-6052. (1998).

McHugh, Mark A. and Val J. Kurkonis. Supercritical Fluid Extraction. Butterworth Publishers, Stoneham, MA. (1986).

Mooney, J. F. et al. "Patterning of functional antibodies and other proteins by photolithography of silane monolayers." Proc. Natl. Acad. Sci., 93:12287-12291. (Oct. 1996).

Morawetz, Herbert. "Fluorescence Studies of Ionomers." Acc. Chem. Res., 27:174-178. (1994).

Nadler, Morton and Eric P. Smith. Pattern Recognition Engineering, John Wiley & sons Inc., New York. (1993).

Nakagawa, Masaru et al. "Photopatterning and Visualization of Adsorbed Monolayers of Bis(1-benzyl-4-pyrdinio)ethylene Moieties." Adv. Mater., 12(6):403-407. (2000).

Neff, J. A. et al. "A novel method for surface modification to promote cell attachment to hydrophobic substrates." J. Biomed. Mater. Res., 40:511-519. (1998).

Nelson, Kjell E. et al. "Surface Characterization of Mixed Self-Assembled Monolayers Designed for Streptavidin Immobilization." Langmuir, 17:2807-2816. (2001).

Ni, Shaoru et al. "Energy Transfer Studies of the Boundary Layer Interphase in Polystyrene-Poly(methyl methacrylate) Block Copolymer Films." Macromolecules, 27:5742-5750. (1994).

Nicolau, Dan V. et al. "Actin Motion on Microlithographically Functionalized Myosin Surfaces and Tracks." Biophysical Journal, 77:1126-1134. (Aug. 1999).

Nicolau, Dan V. et al. "Micron-Sized Protein Patterning on Diazonaphthoquinone/Novolak Think Polymeric Films." Langmuir, 14:1927-1936. (1998).

Nicolau, Dan V. et al. "Protein patterning via radiation-assisted surface functionalization of conventional microlithographic materials." Colloids and Surfaces A: 155:51-62. (1999).

Nilsson, Kurt and Klaus Mosbach. "Immobilization of Enzymes and Affinity Ligands to Various Hydroxyl Group Carrying Supports using Highly reactive Sulfonyl Chlorides." Biochemical and Biophysical Research Communications, 102(1):449-457. (Sep. 16, 1981).

O'Neill, M. L. et al. "Emulsion Stabilization and Flocculation in CO2. 1. Turbidimetry and Tensiometry." Macromolecules, 30:5050-5059. (1997).

O'Neill, M. L. et al. "Solubility of Homopolymers and Copolymers in Carbon Dioxide." Ind. Eng. Chem. Res., 37:3067-3079. (1998).

Palacin, Serge et al. "Patterning with Magnetic Materials at the Micron Scale." Chem. Mater., 8:1316-1325. (1996).

Pappas, S. Peter. "Photogeneration of Acid: Part 6—A Review of Basic principles for Resist Imaging Applications." Journal of Imaging Technology, 11:146-157. (1985).

Paul et al., "Synthesis of Ultrathin films of Polyacrylonitril by photoinitiated polymerization from Self-assembled monolayers on Gold," Langmuir, vol. 18(23), pp. 8719-8723 (2002).

Peppas, Nicholas A. and Robert Langer. "New Challenges in Biomaterials." Science, 263:1715-1720. (Mar. 25, 1994).

Peters, Richard D. et al. "Using Self-Assembled Monolayers Exposed to X-rays to Control the Wetting Behavior of Thin Films of Diblock Copolymers." Langmuir, 16:4625-4631. (2000).

Petosa, Carlo et al. "Crystal structure of the anthrax toxin protective antigen." Nature, 385:833-838. (Feb. 27, 1997).

Phaneuf, Matthew D. et al. "Covalent linkage of recombinant hirudin to poly(ethylene terephthalate) (Dacron): creation of a novel antithrombin surface." Biomaterials, 18:755-765. (1997).

Pillai, V. N. Rajasekharan. "Photolytic Deprotection and Activation of Functional Groups." Organic Photochemistry, pp. 225-323. (1987).

Popat, Kris and Kenneth Zeger. "Robust quantization of Memoryless Sources Using Dispersive FIR Filters." IEEE Transactions on Communications, 40(11):1670-1674. (Nov. 1992).

Prescher et al., "Synthesis of liquid-crystalline poly(meth) acrylates with 4-trifluoromethoxy-azobenzene mesogenic side-groups," J. Fluorine Chem. vol. 74, pp. 185-189 (1995).

Prestwich, Glenn D. et al. "Benzophenone Photoprobes for Phosphoinositides, Peptides and Drugs." Photochemistry and Photobiology, 65(2):222-234. (1997).

Qin, Dong et al. "Fabrication of Ordered Two-Dimensional Arrays of Micro- and Nanoparticles Using Patterned Self-Assembled Monolayers as Templates." Adv. Mater., 11(17):1433-1437. (1999).

Rabek J.F.; Photochemistry and Photophysics, Chapter 4., pp. 137-191, 1990, CRC Press. Inc.

Ramaswamy, Sridhar et al. "Multiclass cancer diagnosis using tumor gene expression signatures." PNAS, 98(26):15149-15154. (Dec. 18, 2001).

Ramdas, Latha et al. "Sources of nonlinearity in cDNA microarray expression measurements." Genome Biology, 2(11):47.1-47.7. (Oct. 18, 2001).

Rasmussen, James R. et al. "Introduction, Modification, and Characterization of Functional Groups on the Surface of Low-Density Polyethylene Film." Journal of the American Chemical Society, 99(14):4736-4745. (Jul. 6, 1977).

Reichmanis, Elsa et al. "Copolymer Approach to Design of Sensitive Deep-UV Resist Systems with High Thermal Stability and Dry Etch Resistance." Polymers in Microlithography Materials and Processes, American Chemical Society, Washington, DC. (1989).

Reiter G., "Dewetting of thin polymer films," Phys. Rev. Lett. vol. 68, pp. 75-78 (1992).

Revzin, Alexander et al. "Fabrication of Poly(ethylene glycol) Hydrogel Microstructures Using Photolithography." Langmuir, 17:5440-5447. (2001).

Rice, Jeanette K. et al. "State-Dependent Solvation of Pyrene in Supercritical CO2." J. Am. Chem. Soc., 117:5832-5839. (1995).

Rindfleisch, Frank et al. "Solubility of Polymers and Copolymers in Supercritical CO2." J. Phys. Chem., 100:15581-15587. (1996).

Robb, R.A., "Biomedical Imaging, Visualization, and Analysis," entire book, 2000.

Rosenblum, B. B. et al. "New dye-labeled terminators for improved DNA sequencing patterns." Nucleic Acids Research, 25(22):4500-4504. (1997).

Ross, Claudia B. et al. "Scanning Probe Lithography. 1. Scanning Tunneling Microscope Induced Lithography of Self-Assembled n-Alkanethiol Monolayer Resists." Langmuir, 9:632-636. (1993).

Roxlo, C. B. et al. "Edge Surfaces in Lithographically Textured Molybdenum Disulfide." Science Reports, 235:1629-1631. (Mar. 27, 1987).

Sabatani, Eyal et al. "Thioaromatic Monolayers on Gold: A New Family of Self-Assembling Monolayers." Langmuir, 9:2974-2981. (1993).

Sabongi, Gebran J. Chemical Triggering. Reactions of Potential Utility in Industrial Processes. Plenum Press, New York. (1987).

Saminathan et al., "Synthesis and characterization of main-chain liquid-crystalline polymers containing a p-phenyleneazo group," Macromolecules, 26 (25), pp. 7103-7105 (1993).

Saxon, Eliana and Carolyn r. Bertozzi. "Cell Surface Engineering by a Modified Staudinger Reaction." Science, 287:2007-2010. (Mar. 17, 2000).

Schwarz, Alexandra et al. "Micropatterning of Biomolecules on Polymer Substrates." Langmuir, 14:5526-5531. (1998).

Seok, Chaok et al. "Polymer blends near patterned surfaces." Journal of Chemical Physics, 112(14):6452-6460. (Apr. 8, 2000).

Shin, Yongsoon et al. "Supercritical processing of functionalized size selective microporous materials." Microporous and Mesoporous Materials, 37:49-56. (2000).

Siewierski, L. M. et al. "Photoresponsive Monolayers Containing In-Chain Azobenzene." Langmuir, 12:5838-5844. (1996).

Singhvi, Rahul et al. "Engineering Cell Shape and Function." Science, 264:695-698. (Apr. 29, 1994).

Smith, Roger M. Supercritical Fluid Chromatography, Royal Society of Chemistry, London. (1988).

Snapper, Clifford M. Cytokine Regulation of Humoral Immunity Basic and Clinical Aspects, John Wiley & Sons, Chichester, England. (1996).

Stiller et al., "Self-assembled monolayers of novel azobenzenes for optically induced switching," Material Science and Engineering, 1999, 8-9, 385-389.

Stryer, Lubert. "Fluorescence Energy Transfer as a Spectroscopic Ruler." Ann. Rev. Biochem., 47:819-846. (1978).

Su, Andrew I. et al. "Molecular Classification of Human Carcinomas by Use of Gene Expression Signatures." Cancer Research, 61:7388-7393. (Oct. 15, 2001).

Sun, Yukie and Gilbert C. Walker. "Two-Dimensional Self-Assembly of Latex Particles in Wetting Films on Patterned Polymer Surfaces." J. Phys. Chem. B, 106:2217-2223. (2002).

Sundberg, Steven A. et al. "Spatially-Addressable Immobilization of Macromolecules on Solid Supports." J. Am. Chem. Soc., 117:12050-12057. (1995).

Tachiya, Masaanori. "Application of a Generating Function to Reaction Kinetics in Micelles. Kinetics of quenching of Luminescent Probes in Micelles." Chemical Physics Letters, 33(2):289-292. (Jun. 1, 1975).

Tamada, K. et al. "Molecular Packing of Semifluorinated Alkanethiol Self-Assembled Monolayers on Gold: Influence of Alkyl Spacer Length." Langmuir, 17:1913-1921. (2001).

Tan, John L. et al. "Microcontact Printing of Proteins on Mixed Self-Assembled Monolayers." Langmuir, 18:519-523. (2002).

Tao, Yu-Tai et al. "Structure Evolution of Aromatic-Derivatized Thiol Monolayers on Evaporated Gold." Langmuir, 13:4018-4023. (1997).

Tarlov, Michael J. et al. "UV Photopatterning of Alkanethiolate Monolayers Self-Assembled on Gold and Silver." J. Am. Chem. Soc., 115:5305-5306. (1993).

Taylor, Larry. Supercritical Fluid Extraction. John Wiley & Sons, Inc. New York. (1996).

Tiberio, R. C. et al. "Self-assembled monolayer electron beam resist on GaAs." Appl. Phys. Lett., 62(5):476-478. (1993).

Tong, Anthony K. and Jingyue Ju. "Single nucleotide polymorphism detection by combinatorial fluorescence energy transfer tags and biotinylated dideoxynucleotides." Nucleic Acids Research, 30(5):1-7. (2002).

Tong, Anthony K. et al. "Combinatorial fluorescence energy transfer tags for multiplex biological assays." Nature Biotechnology, 19:756-759. (Aug. 2001).

Tong, Anthony K. et al. "Triple Fluorescence Energy Transfer in Covalently Trichromophore-Labeled DNA." J. Am. Chem. Soc., 123:12923-12924. (2001).

Tong, Jiang-Dong et al. "Synthesis of Meth(acrylate) Diblock Copolymers Bearing a Fluorescent Dye at the Junction Using a Hydroxyl-Protected Initiator and the Combination of Anionic Polymerization and Controlled Radical Polymerization." Macromolecules, 34:696-705. (2001).

Torkelson, John M. et al. "Polystyrene-Methylcyclohexane Solutions Undergoing Phase Separation: A Study by Bluorescence Spectroscopy." Macromolecules, 17:1505-1512. (1984).

Tour, James M. et al. "Self-Assembled Monolayers and Multilayers of Conjugated Thiols, $\alpha,\omega$-Dithiols, and Thioacetyl-Containing Adsorbates. Understanding Attachments between Potential Molecular Wires and Gold Surfaces." J. Am. Chem. Soc., 117:9529-9534. (1995).

Tsao, Mei-Wei et al. "Formation and Characterization of Self-Assembled Films of Thiol-Derivatized Poly(Dimethylsiloxane) on Gold." Macromolecules, 30:5913-5919. (1997).

Tseng, George C. et al. "Issues in cDNA microarray analysis: quality filtering, channel normalization, models of variations and assessment of gene effects." Nucleic Acids Research, 29(12):2549-2557. (2001).

Ulman, Abraham and James F. Elman. "X-Ray Photoelectron Spectroscopy of Organic Thin Films." Chapter 11, pp. 213-225. (1995).

Vacheethasanee, Katanchalee and Roger E. Marchant. "Surfactant polymers designed to suppress bacterial (Staphylococcus epidermidis) adhesion on biomaterials." J. Biomed. Mater. Res., 50:302-312. (2000).

van Blaaderen, Alfons and Pierre Wiltzius. "Growing Large, Well-Oriented Colloidal Crystals." Adv. Mater., 9(10):833-835. (1997).

van Blaaderen, Alfons et al. "Template-directed colloidal crystallization." Nature, 385:321-324. (Jan. 1997).

Vapnik, Vladimir N. "An Overview of Statistical Learning Theory." IEEE Transactions on Neural Networks, 10(5):988-999. (Sep. 1999).

Vapnik, Vladimir N. Statistical Learning Theory, John Wiley & Sons, Inc., New York. (1998).

Vapnik, Vladimir N. The Nature of Statistical Learning Theory. Springer-Verlag, New York. (1995).

Vavasour, J. D. and M. D. Whitmore. "Self-Consistent Mean Field Theory of the Microphases of Diblock Copolymers." Macromolecules, 25:5477-5486. (1992).

Wallraff, G. M. and W. D. Hinsberg. "Lithographic Imaging Techniques for the Formation of Nanoscopic Features." Chem. Rev., 99:1801-1821. (1999).

Wang et al., "Carbohydrate, microarrays for the recognition of cross-reactive molecular markers of microbes and host cells," Nature Biotechnology, vol. 20, pp. 275-281 (2002).

Wang, Denong and Elvin A. Kabat. "Antibodies, Specificity." Academic Press, London, pp. 148-154. (1998).

Wang, Denong and Elvin A. Kabat. "Carbohydrate Antigens (Polysaccharides)." Structure of Antigens, 3:247-277. (1996).

Wang, Denong et al. "The Repertoire of Antibodies to a Single Antigenic Determinant." Molecular Immunology, 28(12):1387-1397. (1991).

Wang, Denong et al. "Two Families of Monoclonal Antibodies to $\alpha(1-6)$Dextran, $V_H19.1.2$ and $V_H9.14.7$, Show Distinct Patterns of $J_\kappa$ and $J_H$ Minigene Usage and Amino Acid Substitutions in $CDRD_1$." The Journal of Immunology, 145(9):3002-3010. (1990).

Wang, Jason T. L. et al. Pattern Discovery in Biomolecular Data, Oxford University Press, New York. (1999).

Watkins, James J. et al. "Chemical Fluid Deposition: Reactive Deposition of Platinum Metal from Carbon Dioxide Solution." Chem. Mater., 11:213-215. (1999).

Werwa, E. et al. "Synthesis and processing of silicon nanocrystallites using a pulsed laser ablation supersonic expansion method." Appl. Phys. Lett., 64(14):1821-1823. (Apr. 1994).

Wolf et al., "End-Group-dominated molecular order in Self-assembled monolayers," J. Phys. Chem., 99, 7102-7107 (1995).

Wu, Albert M. The Molecular Immunology of Complex Carbohydrates—2, Kluwer Academic/Plenum Publishers, New York. (2001).

Wybourne, M. N. et al. "Creation of biomolecule arrays by electrostatic immobilization on electron-beam-irradiated polystyrene thin films." Nanotechnology 7:302-305. (1996).

Wyman, "The Cis-Trans isomerization of conjugated compounds," C. Chem. Rev., vol. 55, 625-657. (1955).

Wyman, George M. "The CIS-Trans Isomerization of Conjugated Compounds." Quartermaster Research and Development Center, Natick, MA. (Feb. 14, 1955).

Yang, Zhihao et al. "Protein Interactions with Poly(ethylene glycol) Self-Assembled Monolayers on Glass Substrates: Diffusion and Adsorption." Langmuir, 15:8405-8411. (1999).

Yang, Zhongping and Ashutosh Chilkoti. "Microstamping of a Biological Ligand onto an Activated Polymer Surface." Adv. Mater., 12(6):413-417. (2000).

Yang, Zhongping et al. "Molecular Imaging of a Micropatterned Biological Ligand on an Activated Polymer Surface." Langmuir, 16:7482-7492. (2000).

Yang, Zhongping et al. "Preparation and Characterization of Mixed Monolayer Assemblies Composed of Thiol Analogues of Cholesterol and Fatty Acid." Langmuir, 13:3210-3218. (1997).

Ye, Bihui H. et al. "The BCL-6 proto-oncogene controls germinal-centre formation and Th2-type inflammation." Nature Genetics, 16:161-170. (Jun. 16, 1997).

Yin, Yadong et al. "Template-Assisted Self-Assembly: A Practical Route to Complex Aggregates of Monodispersed Colloids with Well-Definied Sizes, Shapes, and Structures." J. Am. Chem. Soc., 123:8718-8729. (2001).

Zagrobelny, JoAnn et al. "Steady-State and Time-Resolved Fluorescence Investigations of Pyrene Excimer Formation in supercritical CO2." J. Am. Chem. Soc., 114:5249-5257. (1992).

Zemanian, Thomas S. et al. "Deposition of Self-Assembled Monolayers in Mesoporous Silica from from Supercritical Fluids." Langmuir, 17:8172-8177. (2001).

Zhang, Huiqi et al. "Synthesis of Anthracene End-Capped Poly(methyl methacrylate)s via Atom Transfer Radical Polymerization and Its Kinetic Analyses." Macromolecules, 35:2261-2267. (2002).

Zhang, Lifeng and Adi Eisenberg. "Multiple Morphologies of 'Crew-Cut' Aggregates of Polystyrene-b-poly(acrylic acid) Block Copolymers." Science, 268:1728-1731. (Jun. 23, 1995).

Zhang, Qi et al. "Determination of locations of sulfur, amide-nitrogen and azo-nitrogen in self-assembled monolayers of alkanethiols and azobenzenethiols on Au(111) and GaAs (100) by angle-resolved X-ray photoelectron spectroscopy." Surface Science, 440:142-150. (1999).

Zhao, Bin et al. "Nanopattern Formation from Tethered PS-b-PMMA Brushes upon Treatment with Selective Solvents." J. Am. Chem. Soc., 122:2407-2408. (2000).

Zhao, Xiao Kang et al. "Size quantization in Semiconductor Particulate Films." J. Phys. Chem., 95:3716-3723. (1991).

Zharnikov, M. et al. "Modification of Alkanethiolate Monolayers by Low Energy Electron Irradiation: Dependence on the Substrate Material and on the Length and Isotoopic Composition of the Alkyl Chains." Langmuir, 16:2697-2705. (2000).

* cited by examiner

100μm

FT-IR
Thin Film of free
molecule on KBr

Contact Angle: 85 ±1°

Grazing Angle
FT-IR of SAM

| Polymer | SAM | Features | |
|---|---|---|---|
| Poly(epichlorohydrin) PECH | Benzophenone | -Vapor Sensor<br>-Cl peak can be easily seen by XPS |  |
| Poly(vinylalcohol) PVA | Phthalimide | -OH peak should be discernable in IR spectrum<br>-Hydrophilicity should affect contact angle |  |
| Poly(styrene) PS | Phthalimide | -Hydrophobicity should affect contact angle<br>-Compare results with benzophenone SAM |  |

Benzophenone SAM PECH Thin Film Irradiated

|  | C | Cl | Si | O |
|---|---|---|---|---|
| % Conc. | 41.85 | 7.81 | 14.96 | 35.38 |

No Monolayer PECH Thin Film Irradiated

|  | C | Cl | Si | O |
|---|---|---|---|---|
| % Conc. | 24.93 | 1.19 | 23.15 | 50.72 |

Benzophenone SAM PECH Thin Film No Irradiation

|  | C | Cl | Si | O |
|---|---|---|---|---|
| % Conc. | 18.23 | 0 | 26.28 | 55.49 |

```
ESCA Survey   26 Feb 04   Area: 1    45 degrees Acq Time: 2.50 min
File: gc0226047  bnzph PECH no irradiation 45
Scale:  6.633 kc/s   Offset:  0.000 kc/s   Pass E: 93.900 eV   Aperture: 4  Al  350 W
```

Poly(vinyl)alcohol PVA

Radius of Gyration: 1.5 nm
MW: 30,000-50,000

$$R_g^2 = R^2_{end\text{-}to\text{-}end}/6$$

Ellipsometry and Water Contact Angle Data

| Sample | Total Thickness after Wash(nm) | Final Film Thickness - Initial (nm) | Contact Angle after Wash | Contact Angle without film |
|---|---|---|---|---|
| PVA No Monolayer 254 nm | 1.89 ±.09 | -.2±.1 | 37±1 | 38 ±2° |
| PVA Phthalimide SAM 254 nm | 5.3±.2 | 2.7±.3 | 47.3±.4 | 65±1° |
| PVA Phthalimide SAM Dark | 3.4±.1 | .8±.1 | 56 ±2° | 65±1° |

$R_g$ (Radius of Gyration): 1.3 nm $$R_g = .0275(M_w)^{1/2}$$

2.1 K PS

| Sample | Thickness After Wash (nm) | Final Thickness – Initial (nm) | Contact Angle After Wash | Contact Angle without Film |
|---|---|---|---|---|
| Phthalimide SAM 254 nm | 4.15 ±.03 | 1.57 ±.05 | 77 ±3° | 65 ±1° |
| Bare Substrate 254 nm | 2.81 ±.03 | 0.77 ±.04 | 64 ±2° | 38 ±2° |
| Phthalimide SAM Dark | 2.99 ±.02 | 0.42 ±.03 | 58 ±2° | 65 ±1° |
| Bare Substrate Dark | 2.90 ±.09 | 0.9 ±.1 | 37 ±1° | 38 ±2° |

Figure 39

PS Thin Films
- 20 min. at 146°
- 120 min. at 146°

Length of bar is 100 um

PS 800-5000 MW
2 hours 140-160°

PECH 700 MW
3 hours 160°

12.2 nm PS Film on Phthalimide SAM

SAM 3 hours

Glass 3 hours

SAM 24 hours

Glass 24 hours

Bnzphn SAM 350 nm

Bnzph SAM Dark

Untreated

Pre-light

Post-light

Post-wash

Benzophenone SAM

Pre-light

Post-light

Post-wash

Nitrocellulose

Pre-light

Post-light

NA

Post-wash

Contact Angles
Nitrocellulose: 65±2°
Nitrocellulose/
Benzophenone: 86±1°

Spin-coat onto Nitrocellulose

Graft Carbohydrate site for radical addition

Nitrocellulose

Pre-light

Post-light

Post-light_print

Benzophenone -Nitrocellulose

Pre-light

Post-light

Post-light_print

METHODS FOR MODIFYING SURFACES

This application is a continuation of International Patent Application No. PCT/US2004/042363, filed Dec. 16, 2004, which claims the benefit of provisional application U.S. Ser. No. 60/530,809, filed Dec. 18, 2003, which are both hereby incorporated by reference into the subject application in their entireties.

The government may have certain rights in the present invention pursuant to a grant from the U.S. Army Research Laboratory and the U.S. Army Research Office, Grant No. DAAD19-00-10104, and a grant from the Materials Research Science and Engineering Centers program of the National Science Foundation, Award No. DMR-0213574.

Throughout this application, various publications are referenced. The disclosures of these publications in their entireties are hereby incorporated by reference into this application in order to more fully describe the state of the art as known to those skilled therein as of the date of the invention described and claimed herein.

The disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

It is often highly desirable to design and control the structure and properties of surfaces and interfaces without affecting a material's bulk properties. Surface properties of interest include wettability, adhesion, tack, friction and wear, hardness, and gloss. The ability to modify and control chemical functionality on surfaces in a precise manner is desirable because a change in surface chemistry inevitably changes the surface free energy and other material properties of interest, such as adhesion and wettability, which are important in coatings and paints. It also allows the possibility of further surface derivatization of external ligands, for example, by selectively attaching molecules of interest to polymer surfaces, which is an important way to build molecular assemblies with confined positions for complex nanoscale and biomolecular devices. The task of modifying surfaces and interfaces to control such properties is daunting because many surface characteristics are related to the nature and physical structure on the molecular level. Ideally, surface modification strategies involve few or no reagents, require only ambient conditions in normal atmosphere, are universal for a variety of substrate materials, and do not necessitate elaborate external processing operations. Most current surface modification strategies do not meet these conditions.

A variety of surface modification techniques are known. Few current techniques for surface modification, however, allow for specific chemical and structural control at molecular dimensions. In addition, many methods under development for surface modification are not readily suited to industrial application and scale up.

One common way to achieve modification of polymer surfaces is by plasma, X-ray, UV, laser, ion beam and e-beam etching, or corona discharge, which involves bombarding the surface with highly excited atomic, molecular, ionic, electronic, or free radical species to form reactive groups on an inert surface. Oxidative treatments, such as corona discharge, oxygen plasma, or UV/ozone are indiscriminate and kinetic in nature, rendering the control of modification depth of surface chemistry difficult. These treatments are often unstable, and involve reorganization at the surface shortly after processing. Chemical treatment methods for surface modification often require harsh and hazardous reagents, and the depth of modification can usually be confined to the surface only by regulating the exposure time. Further, these techniques usually require expensive equipment and sophisticated process controls. These techniques also involve safety hazards including electric shock, UV exposure, and laser exposure. Further, these surface modification techniques result in non-homogenous surfaces that have multiple surface functional groups, which reduces their selectivity for subsequent derivatization. These techniques are increasingly unacceptable from an environmental and safety perspective. These techniques also have difficulties in modifying the surface uniformly and reproducibly.

Some emerging materials applications require molecular level control of the spatial distribution of chemical functionalities comprising the surface. Several patterning techniques have been demonstrated, including nanografting, microstamping, and photolithography. However, several limitations are associated with each of these methods. Nanografting requires the use of atomic force and scanning tunneling microscopes and is a slow technique requiring physical contact with each spatial location in the pattern. Microstamping requires fabrication of both a positive and negative mold and involves subsequent alignment of the stamps and a mechanical step to transfer physisorbed monolayers to the surface of the substrate. Photolithography involves the use of a patterned photo-mask containing opaque and translucent regions to choreograph regiospecific photochemical changes within a photoresist. The resolution of the patterned area is limited only by the wavelength of the light, but existing techniques suffer from the usual requirement of a development step to create the pattern.

Accordingly, there is a great need for inexpensive, convenient, and accessible methods of selectively modifying surfaces. There is also a need for molecular-based methods and processes that can be used to design and control the chemical and physical nature of surfaces and interfaces. It is desirable to modify functional groups in a homogenous way. It is also desirable to control the spatial distributions of surface functional groups.

SUMMARY OF THE INVENTION

The present invention is directed to methods for modifying a substrate having a surface comprising coating a macromolecular surfactant comprising a modifiable functional group on to the surface of the substrate, wherein the modifiable functional group assembles to the air-coating interface, thereby modifying the surface of the substrate; wherein if the substrate comprises a first polymer and the macromolecular surfactant comprises a second polymer having a modifiable functional group, then the group is not modifiable by an acid to functionally modify the surface of the substrate.

The invention is also directed to methods for modifying a substrate having a surface comprising coating a macromolecular surfactant comprising a modifiable functional group to the surface of the substrate from a supercritical fluid, wherein the macromolecular surfactant is soluble in the supercritical fluid, wherein the modifiable functional group assembles to the air-coating interface, thereby modifying the surface of the substrate.

The present invention is further directed to methods for modifying a surface, comprising coating the surface with a copolymer comprising at least two units, each unit having a different surface tension than the other, wherein at least one unit has a surface tension lower than that of the surface, wherein the unit of the copolymer having the lowest surface tension assembles to the air-coating interface and comprises a photoactive functional group; and exposing the coating to radiation, thereby modifying the surface, wherein the surface comprises metal, metalloid, polymer, organic material, ceramic, metal oxide, metalloid oxide, or a combination thereof, provided that the surface does not comprise glass.

The invention is also directed to methods for modifying a surface of a monolayer, comprising coating a monolayer on a substrate; wherein the monolayer is formed by self-assembly of end-functionalized surfactant molecules, thereby positioning a photoactive functional group at the air-monolayer interface; and exposing the monolayer to radiation, thereby modifying the surface of the monolayer, provided that if the monolayer is a self-assembled monolayer of organic groups, then each organic group contains a first functionality that is not capable of being converted to a second functionality by exposure to an acid to functionally modify the surface.

The invention is also directed to devices having a surface modified by the methods of the present invention.

The invention is directed to macromolecular surfactants comprising at least two units each having a different surface tension, wherein the unit having the lowest surface tension comprises a modifiable functional group, and wherein the modifiable functional group comprises a protected functional group, that is not an acid-reactive functional group; a photoactive functional group; a base-reactive functional group; an electrochemically reactive functional group; a functional group that is reactive with electricity; or a combination thereof.

BRIEF DESCRIPTION OF THE DRAWINGS

FIG. 39 shows features of a PS-tethered phthalimide surface.

DETAILED DESCRIPTION OF THE INVENTION

Figure 1:
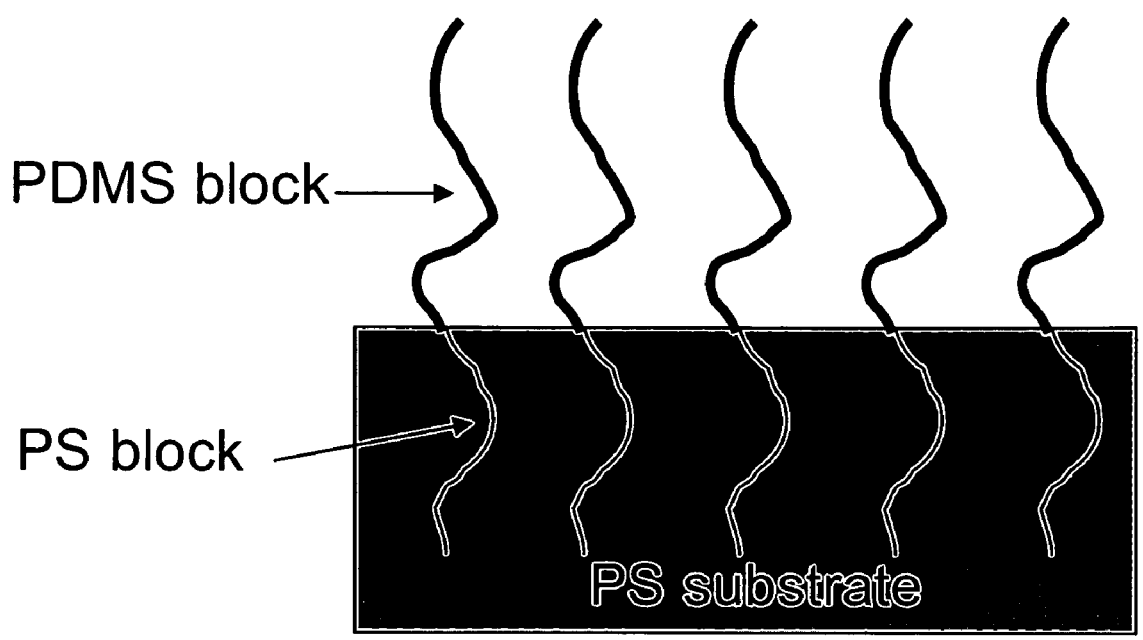
FIG. 1 depicts the creation of a release surface on a polystyrene substrate with a poly(styrene-b-dimethylsiloxane) block copolymer.

The present invention is directed to methods for coating monolayer films of surface-active polymers onto substrates of arbitrary shape. The present invention also provides molecular-based methods and processes that can be used to control the chemical and physical nature of surfaces and interfaces. The present invention is directed to methods for modifying functional groups in a homogenous way and controlling the spatial distributions of surface functional groups.

The present invention is directed to methods for modifying a substrate having a surface comprising coating a macromolecular surfactant comprising a modifiable functional group onto the surface of the substrate, wherein the modifiable functional group assembles to the air-coating interface, thereby modifying the surface of the substrate, wherein if the substrate comprises a first polymer and the macromolecular surfactant comprises a second polymer having a modifiable functional group, then the group is not modifiable by an acid to functionally modify the surface of the substrate. In another embodiment, the method further comprises modifying the functional group. In one embodiment, the macromolecular surfactant comprises a polymer, a copolymer, a block copolymer, a graft copolymer, a statistical copolymer, a hydrogel, a self-assembled monolayer, or a combination thereof. In another embodiment, the macromolecular surfactant comprises a polymer.

In one embodiment, the modifiable functional group comprises a protected functional group, a photoactive functional group, a base-reactive functional group, an electrochemically reactive functional group, a functional group that is reactive with electricity, or a combination thereof.

In one embodiment, the substrate surface is modified at a specific location. In another embodiment, the modifying produces a surface pattern. In one embodiment, the modifying comprises exposing the surface to radiation. In another embodiment, the exposing is performed in the presence of a photomask. In another embodiment, the radiation comprises a pattern of scanning lines.

In one embodiment, the method further comprises imaging the surface pattern. In another embodiment, the imaging comprises fluorescence imaging, water condensation imaging, scanning electron microscopy imaging, x-ray photoelectron spectroscopy imaging, or a combination thereof.

In one embodiment, the method further comprises reacting the modified functional group with a ligand. In another embodiment, the ligand comprises a biological molecule, a peptide, a protein, a carbohydrate, DNA, an enzyme, an aptamer, a third polymer, a colloidal particle, a nanoparticle, or a combination thereof.

In one embodiment, the concentration of polymer is sufficient to provide a saturated monolayer coating. In another embodiment, the concentration of polymer is sufficient to provide a sub-monolayer coating.

In one embodiment, the polymer is a copolymer. In another embodiment, the copolymer comprises at least two units each having a different surface tension than the other, wherein the unit of the copolymer having the lowest surface tension assembles to the air-coating interface and comprises the modifiable functional group. In another embodiment, the unit of the copolymer having the highest surface tension has favorable interaction energy with the substrate. In another embodiment, the heat of mixing between the substrate and copolymer is negligible or negative.

In one embodiment, the copolymer comprises a photoactive block copolymer. In another embodiment, the photoactive block copolymer comprises polystyrene. In another embodiment, the photoactive block copolymer comprises poly(t-butyl acrylate). In another embodiment, the photoactive block copolymer comprises polystyrene and poly(t-butyl acrylate).

In one embodiment, the coating comprises a monolayer. In another embodiment, the monolayer is surface active. In one embodiment, the coating comprises a sub-monolayer.

In one embodiment, the coating comprises self-assembly, spin-coating, adsorption, coating from a supercritical fluid, or a combination thereof.

The present invention is also directed to methods for modifying a substrate having a surface comprising coating a macromolecular surfactant comprising a modifiable functional group onto the surface of the substrate from a supercritical fluid, wherein the macromolecular surfactant is soluble in the supercritical fluid, and wherein the modifiable functional group assembles to the air-coating interface, thereby modifying the surface of the substrate.

In another embodiment, the macromolecular surfactant comprising the modified functional group is not soluble in the supercritical fluid. In one embodiment, the macromolecular surfactant comprises a polymer. In another embodiment, the supercritical fluid comprises carbon dioxide.

In one embodiment, the coating occurs in a chamber under pressure. In another embodiment, the coating occurs without using a volatile organic compound. In another embodiment, the chamber is under pressure above about 8 MPa. In another embodiment, the chamber is under pressure in the range from about 8 MPa to about 16 MPa. In one embodiment, the chamber is under pressure above about 25 MPa. In another embodiment, the chamber is under pressure in the range from about 25 MPa to about 46 MPa. In another embodiment, the pressure is maintained at about a constant pressure. In one embodiment, the pressure is maintained at about a constant pressure for at least about thirty minutes.

In one embodiment, the temperature of the chamber is in the range of about room temperature to about 50° C. In another embodiment, the temperature of the chamber is maintained at about a constant temperature.

In one embodiment, the substrate comprises glass, metal, polymer, a self-assembled monolayer, or a combination thereof. In another embodiment, the surface of the substrate is not flat. In another embodiment, the surface of the substrate comprises a pore. In one embodiment, the surface of the substrate comprises an internal pore. In another embodiment, the substrate comprises a tube having an inner surface.

The invention is directed to a device formed by modifying a substrate having a surface comprising coating a macromolecular surfactant comprising a modifiable functional group onto the surface of the substrate, wherein the modifiable functional group assembles to the air-coating interface, thereby modifying the surface of the substrate, wherein if the substrate comprises a first polymer and the macromolecular surfactant comprises a second polymer having a modifiable functional group, then the group is not modifiable by an acid to functionally modify the surface of the substrate. In another embodiment, the device comprises a coverslip, a glass slide, a semiconductor chip, a plate, a microarray sensor, a biomedical device, a catheter, a blood bag, a dialysis machine, an artificial heart, a biological sensor, a circuit, a substrate for electroplating, an implant, a nanoparticle, or a combination thereof.

The invention is also directed to a device formed by modifying a substrate having a surface comprising coating a macromolecular surfactant comprising a modifiable functional group onto the surface of the substrate with a supercritical fluid, wherein the macromolecular surfactant is soluble in the supercritical fluid, and wherein the modifiable functional group assembles to the air-coating interface, thereby modifying the surface of the substrate. In another embodiment, the device comprises a coverslip, a glass slide, a semiconductor chip, a plate, a microarray sensor, a biomedical device, a catheter, a blood bag, a dialysis machine, an artificial heart, a biological sensor, a circuit, a substrate for electroplating, an implant, a nanoparticle, or a combination thereof.

The invention is also directed to methods for modifying a surface, comprising coating the surface with a copolymer comprising at least two units each having a different surface tension than the other, wherein at least one unit has a surface tension lower than that of the surface, wherein the unit of the copolymer having the lowest surface tension assembles to the air-coating interface and comprises a photoactive functional group, and exposing the coating to radiation, thereby modifying the surface, wherein the surface comprises metal, metalloid, polymer, organic material, ceramic, metal oxide, metalloid oxide, or a combination thereof, provided that the surface does not comprise glass.

In one embodiment, the coating step comprises annealing.

In one embodiment, the exposing comprises photodeprotection. In another embodiment, modifying the surface produces a surface pattern. In one embodiment, the exposing is carried out in the presence of a photomask. In another embodiment, the radiation comprises a pattern of scanning lines.

In one embodiment, the method further comprises imaging the surface pattern. In another embodiment, the imaging comprises fluorescence imaging, water condensation imagining, scanning electron microscopy imaging, x-ray photoelectron spectroscopy imaging, or a combination thereof.

In one embodiment, the photoactive functional group comprises an ester group. In another embodiment, the ester group comprises a t-butyl ester group.

In one embodiment, the copolymer comprises a block copolymer. In another embodiment, the copolymer comprises a photoactive block copolymer. In another embodiment, the copolymer comprises poly(t-butyl acrylate).

In one embodiment, the copolymer comprises a diblock copolymer. In another embodiment, the diblock copolymer comprises poly(t-butyl acrylate) and polystyrene.

In one embodiment, the metal comprises silicon, gold or a combination thereof.

In one embodiment, the radiation comprises ultraviolet radiation. In another embodiment, the radiation comprises deep ultraviolet radiation.

In one embodiment, the coating further comprises a photoacid generator of formula I, formula II, or a combination thereof:

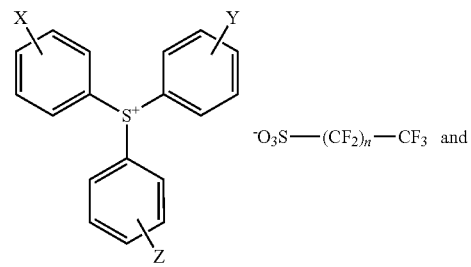

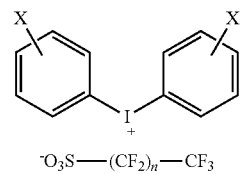

wherein X is selected from the group consisting of —H, —O(CH$_2$)$_7$CH$_3$, -tButyl, —OCH$_3$, —CF$_3$, and thienyl;

Y is selected from the group consisting of —H, -tButyl, —OCH$_3$, 1-naphthyl, 2-napthyl, and thienyl;

Z is selected from the group consisting of —H, -tButyl, —OCH$_3$, 1-naphthyl, and 2-naphthyl; and n is 0-10.

In one embodiment, the method further comprises immobilizing on the copolymer coating a biomolecule. In another embodiment, the biomolecule comprises a protein. In another embodiment, the protein comprises biotin, biotin ethylenediamine, bovine serum albumin, and fluorescein-5 isothiocyanate tagged bovine serum albumin, or a combination thereof.

In another embodiment is provided a device formed by modifying a surface, comprising coating the surface with a copolymer comprising at least two units each having a different surface tension than the other, wherein at least one unit has a surface tension lower than that of the surface, wherein the unit of the copolymer having the lowest surface tension assembles to the air-coating interface and comprises a photoactive functional group, and exposing the coating to radiation, thereby modifying the surface, wherein the surface comprises metal, metalloid, polymer, organic material, ceramic, metal oxide, metalloid oxide, or a combination thereof, provided that the surface does not comprise glass. In another embodiment, the device comprises a coverslip, a semiconductor chip, a plate, a microarray sensor, a biomedical device, a catheter, a blood bag, a dialysis machine, an artificial heart, a biological sensor, circuit, a substrate for electroplating, an implant, a nanoparticle, or a combination thereof.

The present invention is further directed to methods for modifying a surface of a monolayer, comprising coating a monolayer on a substrate, wherein the monolayer is formed by self-assembly of end-functionalized surfactant molecules, thereby positioning a photoactive functional group at the air-monolayer interface, and exposing the monolayer to radiation, thereby modifying the surface of the monolayer, provided that if the monolayer is a self-assembled monolayer of organic groups, then each organic group contains a first functionality that is not capable of being converted to a second functionality by exposure to an acid to functionally modify the surface.

In one embodiment, the self-assembled monolayer comprises a benzophenone moiety, a phthalimide moiety, a benzoin moiety, a photogenerated aldehyde moiety, or a combination thereof.

In one embodiment, the exposing comprises photodeprotection. In another embodiment, the exposing produces a surface pattern. In one embodiment, the exposing is performed in the presence of a photomask. In another embodiment, the radiation comprises a pattern of scanning lines. In one embodiment, the radiation comprises ultraviolet radiation. In another embodiment, the radiation comprises deep ultraviolet radiation.

In one embodiment, the method further comprises imaging the surface pattern. In another embodiment, the imaging comprises fluorescence imaging, water condensation imaging, scanning electron microscopy imaging, x-ray photoelectron spectroscopy imaging, or a combination thereof.

In one embodiment, the method further comprises coating on the monolayer a macromolecular surfactant. In another embodiment, the macromolecular surfactant is a polymer. In one embodiment, the macromolecular surfactant is a hydrophilic polymer. In another embodiment, the macromolecular surfactant is a hydrophobic polymer.

In another embodiment, the self-assembled monolayer comprises a coating on a substrate surface. In another embodiment, the substrate surface comprises glass, metal, metalloid, ceramic or a combination thereof. In one embodiment, the substrate surface comprises silicon, gold or a combination thereof.

In one embodiment, the method further comprises immobilizing on the self-assembled monolayer surface a carbohydrate, a peptide, a protein, DNA, an enzyme, an aptamer, a colloidal particle, nanoparticle, metal oxide, or a combination thereof. In another embodiment, the colloidal particle comprises a polystyrene colloidal particle.

In one embodiment, the method further comprises oxidizing the monolayer.

In another embodiment is provided a device formed by modifying a surface of a monolayer, comprising coating a monolayer on a substrate, wherein the monolayer is formed by self-assembly of end-functionalized surfactant molecules, thereby positioning a photoactive functional group at the air-monolayer interface, and exposing the monolayer to radiation, thereby modifying the surface of the monolayer, provided that if the monolayer is a self-assembled monolayer of organic groups, then each organic group contains a first functionality that is not capable of being converted to a second functionality by exposure to an acid to functionally modify the surface. In another embodiment, the device comprises a coverslip, a glass slide, a semiconductor chip, a plate, a microarray sensor, a biomedical device, a catheter, a blood bag, a dialysis machine, an artificial heart, a biological sensor, a circuit, a substrate for electroplating, an implant, a nanoparticle or a combination thereof.

The present invention is directed to macromolecular surfactants comprising at least two units each having a different surface tension, wherein the unit having the lowest surface tension comprises a modifiable functional group, and wherein the modifiable functional group comprises a protected functional group, that is not an acid-reactive functional group; a photoactive functional group; a base-reactive functional group; an electrochemically reactive functional group; a functional group that is reactive with electricity; or a combination thereof.

In another embodiment, the present invention is directed to macromolecular surfactants comprising at least two units each having a different surface tension, wherein the unit having the lowest surface tension comprises a modifiable functional group, and wherein the modifiable functional group comprises a protected functional group, that is not t-butyl and that is not an acid-reactive functional group; a photoactive functional group; a base-reactive functional group; an electrochemically reactive functional group; a functional group that is reactive with electricity; or a combination thereof.

In one embodiment, the modifiable functional group comprises a functional group protected with a low surface tension moiety. In another embodiment, the modifiable functional group comprises a methyl group, a $C_1$-$C_6$ alkyl group, a fluoro group, or a combination thereof.

In another embodiment, the macromolecular surfactant comprises a polyhydroxyethylacrylate, polyhydroxyethylmethacrylate, or a combination thereof.

The term "PS" is used herein to mean polystyrene.

The term "PDMS" is used herein to mean poly(dimethyl) siloxane.

The term "PMMA" is used herein to mean poly(methyl) methyacrylate.

The term "MMA" is used herein to mean methylmethacrylate.

The term "PtBA" is used herein to mean poly(t-butyl) acrylate.

The term "tBA" is used herein to mean t-butylacrylate.

The term "PtBMA" is used herein to mean poly(t-butyl) methacrylate.

The term "SAM" is used herein to mean self-assembled monolayer.

The term "monolayer" is used herein to mean a saturated layer one molecule thick.

The term "sub-monolayer" is used herein to mean a layer one molecule thick that is not completely saturated.

The term "PAG" is used herein to mean photoacid generator.

The term "XPS" is used herein to mean x-ray photoelectron spectroscopy.

The term "ADXPS" is used herein to mean angle dependent x-ray photoelectron spectroscopy.

The term "PGMEA" is used herein to mean propylene glycol methyl ether acetate.

The term "SEM" is used herein to mean scanning electron microscopy.

The term "unit" as used herein means a set of repeating monomers.

The term "$T_g$" is used herein to mean glass transition temperature.

The term "SDV" is used herein to mean Surface Delivery Vehicle.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, the word "or" means any one member of a particular list and also includes any combination of members of that list.

Modification

The invention is directed to molecular level methods to modify the structure and properties of material surfaces, especially polymeric surfaces. There are generally two goals involved: modifying the surface of some materials to impart release properties so that nothing sticks (e.g. a Teflon-like surface) and placing specific functional groups in well-controlled density at the surface (e.g. reactive sites to attach proteins).

Surface modification of usually low surface-energy polymers has attracted attention in order to improve their adhesion, wettability, printability, and biocompatibility with affecting their desirable bulk properties. The ability to modify and control chemical functionality on polymer surfaces in a precise manner is highly desirable because a change of surface chemistry changes the surface free energy and other material properties of interest, including adhesion and wettability, which are important in coatings and paints. It also allows for further surface derivatization of external ligands, which is an important way to build molecular assemblies with confined positions for more complex nanoscale and biomolecular devices.

Release Surfaces

Thermodynamic considerations show that making a release surface is straightforward. The lowest surface tension component is stable at the surface because it minimizes the surface free energy. To make a release surface on polystyrene, for example, a macromolecular surfactant that would be surface-active and lower the interfacial tension when it adsorbs at the surface is added to the PS surface. An example is a block copolymer comprising a polystyrene block and a poly(dimethyl)siloxane block. PDMS has a low surface tension and will assemble to the air-surface interface. PS anchors the copolymer to the surface because the PS block entangles with the PS substrate. This is depicted in FIG. 1.

The end result is a nanometer thick monolayer of PDMS on the PS substrate that causes the surface to act as if it were pure PDMS, which is a low surface tension release material. The PS block is required to anchor the molecule to the surface, and without it the PDMS surface layer could simply be wiped off the PS substrate.

The Cho thesis, Publication No. 3042898, ISBN 0-493-56739-9, demonstrated that a PS-PDMS block copolymer was coated on PS using supercritical $CO_2$. The PS substrate was placed in a chamber along with the block copolymer PS-PDMS and charged with supercritical $CO_2$. The coating forms through the self-assembly of the polystyrene portion of the block copolymer.

Functional Group Placement

Figure 2:
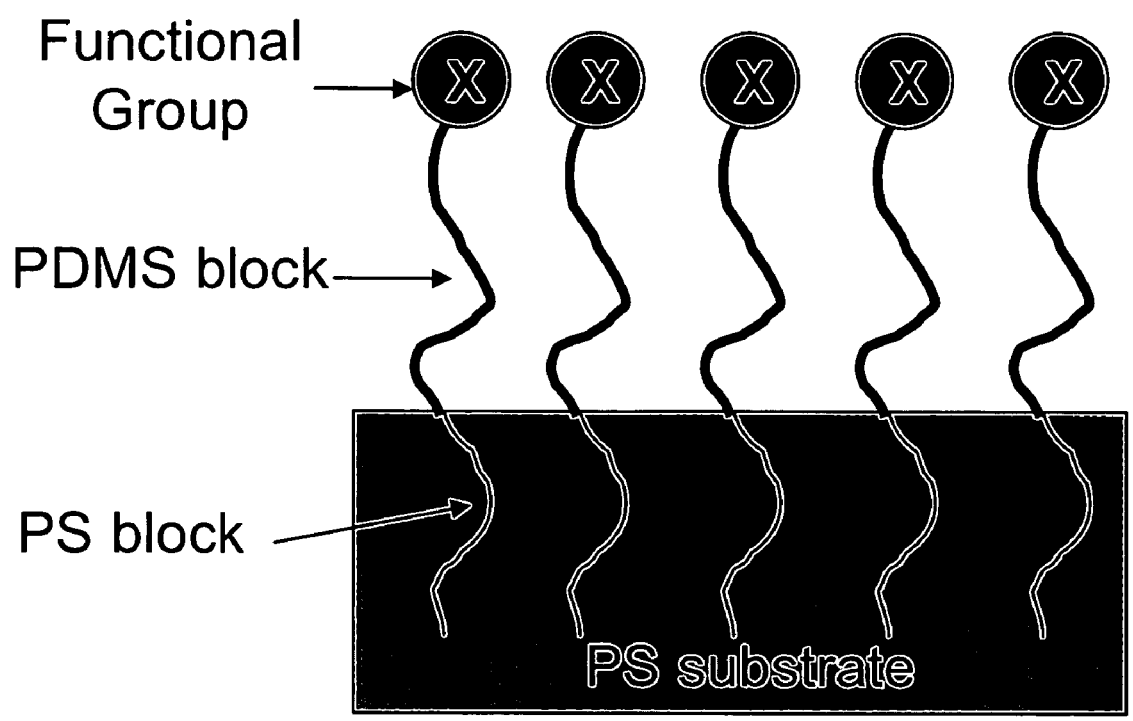
FIG. 2 depicts a poly(S-b-DMS-X) copolymer used to deliver functional group X to a surface.

One embodiment of this invention provides a method for creating a smart surface by placing a functional group on a polymeric chain end as depicted in FIG. 2. The properties of this surface are "smart" meaning that if a material comes in contact with this surface and has no interaction with the group X, the surface acts as a release surface, but if the material does interact with group X at the surface, the material will adhere. Thus, a smart surface responds to the material with which it is in contact and selectively adheres to the material depending on interaction of the material with group X on the surface.

The importance of this idea is that group X would not normally assemble at the surface because it is a functional group having a high surface tension or surface energy. Thermodynamically, the surface always wants to minimize its surface energy, so the high-energy group X will not assemble there on its own. According to the present invention, however, functional group X will assemble at the surface when attached to a macromolecular surfactant, because it is dragged along when the macromolecular surfactant self-assembles at the surface. Depending on the functional group X, the surface may also be further activated and patterned, as described in more detail below.

As an example, block copolymers containing protected functional groups are surface-active due to the nature of the protecting groups utilized, and they self-assemble at the surface to form a bilayer structure that presents a molecular layer of a protected block copolymer sequence to the surface. Through the molecular design of polymer architecture, surface modification of the polymer can be achieved without changing the bulk material properties. The molecular design can include self-assembly processes to create a modified polymer surface. The basis of the molecular design is that block copolymers with one low surface tension block are known to spontaneously self-assemble at the surface of a homopolymer matrix of higher surface tension. Most schemes for protection of reactive functional groups employ protecting groups that have intrinsically low surface tensions. Common protecting groups including trimethylsilane and t-butyl carbamate (BOC), impart low surface tension when used to protect a functional polymer because they contain three low energy methyl groups. As such, protecting groups such as trimethylsilane and BOC are examples of low surface tension moieties.

Functional Group Modification and Surface Patterning

In one embodiment, the invention provides a method for modifying a functional group at a surface. This includes, for example, deprotecting or activating a functional group at a surface. The invention also provides a method for spatially patterning precisely where these functional groups are activated. In one embodiment, this is accomplished with light by placing photoactivatable functional groups on a surface.

In one embodiment, self-assembling monolayers that specifically assemble on metallic and inorganic substrates are used. The self-assembling monolayer methodology is generally applicable to modify the chemistry of surfaces. The self-assembling molecule has one end group that associates with the metal causing the molecule to stand up. When the self-assembling molecule stands up at the surface, the other chain end, functionalized with a photoactive group, such as a t-butyl ester group, is located at the surface. Standard photoresist chemistry is used to convert this t-butyl ester group to a carboxylic acid group using a photoacid generator exposed to UV light. Because light is involved, surface functionality may be spatially patterned by exposure to UV light through an appropriate mask. Normally, carboxylic acid groups would not assemble at a surface because of their high energy. The methods of the invention, however, create a stable functional surface that can then be spatially patterned. Groups such as carboxylic acids provide convenient sites for further modification, including bioconjugation of peptides, proteins, and growth factors.

In another embodiment, polymers that specifically assemble on substrates are used. The polymer is, for example, a block copolymer. Depending on the concentration of copolymer used, the coating formed is either a monolayer or sub-monolayer. Block copolymers are designed to interact with polymeric substrates, or with metallic substrates, or with inorganic substrates, or a combination thereof. These block copolymers are also used for the photoactive surface modification strategy wherein functional groups are protected by chemistry that can be reversed upon exposure to light. One example of this chemistry is the t-butyl ester group, which can be photo-deprotected using UV light in the presence of a PAG, as shown in FIG. 3.

Figure 3:
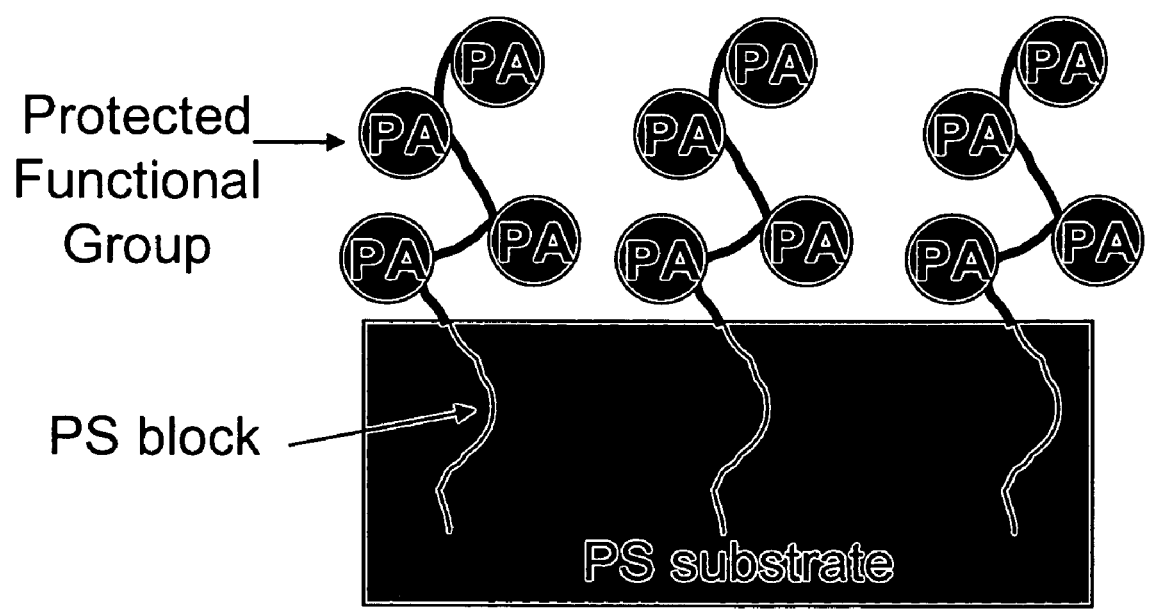
FIG. 3 depicts a surface modified with a block copolymer of polystyrene and a second block containing protected function groups.
Figure 4:
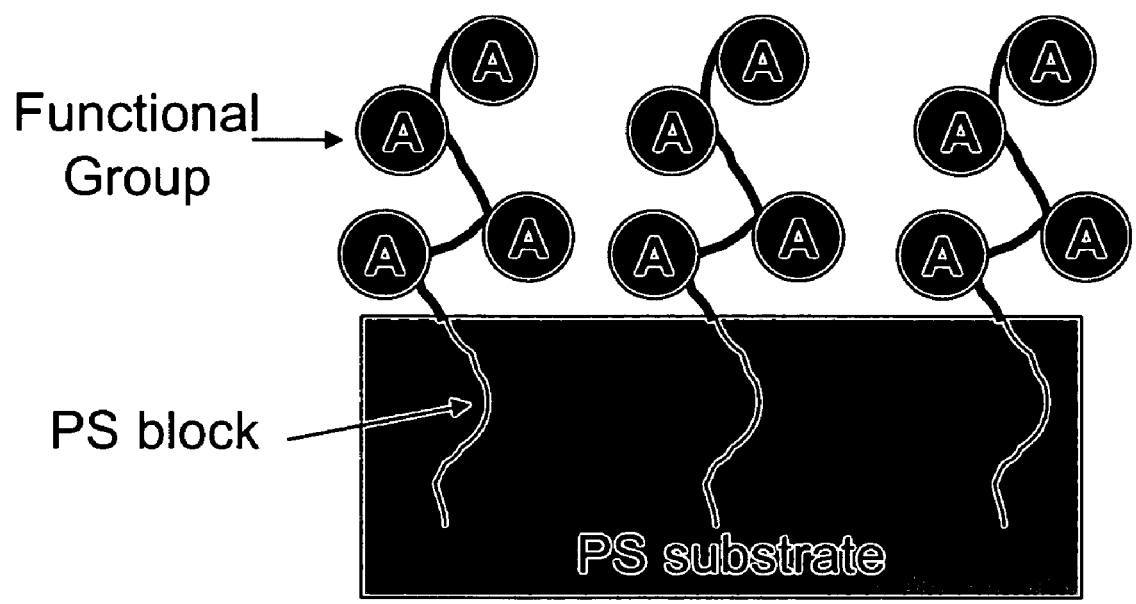
FIG. 4 shows the surface of FIG. 3 after photodeprotection by UV light in the presence of a photoacid generator.

When the surface is as shown in FIG. 3, it is usually a release surface because the protecting group P has a low surface energy and ties up the functional group A. When photodeprotected by a photoactive functional group PA or other possible means, the surface changes to give the surface shown in FIG. 4.

As an example, the protected group PA is a t-butyl ester. Accordingly, P is a t-butyl ester and A is a carboxylic acid. There are numerous possibilities. The group PA is any protected functional group with the following properties: the group imparts low enough surface tension that it makes the PA copolymer block surface active in the matrix (i.e., substrate), and the group forms a functional group upon exposure to UV light. The group PA could be a photo-deprotected moiety or a chemical structure that transforms into a useful functional group upon exposure to UV light.

Using standard photoresist technology, light causes a chemical transformation in the photoresist polymer that makes it soluble in the development solvent. Regions that are exposed to UV light are completely removed, leaving a topological feature, which is essentially a hole of proscribed shape. Ink can then be applied for photoresist stamping processes and will only adhere to the holes to produce the desired pattern.

In the invention herein, however, the same basic photoactive functional group chemistry is applied, but no surface material is removed. The photoactive functional group assembles at the surface by means of being incorporated into a macromolecular surfactant structure, and after transformation, it remains at the surface, allowing a change directly in the chemical makeup of the surface.

The surface modifications of the present invention allow latent surface treatment. In one embodiment, the protected surface shown in FIG. 3 is stable under standard storage conditions and can be activated (e.g., by photodeprotection) at a later time. This preserves the nature of the surface, and gives the experimenter greater flexibility in completing the desired surface modification.

In addition to controlling surface chemical functionalities in a homogenous way, the present invention provides methods for control the spatial distributions of the surface chemical functionalities, i.e. patterning polymer surfaces into heterogeneous surfaces with different chemical functionalities or hydrophobicity at well-defined regimes with micron or submicron feature size.

Photolithographic Patterning of End-Functionalized Self-Assembled Monolayers of Azobenzene on Gold There is an increasing need for the rapid development of molecular technologies and the miniaturization of new generation devices to fabricate highly ordered solid surfaces. Self-assembled monolayers have received attention as a building block for surface fabrication. SAMs have been used in the design of various interfaces for chemical sensors, optical switches, nonlinear optical materials, and high-density memory devices.

Highly ordered SAM surfaces on solid materials can also serve as templates for nanoparticles. Nanoparticles are ideal candidates for new generation devices. These devices require attaching a nanoparticle onto a solid surface by precisely controlling its size and position at the molecular level.

Azobenzene-based alkanethiol SAMs are capable of reversible photoisomerization. Azobenzene chromophores exhibit rapid and reversible trans-cis photoisomerization upon irradiation with UV or visible light. The large structural and dipole moment change associated with this isomerization also causes significant optical and surface property changes. The azobenzene chromophore is also electrochemically active. Thiol based SAMs also show this switchable behavior. The surface is patterned using this switching property. One way to show patterning on surface is by monitoring change in wettability of surface before and after irradiation.

Applicants' research investigates the chemical and optical properties of several different end-functionalized azobenzene moieties that form SAMs on flat and crust gold surfaces. In one embodiment, the invention is directed to patterning a functionalized azobenzene surface using chemical (by photolithographic techniques) and physical patterning (optical switching properties). A patterned azobenzene surface is generated using conventional photolithographic techniques. Self-assembled monolayers of t-Bu terminated azobenzene on gold substrate are prepared and characterized using contact angle measurement and XPS. Self-assembled monolayers of hydrophobic-group-terminated azobenzenes on gold are patterned with light and a photomask to generate a hydrophilic surface. The hydrophobic and hydrophilic groups show very different wetting behavior and the patterned surface is visualized by optical microscopy after condensation of water. The hydrophobic and hydrophilic patterned azobenzene surface can also be imaged with amine terminated polystyrene particles and fluorescence labeled PS nanoparticles. Photochemically patterned surfaces therefore serve as a means for templating two-dimensional geometric patterns of a variety of objects and molecules.

In one embodiment, the invention is directed to a photolithographic technique for direct photochemical modification and chemical patterning of surfaces. In one embodiment, the technique involves self-assembly of t-butyl ester end-functional alkanethiols onto gold substrates. XPS confirms that self-assembly causes terminal t-butyl ester groups to locate at the air-monolayer interface, and the t-butyl ester groups are subsequently converted to carboxylic acid groups when exposed to UV radiation in the presence of a photoacid generator. The photochemical change from hydrophobic t-butyl ester groups to hydrophilic groups has a profound effect on surface wettability. Surface chemistry is patterned with this process on a microscale by exposure to UV light through a patterned photo-mask. Unexposed regions retain the properties associated with hydrophobic t-butyl ester end-groups, while exposed regions are converted to carboxylic acid surface chemical functionality.

In another embodiment, the photomasking technique is an effective and simple means for templating two-dimensional surface deposition of a variety of molecules and objects. The resultant hydrophobic and hydrophilic surface regions are used to spatially pattern: fluid wetting (i.e., water), the adsorption of amine-terminated polystyrene colloidal particles, and the deposition of amine-terminated, fluorescence-labeled polystyrene nanoparticles. The surface patterning technique retains the full resolution of deep UV photolithography, requires only light and a photoacid generator as reagents, and can be performed with conventional deep UV photomasking systems.

Polymer Design

The copolymer exemplified herein is a diblock copolymer. Many alternative polymer architectures are also applicable. A pure homopolymer with PA units is useful, so long as the homopolymer will readily associate with the substrate polymer. For example, a PS substrate may be modified with PtBA homopolymer. Other applicable polymers include triblock copolymers, graft copolymers, star copolymers, random copolymers and multiblock copolymers, including segmented copolymers. In these examples, the only requirement is that one block is an anchor block that associates strongly with the substrate polymer and the other block is surface-active and contains the photoactive PA moiety. The structure depicted in FIG. 2 is also useful where group X is replaced by the protected photoactive group PA. In this case the surface active block copolymer is an end functional block copolymer in which the surface active block is anything with a low enough surface tension to cause the copolymer to self-assemble at the substrate surface. Exemplary copolymer components include silicones, fluoroacrylates, methacrylates, acrylates, and fluorocarbons.

Example 1 below describes a polystyrene substrate, but the invention is applicable to all substrates that are wettable by poly(t-butyl acrylate) or, more generally, are wettable by the block containing a protected PA functionality. The anchor block of the block copolymer is either the same as the substrate polymer, or interacts favorably with the substrate polymer. For example, the anchor block could be poly(methyl) methacrylate for a PMMA substrate, allowing a PMMA substrate to be modified with a poly(MMA-b-tBA) copolymer.

In designing a polymer to interact with a substrate, certain parameters are considered. The sequences or blocks of the polymer are selected based on the substrate to be coated. The polymer comprises an anchor block that favorably interacts with the substrate. This favorable interaction can be measured, for example, by an exothermic interaction between the substrate and the polymer. The substrate and the polymer are held together by entropic and energetic forces.

The anchor block is the same as (e.g., a homopolymer), or different than (e.g., a copolymer), the block comprising the functional group that assembles to the air-coating interface of surface. The anchor block is selected based on its ability to associate with the substrate. Depending on the nature of the substrate, this association is by physisorption, chemisorption, or molecular interpenetration of the polymer onto the substrate. For example, when the substrate also comprises a polymer, the substrate polymer may mix with the anchor block polymer. Suitable mixing polymers are known to those of skill in the art. The anchor block polymer may also be miscible in the substrate polymer. As another example, when the substrate is inorganic, the anchor block may chemically bond or chemisorb to the inorganic substrate. The chemical bonding or chemisorption could occur through the interaction of a single functional group or a block of functional groups.

Design of Surface Delivery Vehicles

Polymeric Substrates

Surface delivery vehicles for polymeric surfaces can be prepared from a variety of copolymer architectures: random, diblock and triblock, graft, star and multiblock. Each SDV has at least two and usually three monomer units that comprise the polymer molecules. One of the units interacts with the substrate with sufficient strength to make it difficult to remove the SDV from the substrate surface. This monomer is referred to as the anchor block because it anchors the SDV to the substrate. Several mechanisms for anchoring are possible. For example, the anchor block may penetrate into and entangle with the substrate due to miscibility. If the substrate is polystyrene, the anchor block is polystyrene or any other polymer that is miscible with polystyrene, e.g., poly(vinyl methyl ether). Alternatively, the anchor block may simply chemisorb or physisorb to the substrate.

The second monomer unit has a lower surface tension than that of the anchor block to cause the SDV to segregate to the surface. It also has a sufficiently unfavorable interaction (i.e., large enough Flory interaction parameter, $\chi$ with the anchor block and sufficient length to cause the SDV to self-assemble into a bilayer-like structure with the outermost air-interface layer comprising the low surface tension block and the inner layer comprising the anchor block.

SDVs also contain a functional moiety or moieties that can be activated using light or other external stimuli, including electrical or magnetic fields. The functional moieties are either incorporated into the low surface tension block or are end groups of the low surface tension block. The functional moiety can be a protected functional group that can be deprotected by light, e.g., a t-butyl ester that yields a carboxylic acid upon photolytic deprotection, or can be a group that can be transformed or derivatized by a known photoreaction, e.g., a benzophenone group that can graft surface molecules by radical abstraction when exposed to light. The functional moiety may also be a group that can be transformed into an active species by an electrochemical reaction applied with a scanning tunneling microscope or atomic force microscope. These latter techniques are useful for nanometer scale patterning of functional groups at surfaces.

In general, the low surface tension block causes the SDV to segregate to the polymer surface. In doing so, it delivers attached functional groups to the surface. The anchor block provides energy of interaction or interpenetration that makes the SDV stick to the substrate surface and provides a repulsive energy with respect to the low surface tension that promotes self-assembly of the SDV as a bilayer at the substrate surface. The outermost layer of the surface bilayer obtained comprises the low surface tension block and any functional moieties that are attached as side chains or end groups, while the innermost layer is the anchor block adhering the SDV to the substrate.

Non-polymeric Solid Substrates

SDVs for non-polymeric solid substrates are based on the designs discussed above for polymeric substrates. However, the anchor block cannot penetrate the substrate and physisorbs or chemisorbs with sufficient adhesive force to anchor it to the substrate. For copolymer SDVs, the anchor block is functionalized with specific groups that interact strongly with the solid substrate. Examples of functional groups are ethoxy, choloro or silanes for glass, quartz and silicon wafer substrates; thiols or sulfides for coinage metal substrates including gold and copper; and carboxylic acids for aluminum.

Self-assembled monolayers can also be used as SDVs. These SAMs have a three-component design. The first component is a functional group at the first end of the molecule that reacts with or interacts strongly with the substrate. Examples again include ethoxy, choloro or silanes for glass, quartz and silicon wafer substrates; thiols or sulfides for coinage metal substrates including gold and copper; and carboxylic acids for aluminum substrates. The second component is the self-assembling molecule, which comprises moieties that self-associate strongly. A hydrocarbon chain comprising more than about seven methylene units is typically used for this purpose. The third component is a functional group at the second end of the molecule. This group is initially a low surface tension group that is activated upon exposure to light or other stimuli to form the surface functional group of interest.

In general, the first end groups on the anchor block interact strongly with the substrate so that the self-association energy between the molecular backbones causes an orientational transition that positions the first end attached to the substrate, orients the molecule more or less perpendicular to the substrate, and positions the second end group at the surface and. In this fashion, the SAM-based SDV design delivers the functional moiety of interest to the air-substrate interface.

Coating Techniques

General methods of coating a substrate with a polymer or macromolecular surfactant are known to those of skill in the art. These methods include, without limitation, self-assembly methods, spin coating and adsorption.

In one embodiment, the invention provides methods of coating a substrate with a nanometer thickness of a polymer. In one embodiment, the coating thickness provided by these methods is uniform. The coating thickness obtained is, for example, a sub-monolayer, a saturated monolayer, or two layers. Changing the initial polymer concentration will cause a change in the coating thickness. This is also a simple and straightforward method for coating polymeric or other substrates with a sub-monolayer to monolayer coating of a macromolecular surfactant, as depicted in FIGS. 2 and 3.

The ability of the polymer to coat the substrate depends on the architecture and size of the sequences or blocks of the polymer. For example, in order to form a fully saturated monolayer on a substrate, the concentration of polymer will be such that adjacent polymer subunits are closely packed but not overlapping. Because the polymer sequences comprise coiled atomic chains, there is a relationship between the length of a sequence chain and the width of substrate that it covers. The polymer coating is visualized with XPS to measure the thickness of the coating versus concentration of polymer used. A break in the XPS curve gives the concentration of polymer corresponding to an exact monolayer coating.

Supercritical Fluids

In another embodiment of this invention, the polymer is coated on a substrate using supercritical $CO_2$. The use of supercritical $CO_2$ provides several advantages. For example, supercritical $CO_2$ is useful to coat a polymer monolayer onto a substrate of arbitrary shape and can be used to coat the internal pores of porous objects or to coat inside tubes. It also does not require the use large amounts of volatile organic compounds. Supercritical $CO_2$ is an environmentally friendly solvent.

In one embodiment, the polymer is soluble in the supercritical $CO_2$, and the presence of a functional group on the polymer does not cause the polymer to become insoluble in supercritical $CO_2$. Examples 1 and 2 below describe the use of poly(S-b-tBA), which is a photoactive, surface active copolymer and polystyrene as the substrate. The photoactive functional groups and copolymer structures described are applicable as long as the macromolecular surfactant is both surface-active and soluble in the supercritical fluid. In one embodiment, the surface-active functional group is protected to prevent reaction of the supercritical $CO_2$ with the functional group.

The supercritical fluid used in these examples is $CO_2$, but also includes, for example, $CO_2$ containing small amounts of organic solvents such as methanol and ethanol to enhance the solubility of the copolymer in the supercritical fluid.

Criteria for selecting pressure and temperature parameters are known to those of skill in the art. When using a supercritical fluid, the lowest possible pressure that dissolves a sufficient amount of the polymer is used. The temperature is low enough so that it causes degradation of the polymer. In some embodiments, room temperature is used. The use of trace organic solvents in the supercritical fluid will also influence the selection of pressure and temperature parameters.

Exemplary Uses of Modified Surfaces

The methods of the present invention are useful for patterning surfaces. Surface patterning refers to creating two-dimensional spatially heterogeneous surfaces with different chemical functionality, hydrophobicity, or morphology as well-defined regimes with micron or submicron feature sizes [Pan et al., *Polymer Preprints* 2003, 44(1), 500].

The present invention has applications in thin film device fabrication, particularly in microelectronics, information storage, optics, and sensors [Blaaderen, A. V. et al., *Nature* 1997, 385, 321].

For example, a polymer surface applied to a surface acoustic wave sensor can serve as an artificial nose or sniffer system. Thin polymer films are coated onto quartz, and an aldehyde group on the surface reacts in the presence of light. Adsorption causes a change in the wave sensor. The polymer coating is used to create a stable surface that normally would not be stable.

As another example, the patterned surfaces produced by the methods of the present invention are useful as universal templates to assist self-assembly and selective deposition of an object of interest, including polymers and inorganic colloidal particles, nanoparticles, photonic crystals, and biomolecules [Yin, Y. et al., *J. Am. Chem. Soc.* 2001, 123, 8718]. The immobilization and patterning of biomolecules on solid surfaces is important to the development of biologically integrated devices such as biosensors, genomic diagnostics, modulation of cell-substrate interaction, controlled drug release, and tissue engineering.

It is also desirable to pattern biomolecules on polymer substrates instead of on conventional silicon or glass inorganic substrates because polymers are more versatile and meet the requirements of processibility, physical strength, gas permeability, and biocompatibility. Polymer substrates also have the advantage of being low cost, disposable, and environmentally friendly. The biomolecular patterning approach of the present invention also has the advantage of easy implantability from mature microelectronic technology. Pattern feature resolution can be extended to the resolution of current commercial microchips. Further, the examples shown herein are amenable to patterning biomolecules because the materials and reagents used are biocompatible.

The methods of the present invention are also applicable to nanopatterning.

The devices of the present invention have latent functionality and are amenable to storage and later activation.

The invention will be further described with reference to the following examples; however, it is to be understood that the invention is not limited to such examples. Rather, in view of the present disclosure that describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

EXAMPLE 1

4 mg of polystyrene-b-poly(t-butyl acrylate) (6.4K-7K, Polymer Source) was inserted into a high-pressure cell in every experiment regardless of carbon dioxide pressure. The corresponding concentration was 0.1 mg/cm$^3$. PS fibers were placed inside a microcentrifuge tube located inside the high-pressure cell. The cell was charged with $CO_2$ to desired pressure using an ISCO pump (260D). The temperature of the cell was controlled at 40° C. PS fibers were characterized with XPS and SEM.

Figure 5:
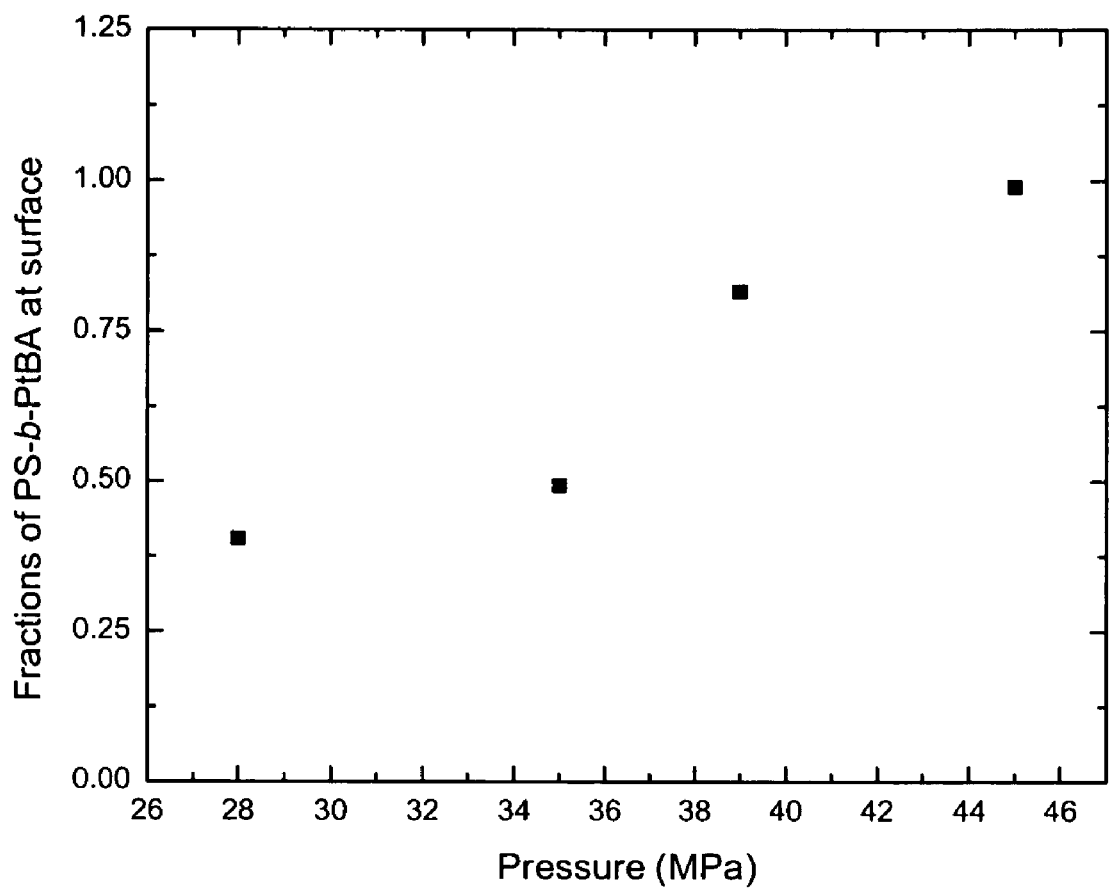
FIG. 5 depicts the polystyrene-poly(t-butyl)acrylate adsorption isotherm on PS fibers.
Figures 6A, 6B:
FIG. 6A and FIG. 6B are scanning electron micrograph images of original PS fibers and PS fibers after being coated with block copolymer.

The block copolymer, PS-b-PtBA, starts to adsorb onto PS fibers when the pressure of $CO_2$ is above 25 MPa. FIG. 5 shows that the surface coverage of PS-b-PtBA increases with the pressure of $CO_2$. At 46 MPa, PS-b-PtBA totally covers the surface. FIG. 6 gives the SEM images of PS fibers before and after covering with block copolymer. The original PS fibers have small pores at the surface. After coating, the pores disappeared and very smooth surfaces were obtained.

Figure 7:
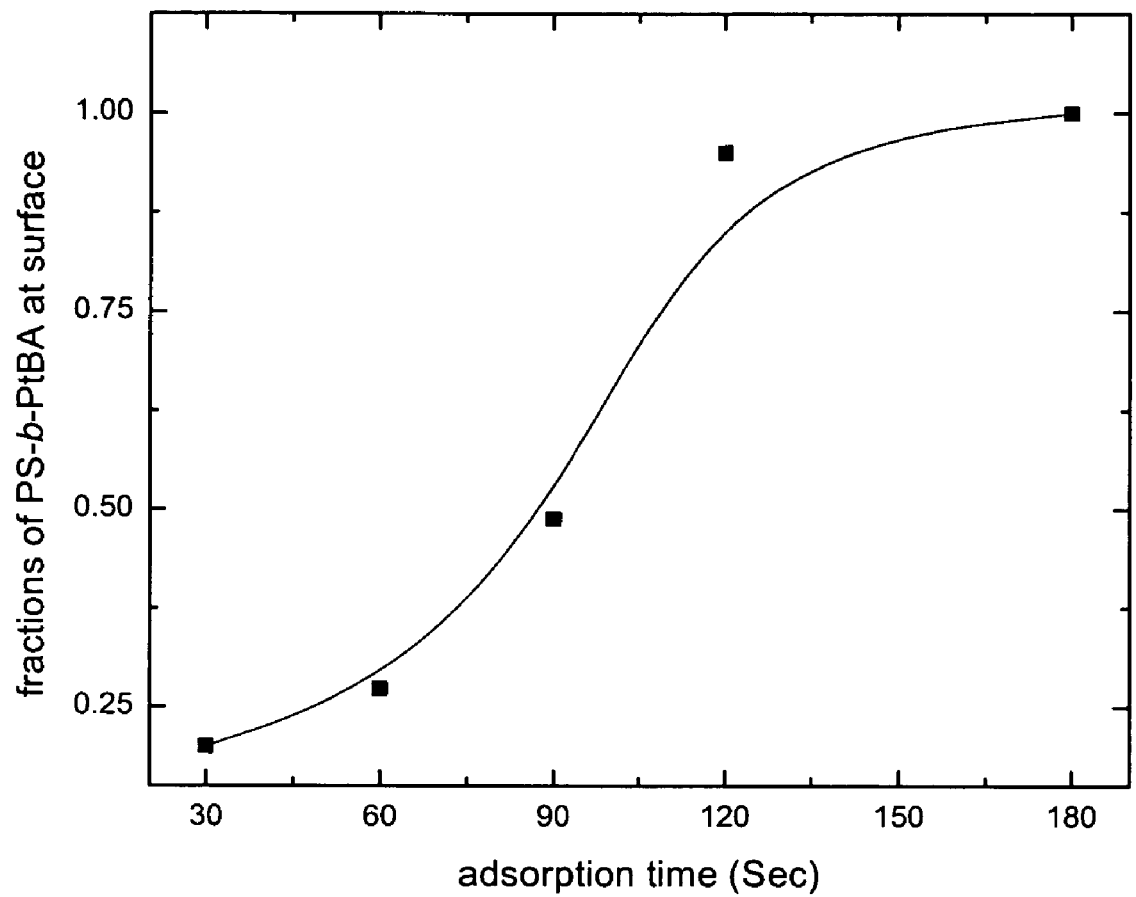
FIG. 7 shows surface coverage of PS-PtBA versus adsorption time.

The adsorption kinetics of PS-b-PtBA from supercritical $CO_2$ was investigated. XPS cannot detect any block copolymer at surface until the resident time reaches 30 seconds. Increasing the resident time increases the surface coverage of PS-b-PtBA. PS-b-PtBA totally covers the surface after about 2 minutes, as depicted in FIG. 7.

EXAMPLE 2

1 mg of polystyrene-b-poly(t-butyl acrylate) (6.4K-7K, Polymer Source) was inserted into a high-pressure cell in every experiment regardless of carbon dioxide pressure. The corresponding concentration was 1.32 mg/cm$^3$. A piece of silicon wafer was first spin coated with a layer of PS (152K, Pressure Chemical) with a thickness of about 50 nm, then placed inside a high-pressure cell. The cell was charged with $CO_2$ to desired pressure using an ISCO pump (260D). The temperature of the cell was controlled at 46° C. The cell was maintained at the pressure for half an hour before releasing $CO_2$. The modified samples were characterized with the contact angle measurement and XPS.

Figure 8:
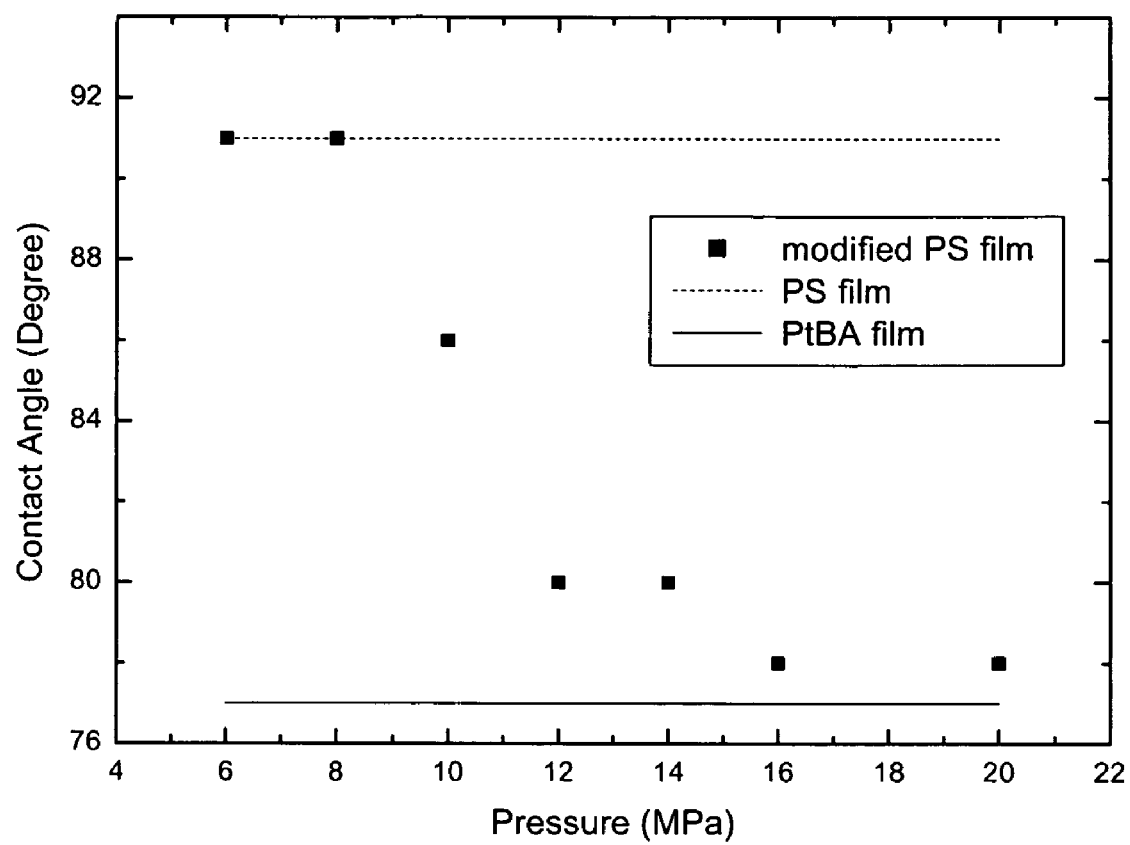
FIG. 8 illustrates contact angle measurements of modified PS films.
Figure 9:
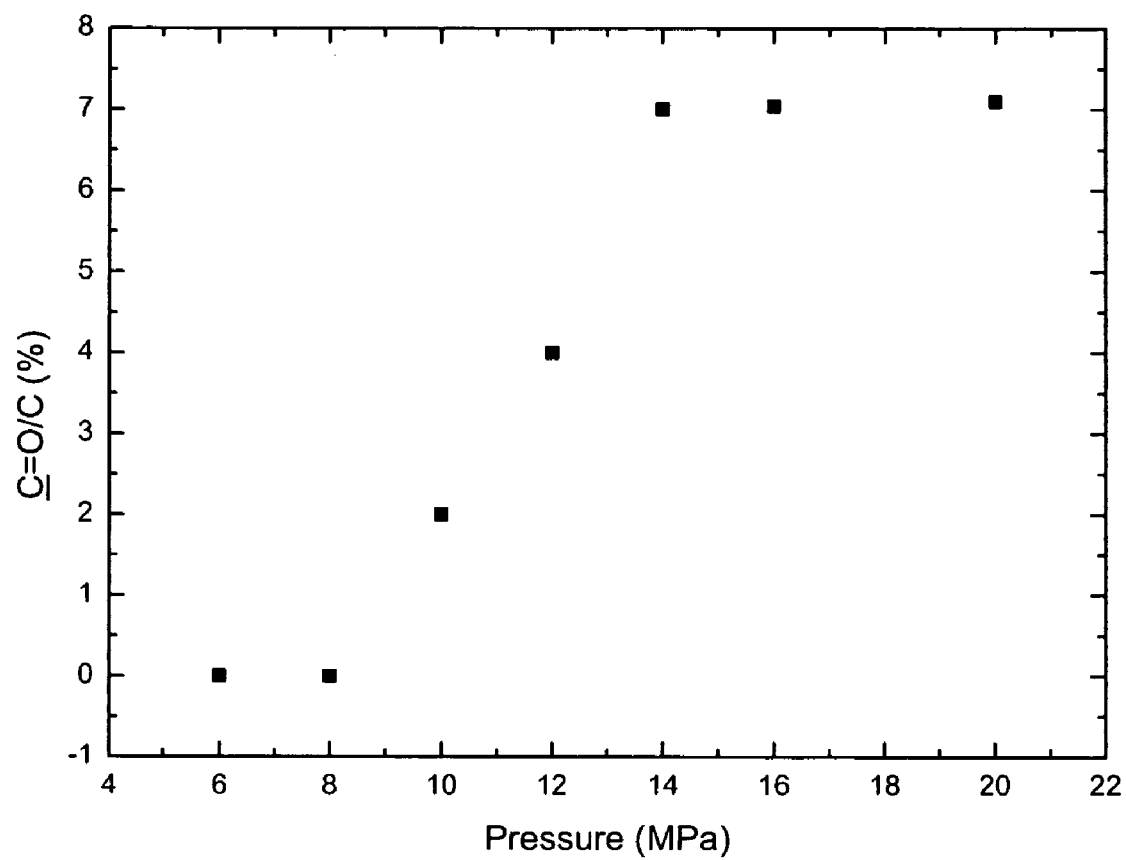
FIG. 9 is an x-ray photoelectron spectroscopy output showing concentration of carbonyl carbon coating a polystyrene surface.

Contact angles of water on PS and PtBA films were measured and compared with those on the modified PS films (FIG. 8). The ratio of carbonyl carbon to total carbon can be obtained from XPS, because PtBA is the only source of carbonyl carbon. The XPS results are shown in FIG. 9. When $CO_2$ pressure is below 8 MPa, no significant adsorption of block copolymer was observed. When the pressure between 8 and 16 MPa, the concentration of PtBA at the surface increases with pressure. As a result, the contact angle decreases and the concentration of carbonyl carbon at the surface increases with pressure. Above 16 MPa, a plateau is reached and the surface concentration of PtBA does not change with pressure.

Figure 10:
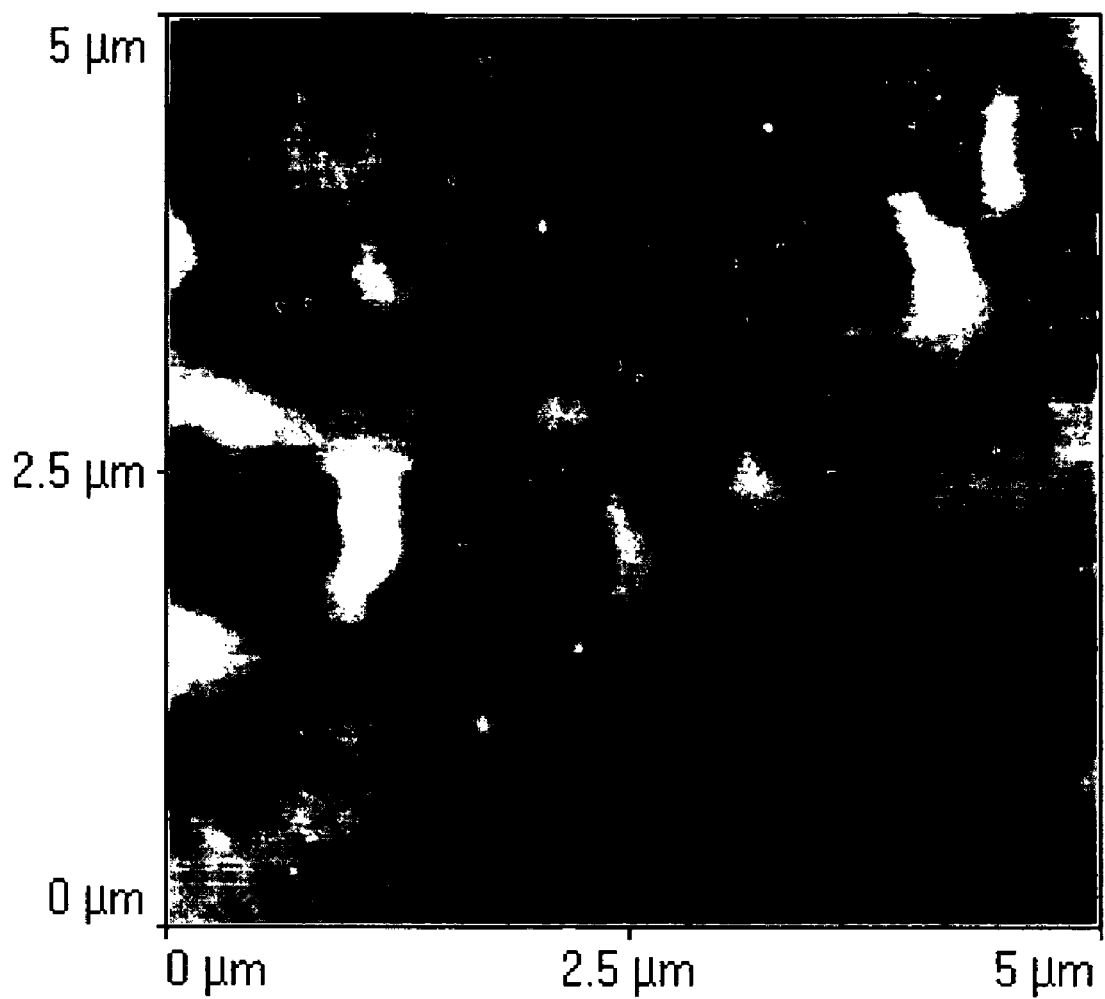
FIG. 10 depicts adsorption of copolymer onto silicon wafer.

Bare Si wafers were also applied as substrates to study the adsorption of block copolymer. Unlike adsorption on PS films, visible defects can be observed after adsorption of copolymer onto the Si wafer (FIG. 10). The thickness of copolymer layer is about 5 nm, which is close to the radii of gyration of the block copolymer. This suggests that the copolymer forms a single molecular layer on top of the substrate.

EXAMPLE 3

Self-Assembled Monolayers

Synthesis of 4-[4-(6-Mercapto-hexyloxy)-phenylazo]-benzoic acid t-butyl ester (Compound 1)

4-[4-(6-Bromo-hexyloxy)-phenylazo]-benzoic acid t-butyl ester was synthesized following a reported procedure [*Macromolecule*, 1993, 26, 7103-05; *J. Fluorine Chem.*, 1995, 74]. 4-Amino-benzoic acid t-butyl ester (Fluka, 4.81 g, 25 mmol) was dissolved in 55 mL of dilute hydrochloric acid aqueous solution. After cooling in an ice bath, the acid mixture was diazotized by adding drop-wise a solution of 1.73 g of NaNO$_2$ in 5 mL of water at 0° C. to the acid mixture. The solution mixture turned a strong yellow. The solution was diluted with 100 mL of chilled methanol and coupling was carried out by slowly adding the diazotized solution to a chilled solution of phenol (2.34 g, 24 mmol), KOH (2.69 g, 48 mmol), and 25 mL of MeOH at 0° C. to form an orange-yellow precipitate. The solution was stirred for 2 hours in an ice water bath. The precipitate was filtered off, dried and recrystallized from n-hexane to obtain an orange-yellow solid (6.41 g, 87 %). A mixture of 3.4 mmol of 4-(4-hydroxyphenylazo)-benzoic acid t-butyl ester, 33.6 mmole of 1,6-dibromohexane, 16.8 mmol of dry potassium carbonate and a catalytic amount of potassium iodide in 25 mL of dry acetone was stirred under reflux overnight. Reaction completion was confirmed by thin layer chromatography analysis. After cooling, the precipitated salt was filtered off and the filtrate was concentrated in vacuo. The crude product was purified by recrystallization from hexane/ethyl acetate (70:30) to obtain a shiny orange powder (yield 91 %, 1.41 g).

4-[4-(6-Mercapto-hexyloxy)-phenylazo]-benzoic acid t-butyl ester was synthesized by modifying a literature procedure [*Material Science and Engineering*, 1999, 8-9, 385-389; *J. Phys. Chem.*, 1995, 99, 7102]. 0.41 g (0.9 mmol) of 4-[4-(6-bromo-hexyloxy)-phenyazo]-benzoic acid t-butyl ester and 0.25 mg (1.1 mmol) of sodium thiosulfate pentahydrate in 5 mL of water was dissolved in 18 mL of ethanol and refluxed for 3 hours. The mixture was stirred at room temperature for an additional hour. After cooling, the precipitate was filtered off using a fritted funnel. A fine orange solid (bunte salt) was obtained and was used without purification. 10 ml of chloroform and 10 mL of 1M HCl were added to the bunte salt. The reaction mixture was refluxed for 2 hours at 70° C. after which the orange organic phase was extracted from the colorless aqueous layer. The organic layers were further extracted with 10 mL of chloroform (3 times) and combined, washed with saturated NaHCO$_3$ solution, distilled water, and then dried over MgSO$_4$. The solvent was removed by roto-evaporation and the product (compound 1, FIG. 11) was further purified by recrystallization from an ethanol-water mixture. Drying under vacuum produced a fine orange powder (0.22 g, 60% yield) with the following characteristics: $^1$H NMR (CDCl$_3$) δ 8.11 (d, J=9 Hz, 2H), 7.91 (dd, J=9 Hz, 4H), 7.14 (d, J=9 Hz, 2H), 4.08 (t, J=6 Hz, 2H), 2.48 (m, 2H), 1.85-1.41 (m, 17H), 1.32 (t, 1H). High-resolution mass spectroscopy (HR-MS) yielded a mass of 414.1988 compared to the value 414.1628 calculated for C$_{23}$H$_{30}$O$_3$N$_2$S.

Synthesis of 4-[4-(6-Mercapto-hexyloxy)-phenylazo]-benzoic acid (Compound 2)

An excess of trifluoroacetic acid (99%, Acros) was added to 0.2 g of 4-[4-(6-mercapto-hexyloxy)-phenylazo]-benzoic acid t-butyl ester. The mixture was stirred for 5 minutes to dissolve. Excess trifluoroacetic acid was flushed from the vessel using a stream of argon. Acetone was added to the crude mixture to remove unreacted starting materials. The deprotected product acid was solidified by acetone and filtered out. The solid product (compound 2, FIG. 11) was further purified by washing with several portions of acetone. The yield was 90-95%, and product characteristics were: $^1$H NMR (DMSO-d$_6$) δ 13.08 (broad, 1H), 8.10 (d, J=9 Hz, 2H) 7.89 (dd, J=9 Hz, 4H), 7.11 (d, J=9 Hz, 2H), 4.06 (t, J=6 Hz, 2H), 2.7 (m, 2H), 1.78-1.25 (m, 9H). HR-MS (M+1) gave a mass of 359.1441 compared to the theoretical value of 359.1429 for C$_{19}$H$_{23}$O$_3$N$_2$S.

Preparation of Azobenzene Alkanethiol Self-Assembled Monolayers (SAMs)

SAMS of azobenzene derivatives were prepared on Au(111)/Cr/Si wafer. SAMs of the azobenzene alkanethiols were prepared by immersing gold substrates for 12-24 hours in 1.0-0.1 mM ethanolic or THF solution of the azobenzene alkanethiol derivatives, followed by rinsing thoroughly with the corresponding solvent, and drying in a stream of nitrogen prior to the characterization. To confer free volume to the azobenzene moiety and facilitate photoisomerization in the closely packed monolayer, azobenzene thiol solutions were irradiated under UV before and during deposition to deposit as the cis conformation. Gold substrates were prepared by evaporating 10 nm chromium, followed by 100 nm gold (99.99%), onto 3" N (100) prime grade silicon wafers (Wafer World, Inc.). Silicon wafers were cleaned by piranha etching before and after gold deposition, rinsed with copious amounts of de-ionized water, acetone and methanol, and dried in a stream of nitrogen.

Photochemical Modification and Chemical Patterning

A sacrificial layer (>1 µm) of polystyrene (MW=250K, 99%, Acros) containing the PAG triphenylsulphonium triflate (donated by IBM) (7.9 % w/w PAG/PS) was spin coated on top of self assembled monolayers from a (7.2% w/w) solution of PS/PAG in PGMEA (Aldrich). The sample was then exposed to a mercury lamp (254 nm, 760 µw/cm$^2$) for 10-30 seconds in the presence of a photo-mask. The UV exposed sample was post-baked at 100° C. from 30 seconds to 1 minute to facilitate the diffusion of the photogenerated acid molecules. Excess PAG and PS were removed by washing with toluene and samples were dried under $N_2$.

Sample Characterization

UV-Vis spectra were obtained using a Shimadzu, UV-2401PC UV-Vis recording spectrophotometer.

Contact angle measurements were performed with a Rame-Hart 100-00 contact angle goniometer using Millipore Mili-Q water. A drop of 1 µL volume was formed from a micropipet and placed directly onto the sample. At least three droplets were measured on each sample. The sample variation for a given SAM type was less than 2°.

X-ray Photoelectron Spectroscopy (XPS) spectra were recorded with PHI 5500 model Spectrometer equipped with an Al Kα monochromator X-ray source run at 15 kV and 23.3 mA, a hemispherical electron energy analyzer and a multichannel detector. The test chamber pressure was maintained below $2\times10^{-9}$ torr during spectral acquisition. A low energy electron flood gun was used to neutralize the possible surface charge. The XPS binding energy was internally referenced to the aliphatic C1s peak (BE=284.6 eV). Survey spectra were acquired using an analyzer pass energy of 93.9 eV and BE resolution of 0.8 eV, and high resolution spectra was acquired with a pass energy of 23.5 eV and BE resolution of 0.05 eV. The take-off angle is defined as the angle between the surface normal and detector. ADXPS was performed by using a motor to rotate the sample holder to the desired take-off angle. High resolution spectra were resolved by fitting each peak with Guassian-Lorentz functions after subtracting the background using the PHI data processing software package under the constraint of setting a reasonable BE shift and characteristic full width at half maximum range. Atomic concentrations were calculated by normalizing peak areas to elemental sensitivity factor data provided by the PHI database.

Fluorescence imaging of surfaces was performed using an Olympus IX70 laser scanning confocal microscope equipped with an Ar laser as an excitation source. The sample was excited at 488 nm and the corresponding emission was collected above 510 nm. Fluorescence intensity was monitored as a function of X-Y position as the sample was focused above the laser beam through a 20× or 10× objective. Fluorescence images (512×512 pixels) were typically acquired at a PMT voltage of 900 V and a scan speed of 16 scans per second.

Light micrographs were recorded using a Nikon OPTIPHOT metallurgical dark field microscope equipped with a Kodak MDS digital camera in the reflection mode. The image was typically acquired using a 20× and 5× objective.

Visualization of Chemically Patterned Surface

Chemical surface patterns were visualized by condensing water onto the patterned surface [*Science* 1993, 260, 647; *Science* 1994, 263(5143), 60], by acid-base interaction mediated adsorption of amine-functional PS colloidal particles (diameter 3 µm, 2.6 % solid latex suspension) (PolyScience, Inc.), and by decoration with fluorescently tagged PS nanoparticles. A suspension of 0.1 % w/w PS-$NH_2$ colloidal particles in aqueous solution was prepared and applied on the patterned surface. The sample was then slightly heated at 50° C. for 1-3 hours to evaporate the water.

Figure 11:
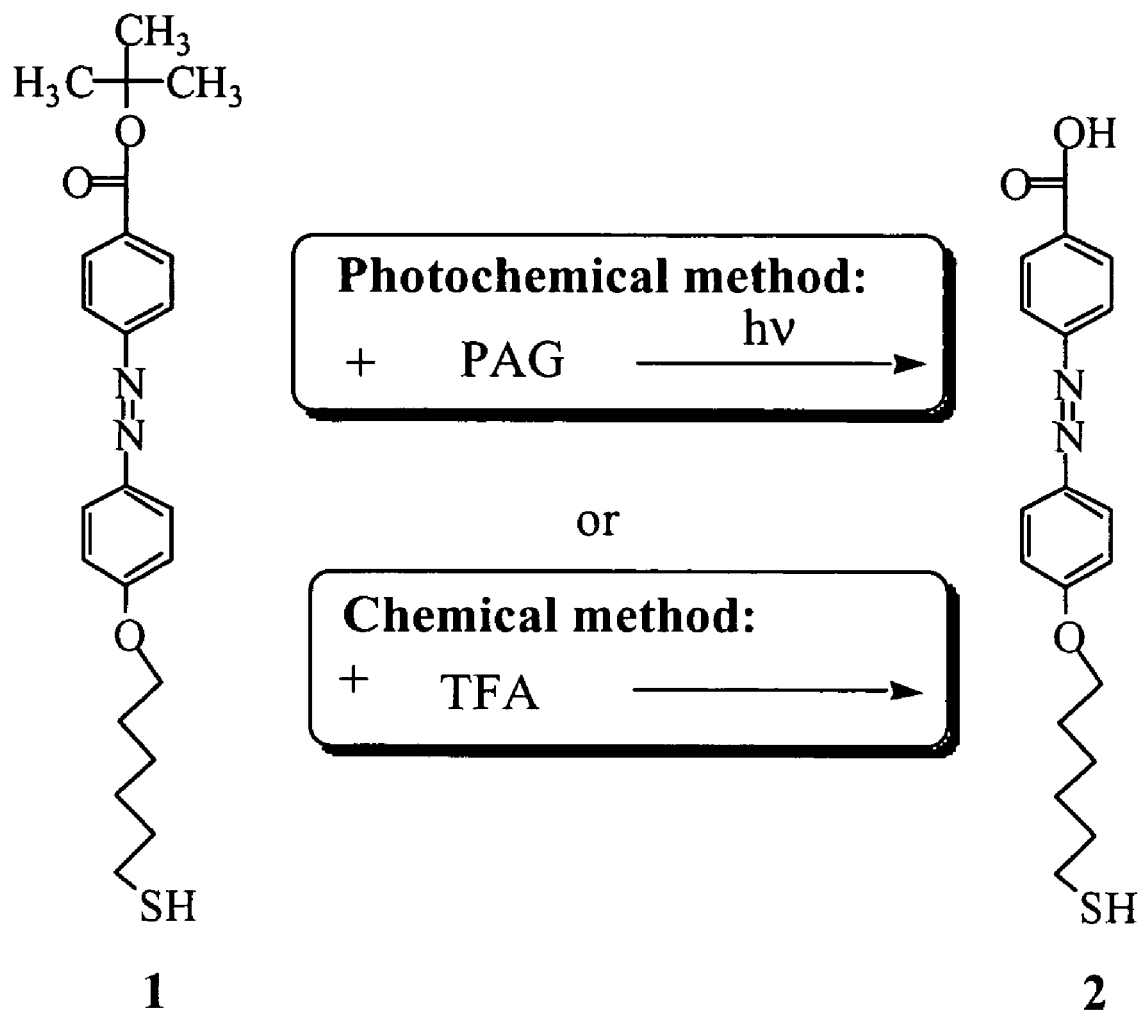
FIG. 11 shows the deprotection of compound 1 by photochemical or chemical means to form compound 2.

As illustrated in FIG. 11, the t-butyl ester functionality provides a site for a photochemical change from a hydrophobic butyl group to a reactive hydrophilic carboxylic acid group. This same photochemical change forms the basis of chemical amplification photoresist technology [*Langmuir* 2002, 18(23) 8720]. When exposed to UV light, the photoacid generator produces a proton that catalyzes deprotection of the t-butyl ester (compound 1, SAM-tBu) to form a carboxylic acid (compound 2, SAM-COOH) and butylene gas. Photo-deprotection of the hydrophobic t-butyl ester to form a carboxylic acid offers a photo-chemical alternative to more traditional chemical deprotection methods, such as hydrolysis with trifluoroacetic acid, also depicted in FIG. 11. Both of these deprotection schemes occur readily in solution to produce an acid-terminated azobenzene alkanethiol compound.

Figure 12:
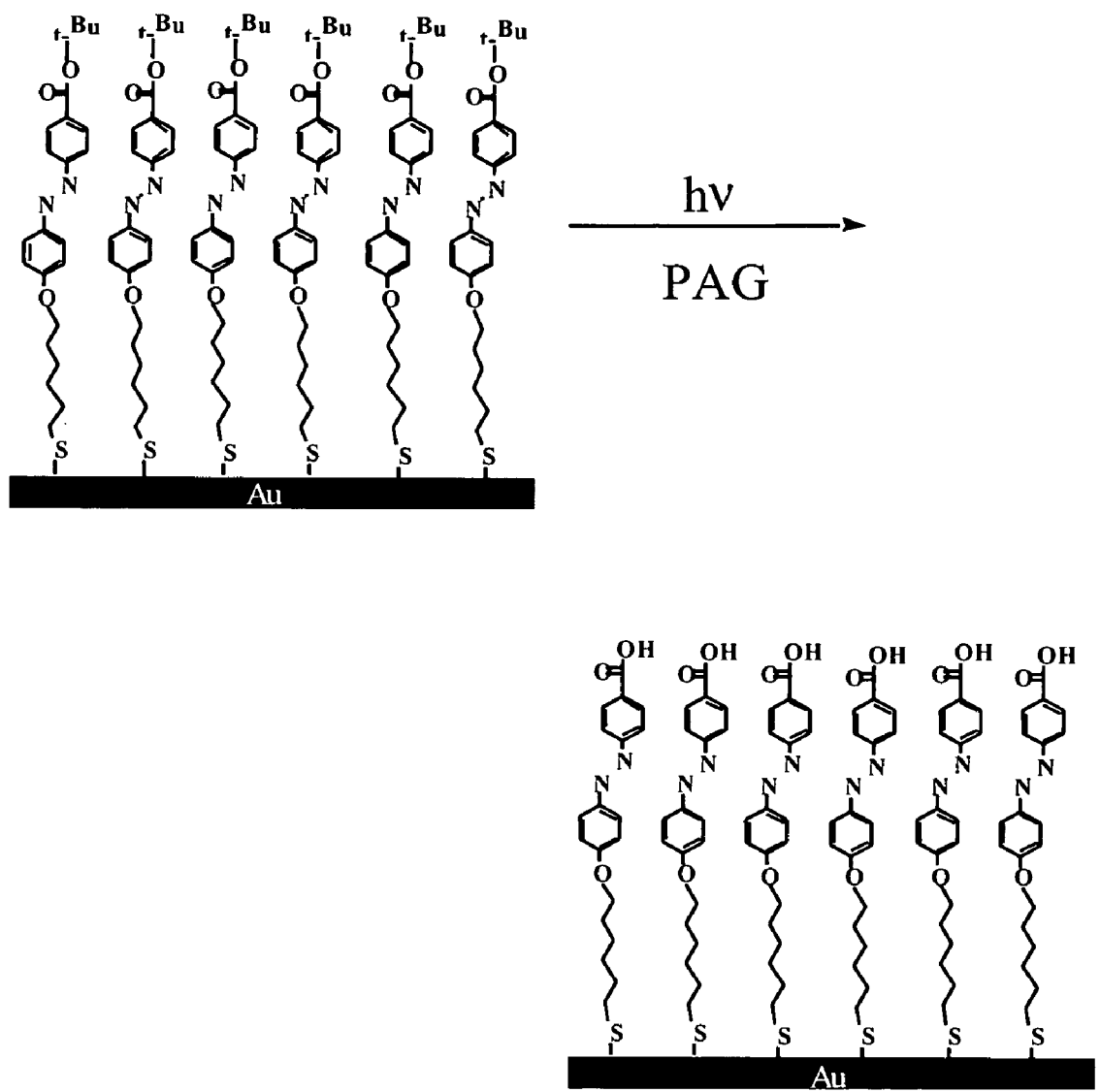
FIG. 12 shows the self-assembly of t-butyl-substituted azobenzene alkanethiol derivatives followed by UV exposure.

The photochemical transformation reaction of FIG. 11 is useful to modify surface properties when confined to a surface. For this purpose, the azo compound is functionalized at its other terminus with an alkane thiol group in order to promote self-assembly at the surface of coinage metals such as gold. Self-assembly of SAM-tBu causes the t-butyl ester group to locate at the SAM-air interface as depicted in FIG. 12. A layer of photoacid generator is then applied onto the SAM-coated gold substrate by spin coating (using polystyrene as a carrier). Exposure to UV light and subsequent stripping of the surface PAG-containing overlayer converts the initially hydrophobic surface covered with t-butyl groups to an hydrophilic surface covered with reactive carboxylic acid groups.

The SAMs represented in FIG. 12 were characterized by water contact angle measurements and XPS. The measured water contact angles were 98±2° for SAM 1 and 28±2° for SAM 2, confirming the expected change in hydrophilicity from hydrophobic tert-butyl end groups to hydrophilic carboxylic acid end groups.

Figure 13A:
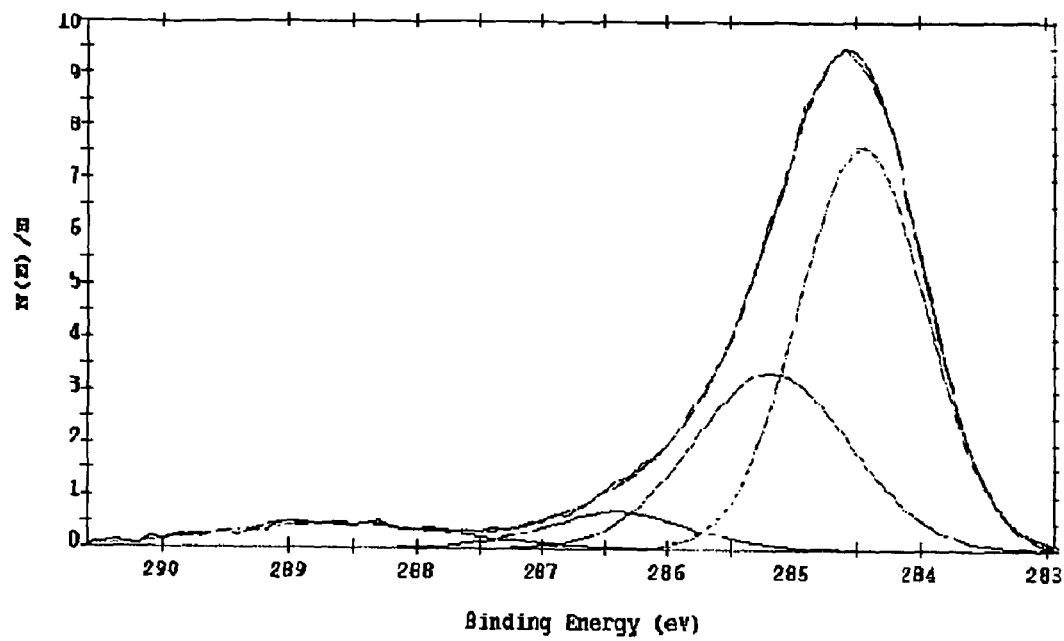
FIG. 13A and FIG. 13B are XPS spectra for t-butyl-substituted and acid-substituted azobenzene alkanethiol self-assembled monolayers.
Figure 13B:
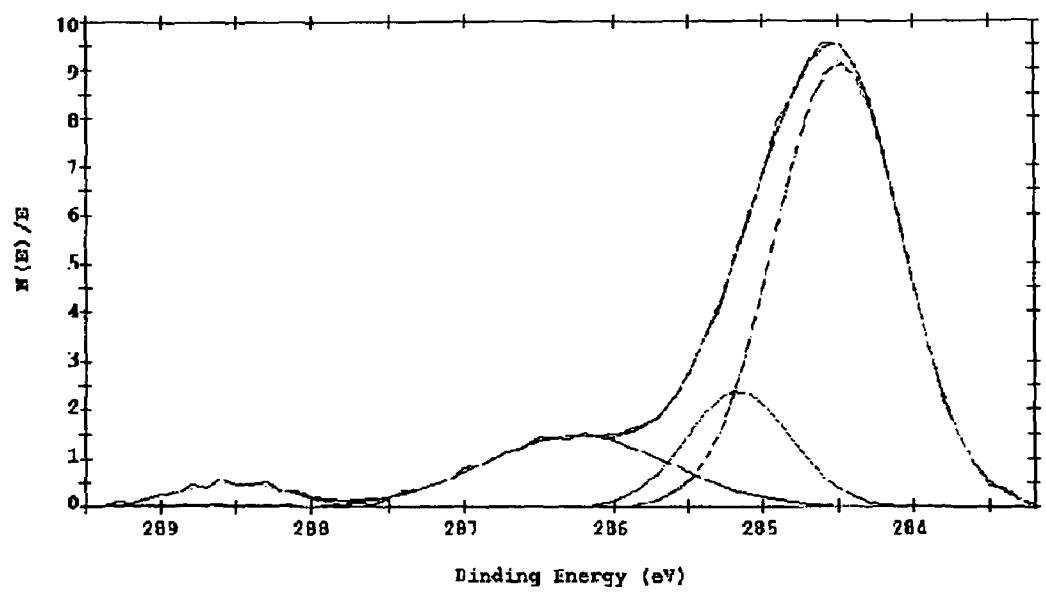

The XPS spectra shown in FIG. 13 provide quantitative confirmation of the photochemical surface modification reaction depicted in FIG. 12. The high-resolution C1s spectra for both the tert-butyl ester and photo-deprotected carboxylic acid surfaces show evidence of four different types of carbon. The signal at 284.6 eV is associated with aliphatic and aromatic carbons that are not bonded to oxygen, the 285.7 eV signal is associated with carbons in ether linkages, the 286.8 eV signal is associated with the ester carbon in the tert-butyl group and the 288.7 eV signal is associated with the carbonyl ester carbon. The large loss of the signal at 286.8 eV (see FIG. 13A) confirms almost complete removal of the tert-butyl group after photo-deprotection.

XPS is also employed to confirm that the functional monolayers are oriented normal to the surface as picture in FIG. 12 through analysis of the integrated peak intensities associated with each carbon type. The C1s peaks at 288.7 eV, 286.8 eV, 285.7 eV and 284.6 eV have an intensity ratio of 1:1:3:14 for SAM 1(a) and 1:2:3:17 for SAM 2(b). These values cannot however be interpreted directly because XPS is an integral technique. The signal for a particular spectral peak is related to the integral of the composition depth profile of the associated carbon atom weighted by the probability of escape for the corresponding ejected photoelectron. This relationship is given by [Andrade J. D., in Surface and Interfacial Aspects of Biomedical Polymers CH. 5, Plenum Press, New York, 1985]:

$$I_i(\theta) = K_i \int_0^\infty N_i(x) e^{-x/\lambda \sin\theta} dx \quad (1)$$

where $\theta$ is the photoelectron takeoff angle, $K_i$ is a constant for carbon type i, $\lambda$ is the photoelectron mean free path and $N_i(x)$ is the composition depth profile of carbon type i. Knowledge of the composition depth profile, $N_i(x)$, is therefore necessary in order to correctly calculate the ratios of different carbon signals. The atomic distribution functions, $N_i(x)$, were estimated by applying to model the SAMs in an all-trans extended conformation oriented perpendicular to the substrate. Once the positions of each atom were calculated, equation (1) was applied to calculate the XPS signals of each individual carbon in the SAMs. The total carbon, nitrogen and oxygen signals calculated in this fashion and summed over all atoms are reported in Table 1, where they are compared to experimentally determined atomic percentages. The nitrogen signals do not compare well, however these are weak signals due to the low intrinsic photoelectron yield for nitrogen and are subject to large errors. The carbon and oxygen signals predicted by the molecular model assuming normal orientation agree well with the experimental values, supporting the hypothesis that molecules within the SAMs are oriented normal to the substrate.

Monolayer thickness is estimated through ADXPS by systematically varying the photoelectron takeoff angle. SAM thickness was evaluated by measuring the ratio of signals originating in the overlayer (C1s) and the substrate ($Au4f_{7/2}$) as a function of take-off angle and regressing these data to the uniform overlayer model. The XPS-estimated thicknesses values agree well with values for similar azobenzene SAMs measured by X-ray reflectivity and ellipsometry and are comparable to the theoretical thickness, (see Table 1), 2.16±0.30 nm, obtained by modeling the molecular structure from known bond lengths. The thickness data indicate that the azobenzene SAMs possess a molecular orientation that is essentially normal to the substrate, consistent with the high packing density, molecular order, and stability provided by π-π interactions of the azobenzene unit. An orientation slightly tilted from the normal orientation was previously found for other aromatic thiol monolayers on Au(111). In this case, the molecular orientation was deduced from a comparison of experimental and theoretical thickness data.

TABLE 1

XPS determination of elemental composition at a 45° take-off angle and ADXPS estimated thicknesses (t) of SAM 1 and SAM 2

|  |  | C(%) | O(%) | N(%) | t(nm) |
|---|---|---|---|---|---|
| SAM 1 | Theory[a] | 81.9 | 11.5 | 6.64 | 2.13 |
|  | Experiment[b,c] | 82.8 | 12.6 | 2.2 |  |
| SAM 2 | Theory[a] | 77.0 | 14.7 | 8.31 | 2.10 |
|  | Experiment[b,c] | 79.3 | 15.7 | 3.6 |  |

[a]The theoretical value of the elemental composition is calculated from the molecular structure
[b]The uncertainty of the abundant elements C and O is ±5%
[c]The uncertainty of the trace element N is ±15%

The XPS and contact angle analyses confirm that t-butyl-terminated azobenzene alkanethiols self-assemble onto gold substrates in a nearly normal orientation, and that the surface of these SAMs can be converted from hydrophobic tert-butyl groups to hydrophilic carboxylic acid groups by exposure to UV light in the presence of a photoacid generator.

Figure 14:
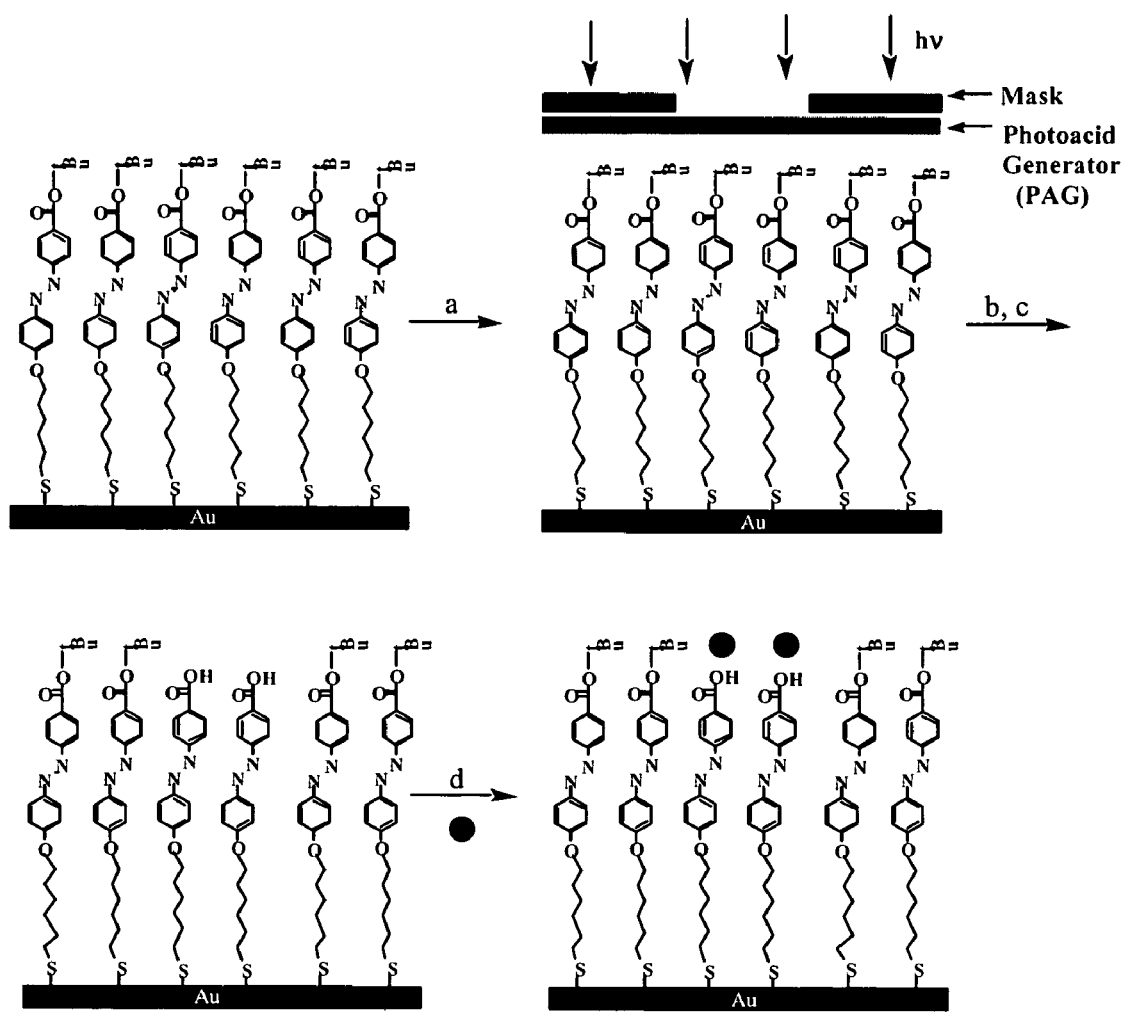
FIG. 14 is a schematic of photochemical modification of a SAM surface.

Photochemical surface modification can also be adapted to chemically pattern SAM surfaces. FIG. 14 shows how the surface of SAM 1 photochemically modified to create a heterogeneous pattern of hydrophobic and hydrophilic regions [*Langmuir* 1994, 10, 626]. End-functional azobenzene alkanethiols are self-assembled onto a gold substrate and then coated with a layer of PAG supported in polystyrene by spin coating. The surface is subsequently covered with a patterned photo-mask and irradiated with UV light. Unmasked regions on the surface are photodeprotected to form carboxylic acid terminated regions, while unexposed regions retain t-butyl functionality. The resulting heterogeneous surface serves as a template for the subsequent deposition of a variety of objects and ligands into patterns with microscale resolution.

Figure 15:
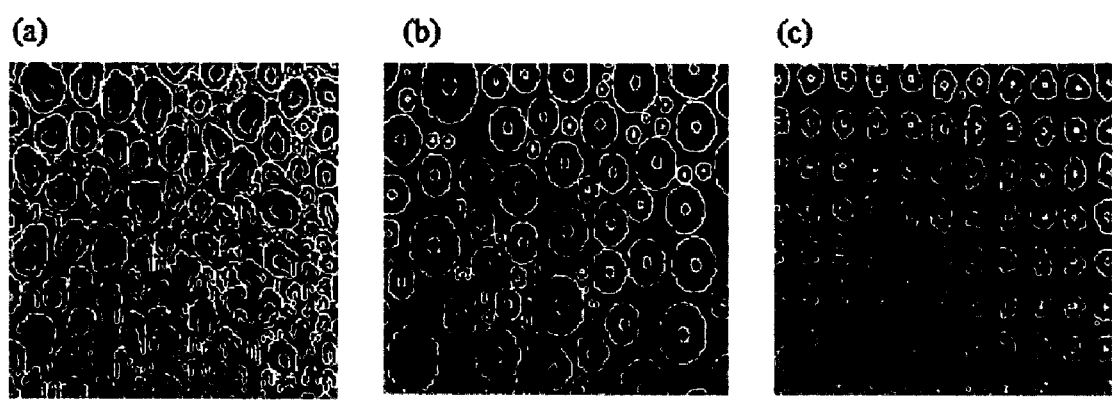
FIG. 15 compares images of the hydrophobic SAM 1 surface, the hydrophilic SAM 2 surface, and the patterned SAM surface visualized by exposure to water vapor.

Surface patterns generated by the photochemical surface modification technique can not usually be observed by eye, since the modifications involved generally do not produce large changes in thickness or refractive index, but they can be observed using a variety of visualization techniques. FIG. 15 compares images of the hydrophobic SAM 1 surface (a), the hydrophilic SAM 2 surface (b), and the patterned SAM surface (c) visualized by exposure to water vapor. In (a), macrosopic water droplets condense and bead up on the hydrophobic tert-butyl-ester terminated monolayer surface (shown previously to have a water contact angle of 98 degrees). In (b), the water droplets are again macrosopic, but partially wet the substrate (with a contact angle of 28 degrees). In (c), a well-ordered microscale array of water droplets is observed as water vapor preferentially condenses onto the more hydrophilic carboxylic acid functional sites produced by exposure through the mask. The masked tert-butyl-ester terminated regions act as hydrophobic dams that restrict water to spread only onto the photodeprotected carboxylic acid regions.

Figure 16:
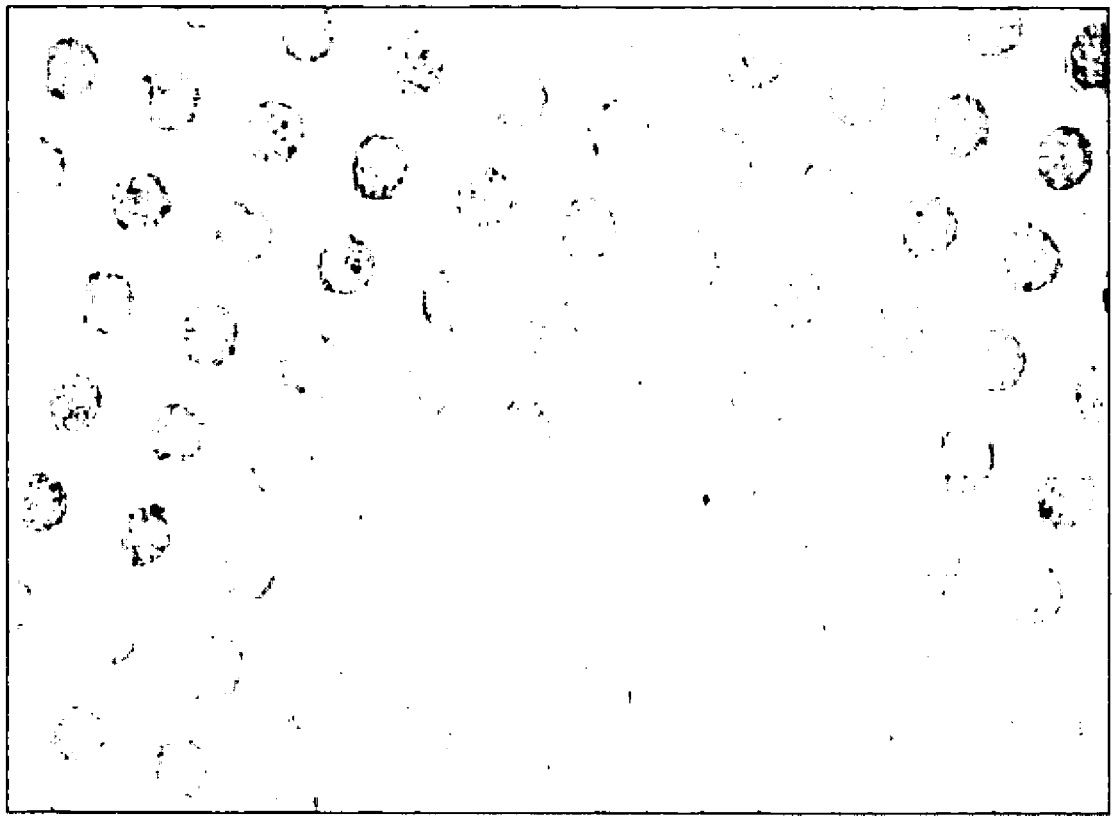
FIG. 16 is an optical microscope image showing selective adsorption of PS-NH$_2$ colloidal particles.

Photochemically patterned surfaces are also visualized by using them to template the adsorption of a variety of ligands. Ligands are templated through either hydrophilic interactions with tert-butyl functionality or hydrophobic interactions with the carboxylic acid functionality. A suspension of amine functionalized polystyrene ($PS-NH_2$) colloidal particles (3 μm diameter) in an aqueous solution was prepared and deposited on a surface patterned with a 100 μm TEM grid. The optical microscope image shown in FIG. 16 demonstrates that the $PS-NH_2$ colloidal particles selectively adsorb onto UV-exposed regions patterned with surface carboxylic acid groups by nature of acid-base interactions.

Figure 17:
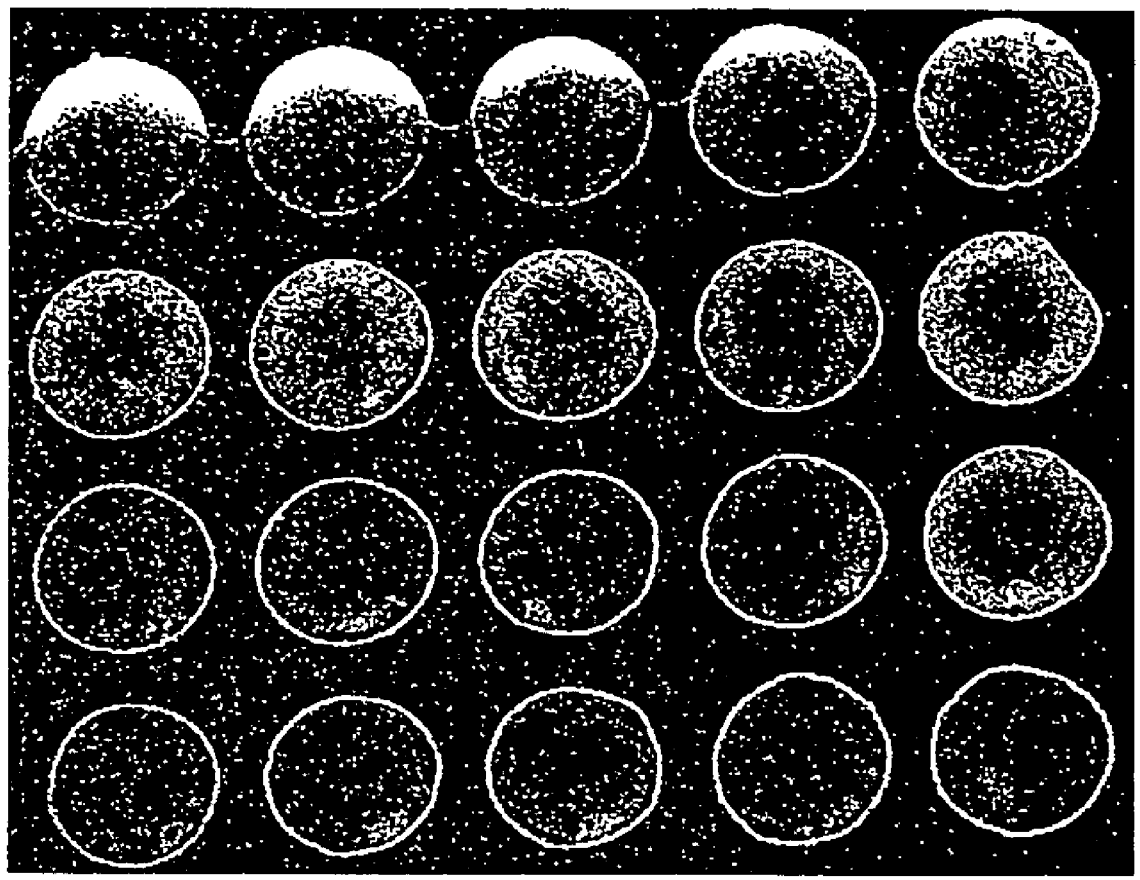
FIG. 17 is a fluorescent confocal microscope image of a PS-fluorescent estimated surface.

PS-fluorescent labeled nanoparticles (56 nm) were ligated to the photochemically patterned surface. FIG. 17 shows a fluorescent confocal microscope image of the decorated surface, confirming that the nanoparticles deposited selectively on carboxylic acid regions on the surface.

EXAMPLE 4

Surface Micropatterning of Biomolecules Through Photolithography on Block Copolymer Polymer Brushes PS-b-PtBA was coated on PS as described in Pan et al., *Polymer Preprints* 2003, 44(1), 500.

ADXPS was used to quantitatively estimate the top PtBA layer thickness assuming a bilayer model of polymer brush system due to a layering effect caused by microphase separation of two incompatible blocks in PS-b-PtBA block copolymer. To calculate, $$I \propto \int N\exp\left(\frac{-x}{\lambda\sin\theta}\right)dx \Rightarrow$$

$$\frac{I(\text{C\_shifted})}{I(\text{C\_total})} \equiv \frac{\frac{N1}{7}\int_0^d \exp\left(\frac{-x}{\lambda\sin\theta}\right)}{N1\int_0^d \exp\left(\frac{-x}{\lambda\sin\theta}\right) + N2\int_d^\infty \exp\left(\frac{-x}{\lambda\sin\theta}\right)} \Rightarrow R(\theta) =$$

$$\left(\ln\left(\frac{1 - 7\frac{I(\text{C\_shifted})}{I(\text{C\_total})}}{1 + 7\frac{I(\text{C\_shifted})}{I(\text{C\_total})}\left(\frac{N2}{N1} - 1\right)}\right)\right) = \frac{-d}{\lambda\sin\theta}$$

where k is the instrumental factor, λ is photoelectron attenuation length, θ is the ADXPS take-off angle, and N is the elemental number density.

Figure 18:
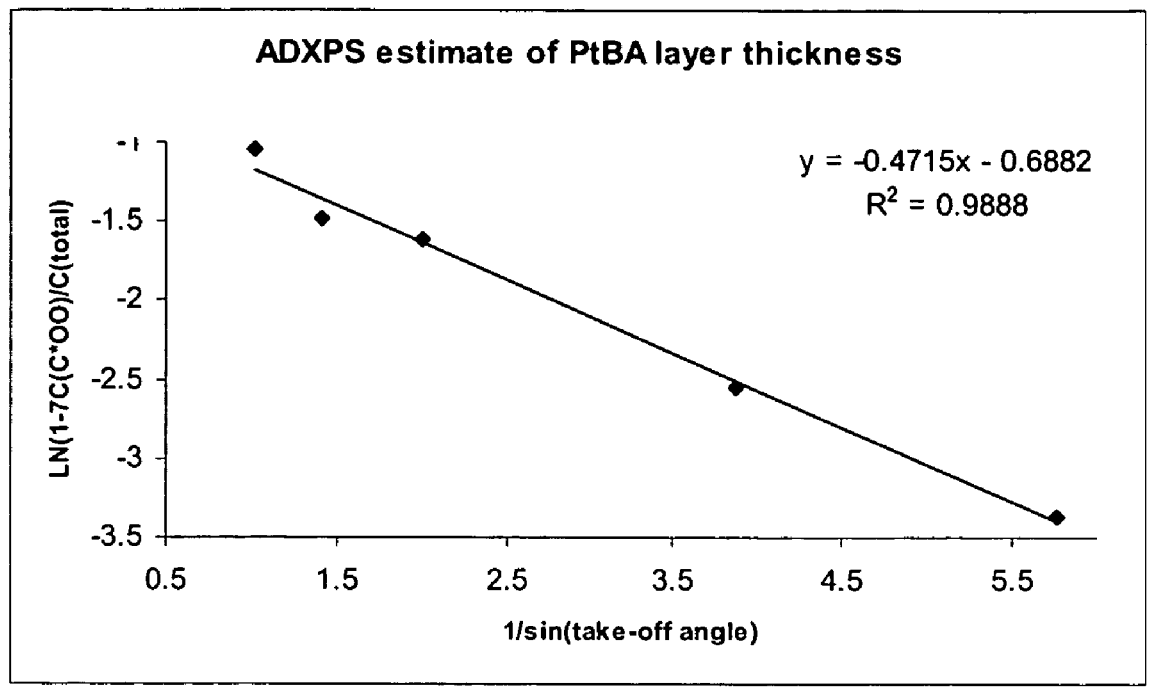
FIG. 18 is a plot of R($\theta$) vs. 1/sin $\theta$ which gives the angle dependent XPS estimated thickness of a PtBA layer.

Based on a plot of R(θ) vs. 1/sin θ as in FIG. 18, the ADXPS estimated thickness of the top PtBA layer of unannealed PtBA-b-PS/PS brush is λ×0.47=3.55 nm×0.47=1.67 nm, where λ is taken from *J. Phys. Chem.*, 1989, 93, 1670. The thickness so measured provides a rough estimate of the top layer thickness.

Figure 19:
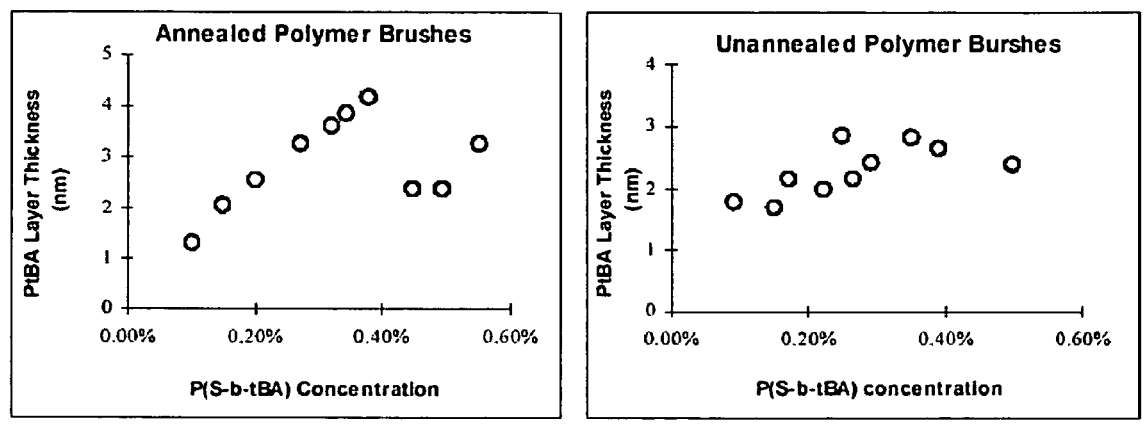
FIG. 19 shows the estimated PtBA layer thickness as a function of polymer concentration of diblock copolymer for annealed and unannealed films.

The thickness of film obtained by spin coating is controlled by varying the concentration of polymer solution. The film of the polymer brush is not in equilibrium immediately after spin coating, which means that the PtBA layer does not completely phase segregate from the diblock copolymer. The annealing process brings this system closer to equilibrium faster. An annealing temperature of 110° C. is used, which is slightly above $T_g$ for both PS ($T_g$~100° C.) and PtBA ($T_g$~45° C.). The PtBA layer thickness was again calculated based on a bilayer model. FIG. 19 presents the estimated thickness of the PtBA layer as a function of polymer concentration of diblock copolymers for annealed and unannealed films. The thickness of PtBA layer of annealed brushes increases with the diblock copolymer concentration from 0.1% weight to 0.4% weight in a neat linear fashion. When the concentration is above 0.4% weight, the PtBA layer thickness drops and remains constant at around 2.2 nm. When annealed, low surface tension PtBA blocks segregate to the polymer/air interface on top of the polymer. At polymer concentrations below 0.4% weight, there is not enough material of PtBA to form a stable polymer monolayer. At the same time, the surface tension of PtBA is much less than that of PS, and there is a strong tendency for PtBA to spread completely on top of PS even to provide submonolayer coverage. The top PtBA layer thickness is determined solely by the amount of available PtBA, which is proportional to polymer concentration. When the polymer concentration is above 0.4% weight, there is more PtBA to form a saturated monolayer and may break into multilayer structure upon annealing. The radius of gyration of PtBA blocks is roughly 4.0 nm from the 0.4% weight inflection point based on this assumption. For unannealed polymer brushes, the PtBA blocks do not have the mobility to phase separate to the top of the film and remain kinetically frozen within PS blocks. This agrees with the experimental observation that the thickness of unannealed PtBA brushes remains roughly constant regardless of polymer concentration.

Figure 20:
FIG. 20 is an optical micrograph of patterned polymer brushes of poly(t-butyl)methacrylate-b-P S/PS.

Patterned polymer surfaces are observed by optical microscope. FIG. 20 shows an optical micrograph of patterned polymer brushes of PtBMA-b-PS/PS. The contrast results from the combined effect of thickness and mass density change between PtBMA and PMAA regions.

EXAMPLE 5

Surface Micropatterning on Thin Film of Polymer Brushes and Self-Assembled Monolayers of Azobenzene Alkanethiolate on Gold via Photolithograpy Surface patterning on solid substrates is of growing importance in surface engineering. Surface patterning refers to creating 2D spatially heterogeneous surfaces with different chemical functionality, hydrophobicity or morphology at well-defined regimes with micron or submicron feature sizes. It has application in thin film device fabrication for modern technology, particularly in microelectronics, information storage, optics and sensors.[1] Surface patterning also provides an excellent model surface system for theoretical study of surface-induced phase separation of thin film polymer blends and block copolymers[2,21], intermolecular surface forces between heterogeneous surfaces[3], object 2D self-assembly process[4], nucleation and crystallization[5], excess interfacial free energy[6]. Patterned surfaces can be used as universal templates to assist self-assembly and selective deposition of any object of interest including polymer and inorganic colloidal particles[4,7], nanoparticles[7c,8], photonic crystals[9] and biomolecules (DNA[10], protein[11], peptide and cell[12]) etc. There have been numerous demonstrations of surface patterning on different solid substrate (homopolymer[13], polymer brushes[14], hydrogel[15], self-assembled monolayers (SAMs)[16], LB films[17]) by different strategies (photolithography[18,14c,11d,e], μcp[19], laser ablation[8b,13a,20], X-ray irradiation[21], ion and e-beam direct writing[11c,22], mechanical[23] and other photochemical techniques[11a,24]).

Two novel approaches to pattern surfaces are shown. Surfaces of polymer brushes of PS-b-PtBA diblock copolymer physically grafted into a PS homopolymer melt matrix (termed as PtBA-b-PS/PS brush) and surfaces of tert-butyl terminated azobenzene alkanethiolate SAMs are patterned with different chemical functionality and wetting property (—COOH/CH₃) based on photolithography and used as a template to immobilize biomolecules at precise locations.

The approach to pattern polymer brushes and azobenzene SAMs of the present invention has a number of advantages. First, it is adaptable from mature microelectronic technology. Pattern feature resolution can be extended to the resolution of current commercial chips. Chemical amplification resist lithography techniques[25] improve the photolysis efficiency greatly and UV exposure time can be shortened to 10 seconds instead of the usual extreme long exposure times (4-12 hours) used in other photopatterning approaches[26]. Second, poly (tert-butyl acrylate) (PtBA) is known as a biocompatible photoresist[27]; water or ethanol is used as solvent in every step for biomolecules immobilization, which is completely tolerable by biomolecules; UV exposure and residue photoresist removal are both carried out before biomolecules immobilization. These features minimize the risk of reducing biological reactivity and make the technique desirable for patterning biomolecules. Well-defined and reliable photochemistry[28] opens more opportunity of selective physisorption and covalent bonding of external ligands. In contrast, existing surface modification of polymer and SAMs achieved either by UV, X-ray, laser, plasma, ion and e-beam irradiation or strong chemical oxidation brings inhomogeneous, multiple functional groups (—OH, —C=O—H, —COOH, etc) to the surface[29,21] reducing the selectivity for subsequent derivatization. Finally, the technique has wide applicability due to its easiness and universality. This polymer brush pattern strategy, when used to pattern biomolecules, also overcomes the limitation of low surface density of immobilized biomolecules of reactive μCP on patterning biomolecules on polymers[13c], and also removes the limitation of susceptibility to UV light for photochemical approaches based on molecules with photolabile groups[11a].

Two patterning approaches to introduce surface functional groups (tert-butyl ester groups) are used for photo-hydrolysis. Surface tert-butyl ester groups are either from surface segregation of surface-active PtBA block in PS-b-PtBA block copolymer in polymer brush or from terminal group of an azobenzene in SAMs. Surface patterns of polymer brush are confined to the topmost monolayer by controlling the top PtBA layer of polymer brushes within monolayer thickness.

XPS is used to monitor the change of surface chemistry and water contact angle measurement is used to monitor change of surface wetting property. Angle dependent XPS is used to measure the thickness of top PtBA layer in polymer brushes and azobenzene SAMs.

DUV Photolithography technique is used to pattern the surface. Briefly, the photogenerated acid is formed upon DUV exposure and cleaves the tert-butyl groups at well-defined regimes to form —COOH/—CH$_3$ surface pattern. Fluorescence imaging and water condensation imaging are used to image the surface pattern in this proposal. SEM and XPS imaging are also useful as imaging techniques.

A patterned surface is also useful as a template to assist selective deposition of other external ligands for industry applications and for fundamental theoretical surface studies.

Materials

All materials and chemicals were used as received unless stated otherwise. Carboxylic acid and tert-butyl terminated azobenzene self-assembled monolayers, HS—(CH$_2$)$_6$—O—C$_6$H$_4$—N=N—C$_6$H$_4$—COOH (SAM-azo-COOH) and HS—(CH$_2$)$_6$—O—C$_6$H$_4$—N=N—C$_6$H$_4$—COO—C(CH$_3$)$_3$ (SAM-azo-tBu) were synthesized in our lab, as above. PS (MW=250K) was purchased from Acros Organics Inc. PS(200K)-b-PtBA(200K) was purchased from Polymer Source Inc. Triethoxy-terminated PS (MW=200K) was purchased from Scientific Polymer Inc. Coupling agents, 1-ethyl-3-(3-dimethylaminopropyl)carbodiimide hydrochloride (EDC) and N-hydroxysuccinimide (NHS) were purchased from Aldrich. Triarylsulfonium triflate, one kind of photogenerated acid (PAG) is a generous gift from IBM. Solvents including toluene (99.5% purity) and propylene glycol methyl ether acetate (PGMEA, 99% purity) were purchased from Aldrich. Ethanol (200 proof, absolute) was purchased from Pharmco Products. Inc. Organic dyes and fluorescent-tagged biomolecules were purchased from Molecular Probes Inc., including 4,4-difluoro-1,3,5,7-tetramethyl-4-bora-3a, 4a-diaza-s-indacene-8-propionic acid, succinimidyl ester (BODIPY® 493/503, SE, referred to herein as Bodipy-ester), 4,4-difluoro-5,7-dimethyl-4-bora-3a,4a-diaza-s-indacene-3-propionyl ethylenediamine, hydrochloride (BODIPY® FL EDA, referred to herein as Bodipy-NH$_2$), N-(2-aminoethyl)biotinamide, hydrobromide (biotin ethylenediamine, referred to herein as Biotin-NH$_2$), Alexa488 tagged Streptavidin (Alexa488-Sreeptavidin). Fluorescein-5 isothiocyanate tagged Bovine serum albumin (FITC-BSA) is a generous gift from Professor Robert Prud'homme in Princeton University.

Contact Angle Measurement

Sessile drop water contact angle measurement was carried out at room temperature with a model 100-00 contact angle goniometer (Rame-Hart, Inc.). The contact angles were recorded immediately after dispensing 1 μL water droplets with a pipette onto the surface. The reported values were average values of measurements of more than 3 different samples at more than 3 different spots for each sample. Contact angle titration[40] was carried out by measuring contact angles of 1 μL droplet with known pH ranging from 2-13. The pH of aqueous solution for titration was adjusted by adding NaOH or HCl till the desired pH value is reached.

X-ray Photoelectron Spectroscopy (XPS)

XPS spectra were recorded with PHI 5500 model Spectrometer equipped with a Al Kα monochromator X-ray source run at 15 kV and 23.3 mA, a hemispherical electron energy analyzer, a multichannel detector. The test chamber pressure was maintained below $2 \times 10^{-9}$ torr during the spectra acquisition. Low energy electron flood gun was used to neutralize the possible surface charge. The XPS Binding energy (BE) was internally referenced to referenced to aliphatic main C1s peak (BE=284.6 eV). Survey spectra was acquired at an analyzer pass energy 93.9 eV and BE resolution 0.8 eV, while high resolution spectra was acquired with a pass energy of 23.5 eV and BE resolution 0.05 eV.

The take-off angle is defined as the angle between the surface normal and detector. Angle dependent XPS (ADXPS) was performed by rotating the sample holder to the desired take-off angle by a motor. Spectra curve was fitted by a Gaussian-Lorentz function after subtracting a striped background using the PHI data processing software package under the constraint of setting reasonable BE shift and characteristic full width at high maximum range. Atomic concentration was calculated by normalization of the peak area to the elemental sensitivity factor data provided by PHI database.

Fluorescence Microscope

Fluorescence imaging of surfaces was carried out using Olympus IX70 laser scanning confocal microscope equipped with Ar laser as excitation source. Fluorescence was excited at 488 nm and emission intensity was collected above 510 nm after passing through a 510 nm bandgap filter. Fluorescence intensity was monitored as a function of X-Y position as the sample was focused above laser beam through 20× or 10× objective. Fluorescence image (512×512 pixels) was typically acquired at PMT voltage 900v and a scan speed of 16 second per scan.

Reflection Mode Optical Microscope

Light micrograph was recorded from Nikon OPTIPHOT metallurgical darkfield microscope equipped with a Kodak MDS digital camera in the reflection mode. The image was acquired using 20× and 5× objective.

Water Condensation Imaging

Ordered array of water droplets were condensed at the hydrophilic surface —COOH sites either by quickly giving a breath from mouth onto the cold sample surface, or by placing the sample (patterned surface upside down) above a few drops of DI water which are slightly heated at 50° C. to help evaporating the water upward and then condense into droplets once encountering the top cold sample surface.

Polymer Brush Surface Pattern Formation and Pattern Imaging

Polymer Brush Substrate Preparation

Glass substrates (coverslip or slides) were cleaned by etching a layer off from NaOH/H$_2$O/Ethanol mixture (1:1:8 w/w) in 10 minutes rending very hydrophilic surface[30] (water contact angle <5°). A layer of PS (MW=250K) or triethoxy-terminated PS (MW=200K) was spin coat (2000 rpm, 1 minute) from a solution of 0.77% w/w PS in toluene onto cleaned glass substrate. A layer of PS(200K)-b-PtBA(200K) block copolymer was spun coat (2000 rpm, 1 minute) from a solution of 0.46% w/w polymer in toluene on top of PS/Glass substrate.

Photopatterning via Photolithography

A layer of PAG was spun coat (1000 rpm, 1 minute) on top of PtBA-b-PS/PS/Glass from a solution of PAG in ethanol (1.5% w/w). PAG/PS-b-PtBA/PS/Glass sample was placed under a hand held UV lamp and exposed to DUV (shortwavelength 254 nm, 760 μw/cm$^2$) for 5 minutes with photomask in contact with the sample on the top. If necessary, sometimes the UV exposed sample was postbaked at 100° C. from 30 seconds to a few minutes to facilitate the diffusion of photogenerated acid molecules and increase the tert-butyl group deprotection rate. The excessive PAG was washed away by ethanol and dried with N$_2$ flux.

Fluorescence Imaging Patterned Surface of Polymer Brushes

Sample with patterned surface was immersed into 10 μM solution of Bodipy-NH$_2$ or Bodipy-Ester in ethanol for overnight and then N$_2$ dried after taken out of solution.

Biomolecules Surface Immobilization

Immobilization of BSA-FITC was achieved by immersing surface-patterned polymer brush substrate into an ethanol solution of BSA-FITC (10 μM) for overnight, then dried in N$_2$ flux after taken out of the solution.

Biotin/Strepavidin-Alex488 pattern through amide covalent linkage is a multi-step derivatization procedure. First the carboxylic acid sites of the surface-patterned polymer brush substrate were activated by immersion into a DI water (Resistance=18.2 MΩ) solution of EDAC (0.1 M) and NHS (0.2M) for an hour. Then the biotin-NH$_2$ ligand was covalently bound to the activated surface COOH sites through an amide linkage by immersion the COOH-activated surface-patterned polymer brush substrate into an ethanol solution of Biotin-NH$_2$ (10 mM) for an hour. The samples were washed with DI water and ethanol. In the end the molecular recognition step between surface bound Biotin and Alexa488 labeled streptavidin was achieved by immersion of Biotin-bound samples into an solution of 10 μM Alexa488-streptavidin in HEPES buffer (pH=7.4) which also contains 0.1% (w/w) BSA and 0.02% (v/v) Tween 20 detergent for 4 hours, then dried in N$_2$ flux after taken out of the solution and washed with HEPES buffer.

Azobenzene SAM Surface Pattern Formation and Pattern Imaging

SAM Substrate Preparation

Au substrates were prepared by evaporation of 100 nm of Au at high vacuum (p<10$^{-6}$ torr) onto polished Si single crystal wafers or glass slides which have been primed with 10 nm Cr or Ti layer to improve the adhesion of the Au films in Edwards Auto 306 thermal evaporator. SAMs were formed by immersing fresh Au samples into 1 mM solutions of SAM-azo-tBu in ethanol or THF for overnight in a cleanroom (Class 100). The SAM samples were stored in the cleanroom before use.

Photopatterning via Photolithography

A thick layer of PS containing PAG (7.9% w/w PAG w.r.t. PS) was spun coat (2500 rpm, 2 minutes) on top of SAM-azo-tBu from a solution of PS/PAG in PGMEA (7.2% w/w). This sacrificial PS/PAG layer is estimated more than 1 μm thick.

PS(PAG)/SAM-azo-tBu/Au sample was placed under a hand held UV lamp and exposed to DUV (shortwavelength 254 nm, 760 μw/cm$^2$) for 10-30 seconds with photomask in contact with the sample on the top.

UV exposed SAMs sample was postbaked at 100° C. from 30 seconds to 1 minute to facilitate the photogenerated acid molecules diffusion and increase the tert-butyl group deprotection rate.

The sacrificial layer of PS with excessive PAG was washed away by immersing into toluene for 30 minutes and then dried with N$_2$ flux after taken out of solution.

Characterization of polymer brush surface

Surface segregation of low surface energy, surface active block in diblock copolymer to free standing polymer/air interface in order to minimize the free energy is a well-known surface phenomena[31]. In diblock copolymer PS-b-PtBA, PtBA is the surface active block with low surface energy compared to PS block. Polymer brush of diblock copolymer tethering in the polymer melt chemically identical to one of the block in the copolymer has been extensively studied both theoretically and experimentally in the past[14a]. Chain architecture, grafting density, whole chain length, relative chain length and interaction energy between different blocks are all critical to the polymer brush structure and stability. Thin films of symmetric diblock copolymer self-organized into lamella microdomain with orientation parallel to the plane of the film[35]. The molecular weight of PS matrix melt (250K) and PS block (200K) in PS-b-PtBA block copolymer are larger than the critical entanglement MW (10.6K)[32] to improve the anchoring strength. The symmetric PS(200K)-b-PtBA (200K) diblock copolymer favors lamella morphology formation[53].

The polymer brush patterning procedure of Husemann et al. is followed[14c]. The spun coat polymer films self-assembly into bilayered or multilayered polymer brush and ADXPS is used to confirm the surface segregation of surface active PtBA block and estimate the top PtBA layer thickness based on a bilayer model. XPS Survey spectra of PS-b-PtBA/PS brush sample shows only C and O peak, as expected. The elemental composition of C and O is listed in Table 2 at various take-off angles. Since the O signal comes only from PtBA, the surface molar composition of PtBA and PS within the XPS sampling depth from O/C ratio is calculated according to:

$$O/C = 2*\phi_1(PtBA)/(9*\phi_1(PtBA) + 8*(1-\phi_1(PtBA))) \quad (1)$$

$\phi_1(PtBA)$ is the surface molar composition of PtBA calculated from O/C.

TABLE 2

ADXPS results on elemental composition (C and O) and composition of each C component with different chemical shift/environment.

| Take-off Angle | C | O | C*OO | COO—C* | C*—COO | C*(avg.) | φ1 (PtBA) | φ2 (PtBA) |
|---|---|---|---|---|---|---|---|---|
| 10° | 76.85 | 23.15 | 12.93 | 12.07 | 16.38 | 13.79 | 1.047 | 0.970 |
| 15° | 78.09 | 21.91 | 11.35 | 12.28 | 15.9 | 13.18 | 0.984 | 0.931 |
| 30° | 79.79 | 20.21 | 11.62 | 12.38 | 10.37 | 11.46 | 0.899 | 0.822 |
| 45° | 81.50 | 18.50 | 9.62 | 11.03 | 12.54 | 11.06 | 0.815 | 0.797 |
| 75° | 81.87 | 18.13 | 7.92 | 8.96 | 10.89 | 9.26 | 0.797 | 0.678 |

Note:
1) All the number in the table is percentage (%). C and O refers to % elemental composition, C*OO(BE = 288.8 eV), COO—C*(BE = 286.4 eV) and C*—COO(BE = 285.4 eV) refers to each C band % composition in total C.
2) C*(avg.) is the average value of 3 types of BE shifted C % composition in total C.
3) φ1(PtBA) is the surface molar composition of PtBA component calculated from C, O elemental composition. φ2(PtBA) is the surface molar composition of PtBA component calculated from BE shifted C*(avg.) composition in total C.

Figures 21A, 21B:
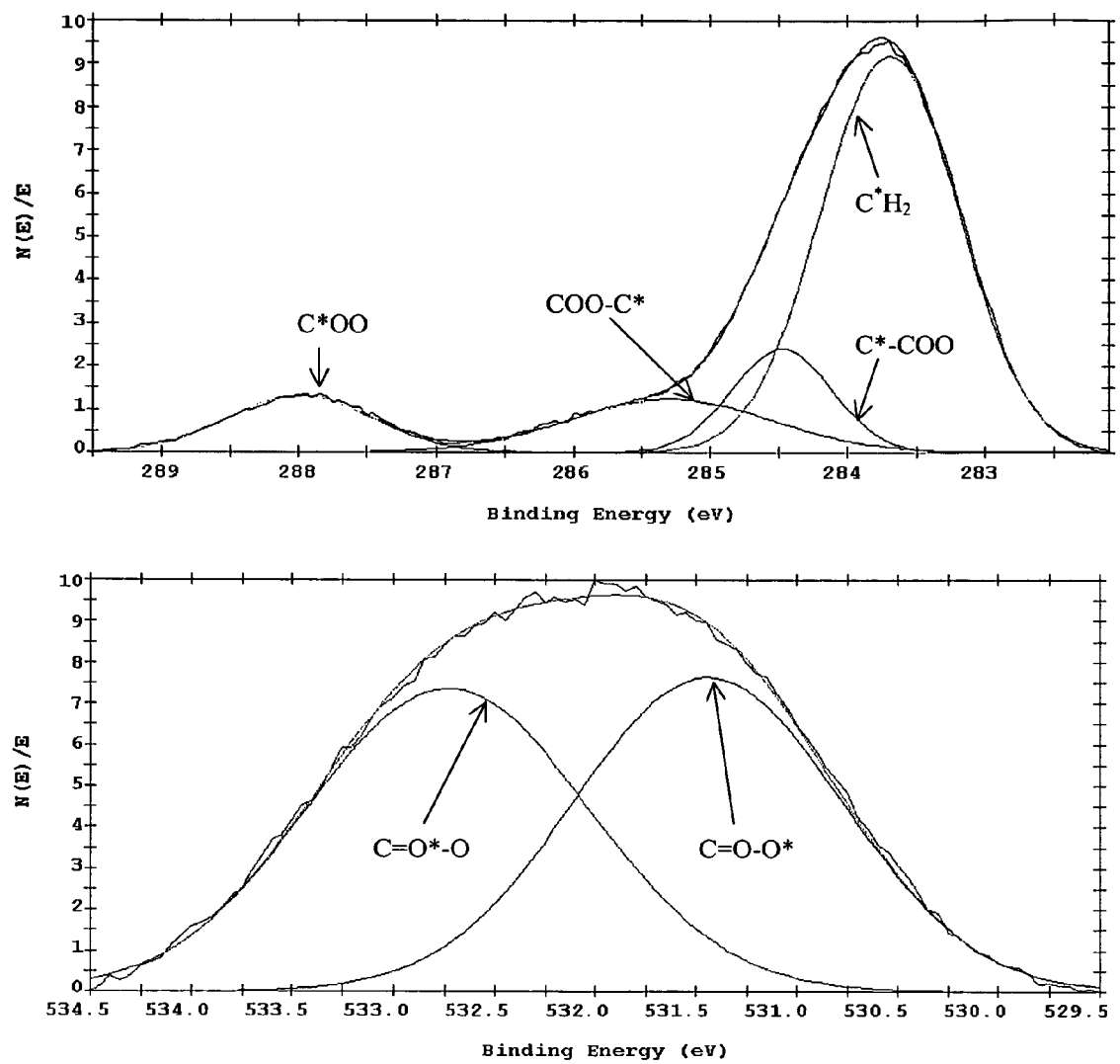
FIG. 21A and FIG. 21B are high resolution C1s XPS (FIG. 21A) and O1s XPS (FIG. 21B) of unannealed PtBA-b-PS/PS.

FIG. 21A shows the high-resolution C1s spectra with deconvoluted C subpeaks corresponding to C with different chemical environments. The peak centered around 288.8 eV (BE shift=4.0~4.2 eV) arises from carbonyl C (C*OO—), 286.3 eV (BE shift=1.6~1.8 eV) arises from ester C (COO—C*), 285.4 eV (BE shift=0.7~0.8 eV) arises from neighboring C to the carbonyl group (C*—COO). The peak positions and BE shifts all agree excellently with literature[33] and with C1s peak positions of spun-coat pure PtBA film. Chemical shift C is tabulated in Table 2. These are very close to 1:1:1 ratio as predicted from molecular structure of PtBA. Surface molar composition of PtBA is calculated from each type of BE shifted C(C*OO,C*—COO, COO—C*) composition of the total C. To reduce the uncertainty brought by curve fitting, the average C composition value of 3 types of BE shifted C to obtain surface molar composition of PtBA was used:

$$C(\text{avg. of BE shifted } C)/C\_\text{total} = \phi_2(\text{PtBA})/(7*\phi_2(\text{PtBA})+8*(1-\phi_2(\text{PtBA}))) \quad (2)$$

Figure 22:
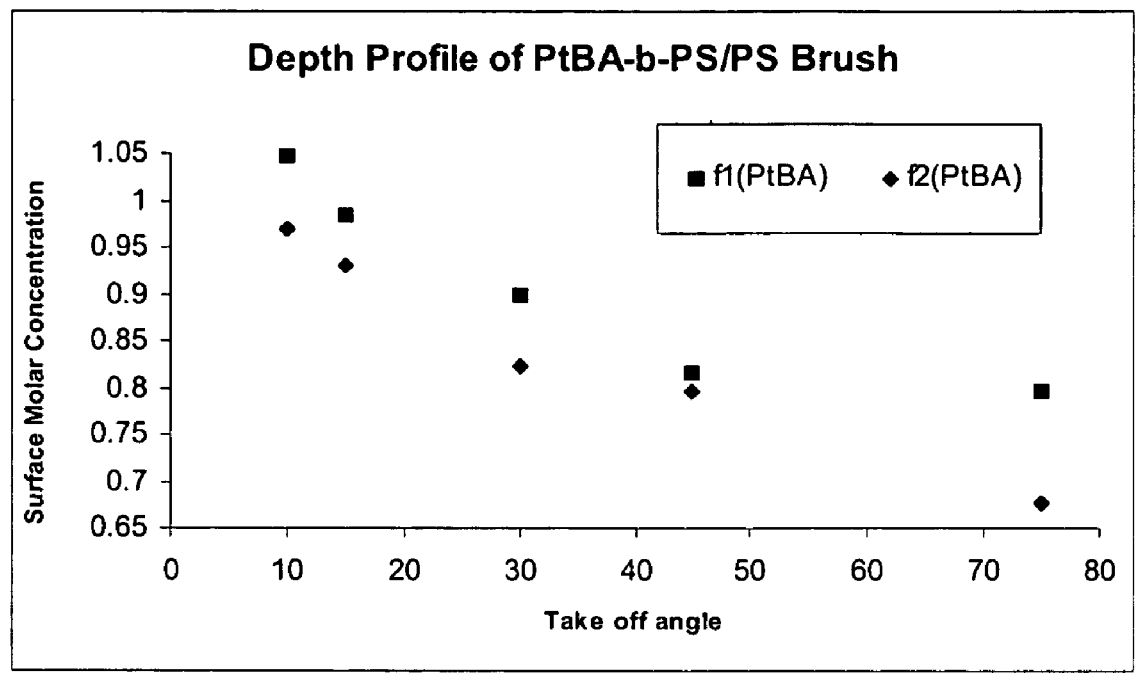
FIG. 22 shows the depth profile of PtBA-b-PS/PS brush.

$\phi_2$(PtBA) is the surface molar composition of PtBA calculated from C(avg.)/C_total $\phi_1$(PtBA) and $\phi_2$(PtBA) is compared in FIG. 22. $\phi_1$(PtBA) is consistently larger than $\phi_2$(PtBA) by 2~12% at all take-off angles. Taking into account possible surface contaminants which usually have more O content, $\phi_2$(PtBA) should be more accurate than $\phi_1$(PtBA). Both $\phi_1$(PtBA) and $\phi_1$(PtBA) show angle/depth dependent profile (FIG. 22), indicating the surface segregation of surface active PtBA block. High-resolution spectra of O1s (FIG. 21B) splits into two subpeaks with peak area ratio close to 1:1. The peak centered on 533.2 eV arises from carbonyl O (C=O*—O) while the other subpeak centers on 531.9 eV corresponds to ester O (C=O—O*). Peak position and 1-1.5 eV BE shift between them also agrees excellently with literature[33b,34]. The ADXPS estimated thickness is determined as in FIG. 18 above.

Figure 23:
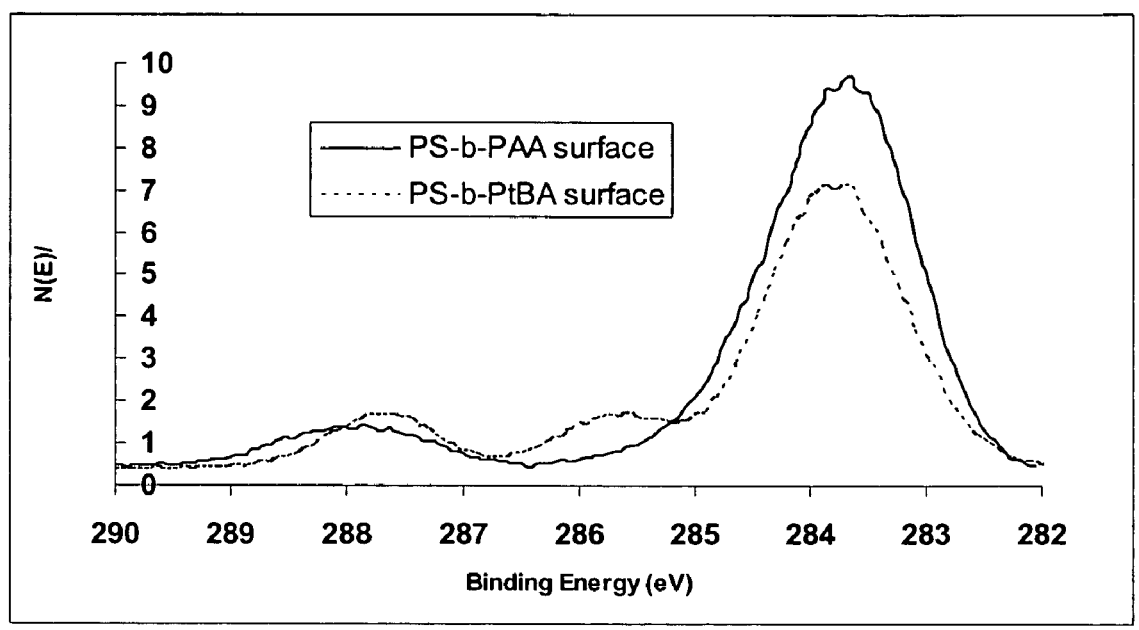
FIG. 23 is a high resolution XPS C1s spectra before and after photoacid deprotection of PtBA.

After photogenerated acid deprotects the tert-butyl ester group of PtBA, the original hydrophobic surface (θs=90° C.) becomes much hydrophilic (θs=35° C.) due to the exposed surface —COOH groups. After deprotection, the polymer surface is no longer smooth from optical microscope observation, due to the volume shrinkage of polymer brushes after PtBA brush is converted to PAA brush after deprotection.[14c,38] XPS C1s spectra (FIG. 23) also shows the disappearance of the intermediate ester C (COO—C*, BE~286.6 eV), which confirms the deprotection reaction.

Imaging of Patterned Polymer Brush Surface

Fluorescence imaging is a simple method for imaging surface patterns. The organic dyes selectively physisorb or chemisorb to specific surface region thus creating fluorescence patterning which is identical to the original surface pattern. Fluorescence contrast arises from mechanisms including hydrophobic interaction, electrostatic attraction, covalent bonding, and H bonding. Organic dyes with different terminal group were used to image complementary surface pattern through hydrophobic interaction and electrostatic attraction.

Figure 24A:
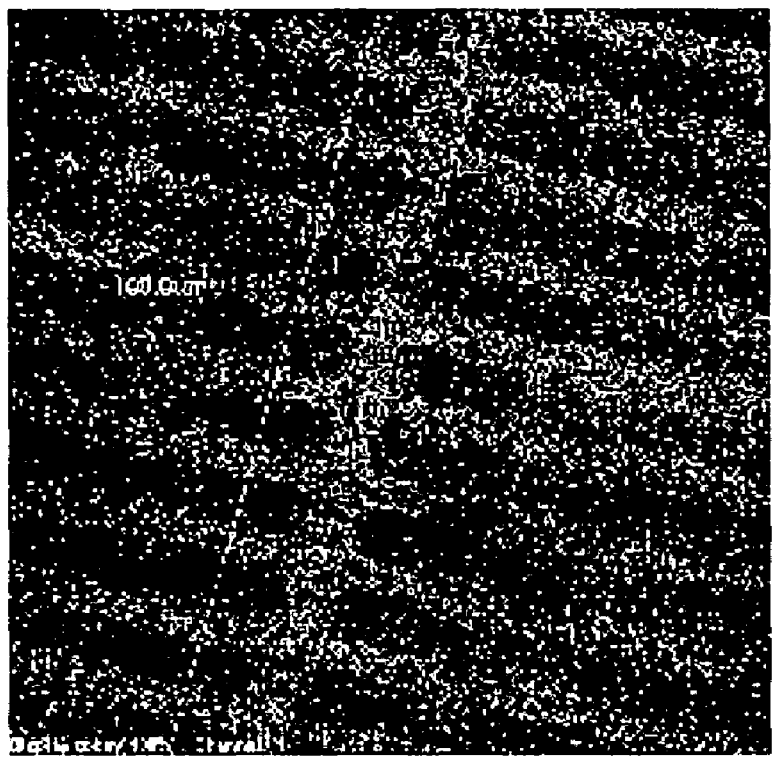
FIG. 24A and FIG. 24B show the preferential adsorption and fluorescence intensity line profile of Bodipy-ester on a photomask-protected surface.
Figure 24B:
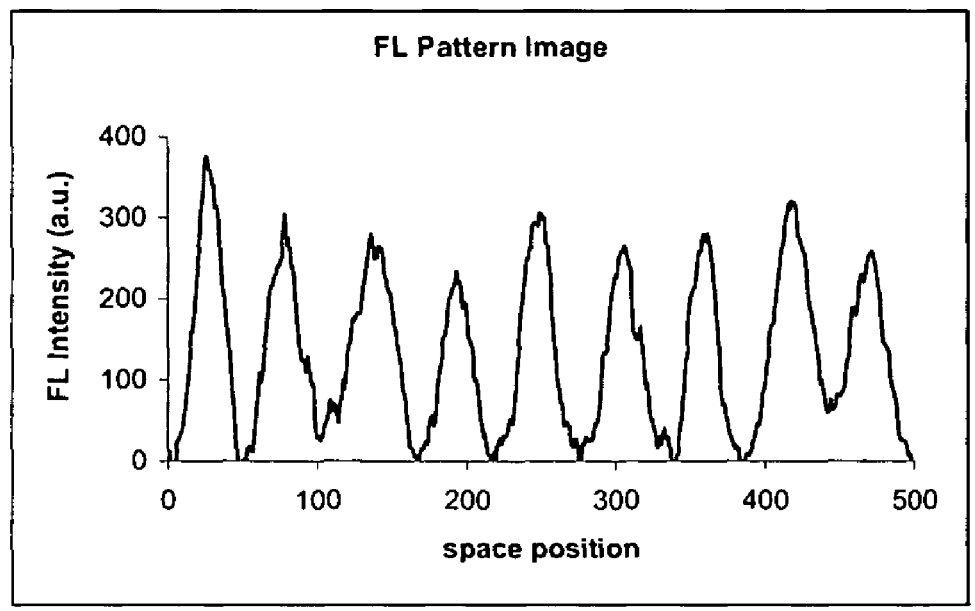
Figure 25:
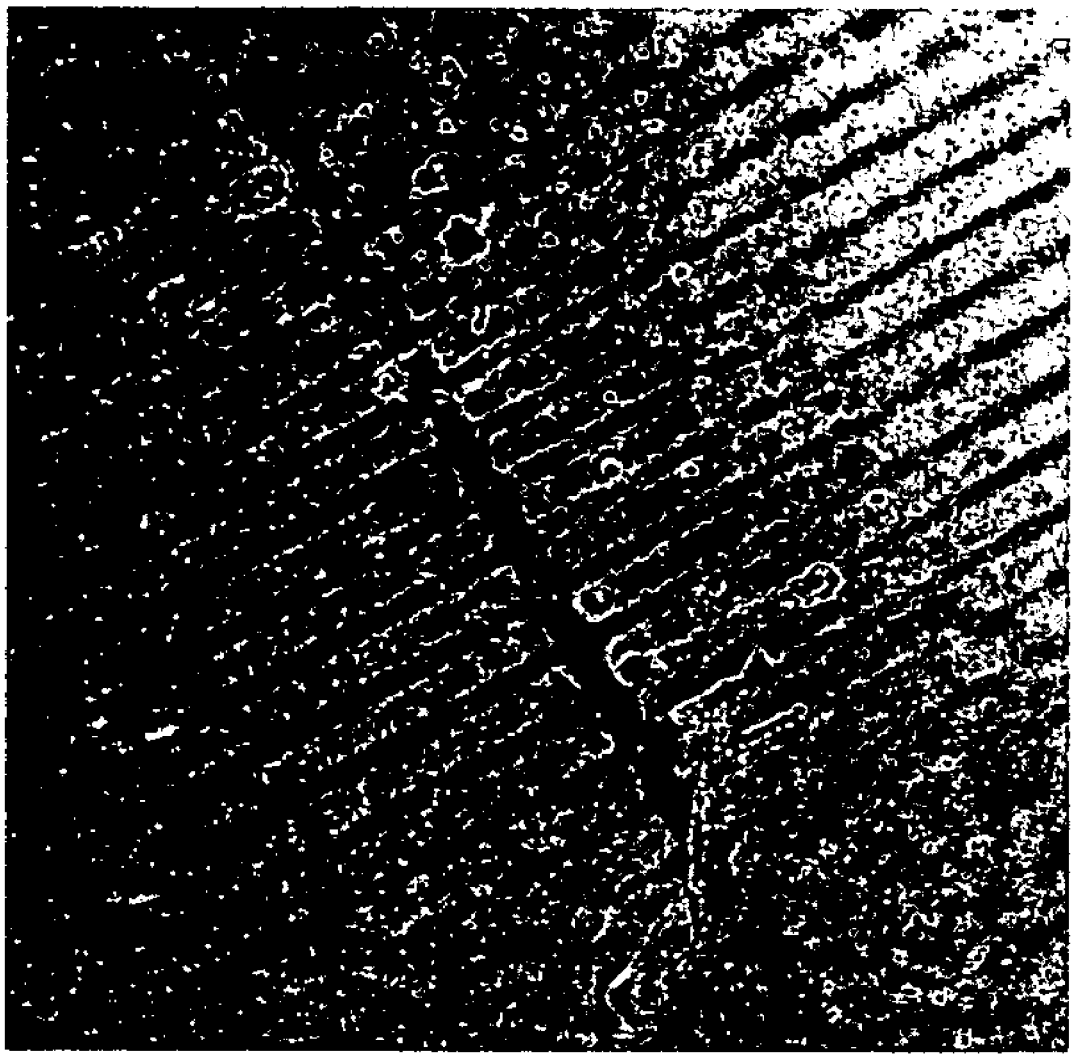
FIG. 25 shows the preferential adsorption of Bodipy-NH$_2$ on a photomask-protected surface.

FIG. 24A shows the surface pattern imaging by Bodipy-ester. The hydrophobic dye preferentially adsorbs to the original PtBA photomask region that is protected by photomask from UV exposure. FIG. 24B shows the fluorescence intensity profile of the line labeled in FIG. 24A. The fluorescence intensity spatial periodicity is 100 μm, the same as the photomask spacing. FIG. 25 shows the surface pattern imaging by Bodipy-NH$_2$. The dye was attracted to the UV exposed PAA region by electrostatic attraction between NH$_3^+$/COO$^-$ pair which is formed after one proton from the surface —COOH group transferred to the terminal NH$_2$ group in the Bodipy dye.

Figure 26A:
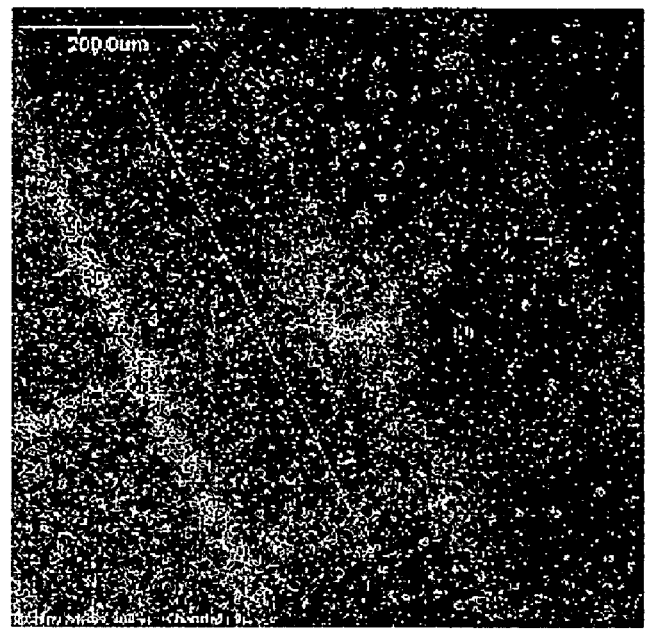
FIG. 26A and FIG. 26B show the preferential adsorption and fluorescence intensity line profile of BSA-FITC on a photomask-protected surface.
Figure 26B:
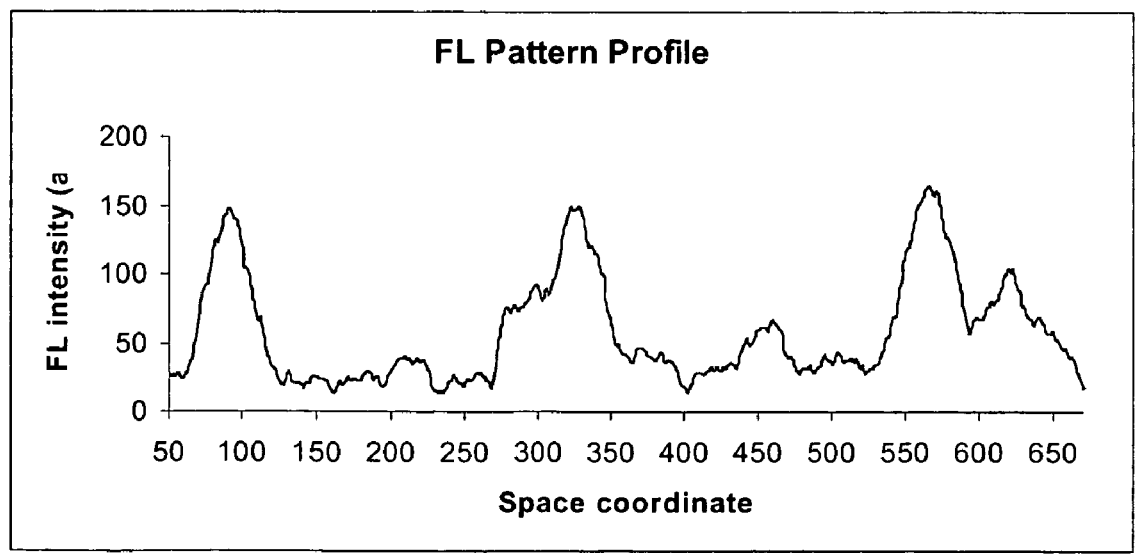

FIG. 26A shows the surface pattern imaging by BSA-FITC. The BSA-FITC protein preferentially adsorbs to the original PtBA photomask region from UV exposure. FIG. 26B shows the fluorescence intensity profile of the line labeled in FIG. 26A.

Characterization of Immobilized Biomolecules on Polymer Brush Surface

Figure 27A:
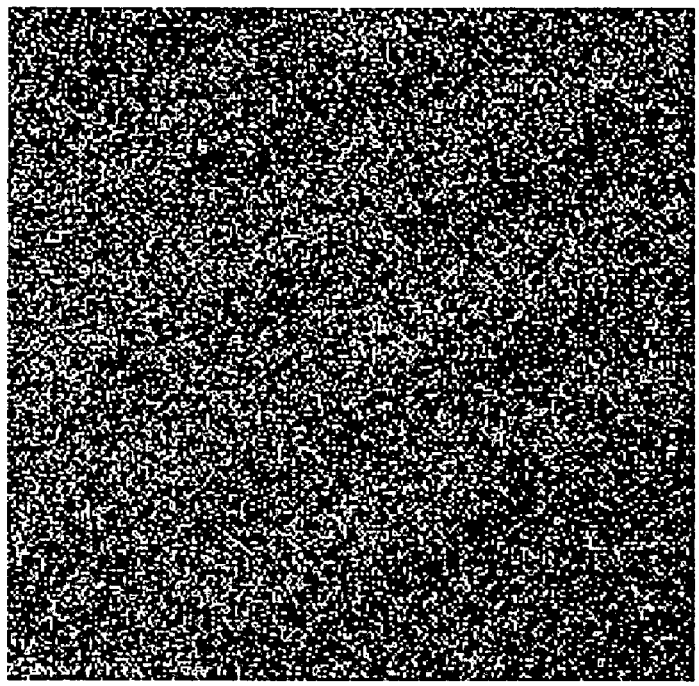
FIG. 27A and FIG. 27B show the preferential adsorption and fluorescence intensity line profile of Biotin-NH$_2$/Alexa488-Streptavidin on a photomask-protected surface.
Figure 27B:
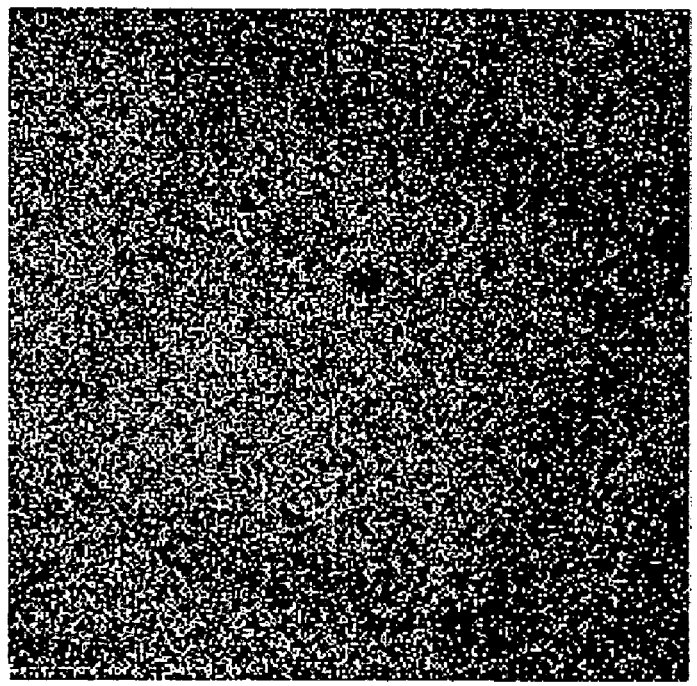
Figure 28:
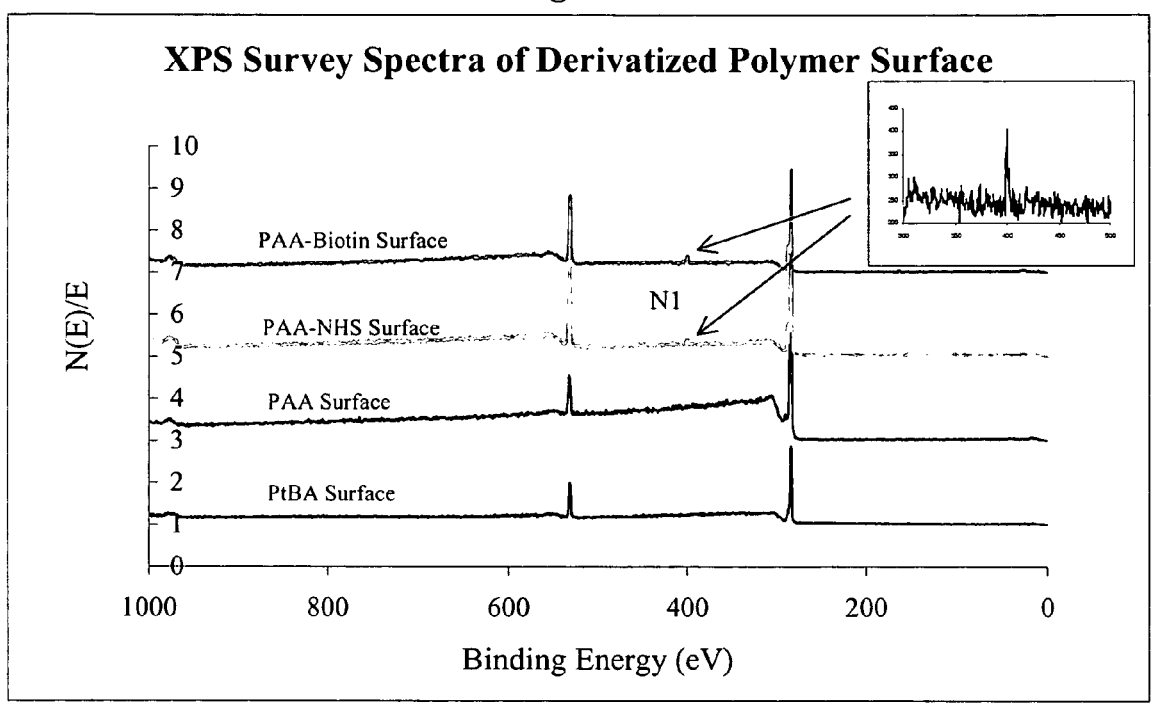
FIG. 28 shows XPS survey spectra of derivatized polymer surface.

Chilkoti et al.'s procedure was followed to pattern biotin and streptavidin[13f]. FIG. 27A and FIG. 27B show fluorescent imaging of the pattern of Biotin-NH$_2$/Alexa488-streptavidin bound to surface —COOH, using 100 μm spacing line photomask (FIG. 27A) or 250 μm×250 μm square photomask (FIG. 27B) for patterning. Each step of polymer brush surface derivatization was monitored by XPS (FIG. 28) and contact angle measurement (Table 3). The XPS results of elemental composition and reaction yield calculated from N/C ratio was also summarized in Table 3. The reaction yield was calculated for each stage of derivatization by comparison of experimental N/C ratio to theoretical N/C ratio assuming all reactive groups has been derivatized. For convenience the derivatized polymer surface are termed as surfaces of PtBA, PAA, PAA-NHS and PAA-Biotin at each stage. Activation of COOH sites of PAA by NHS-EDC mediation introduced a unique nitrogen peak from NHS in survey spectra. The nitrogen peak is also present in survey spectra after coupling to Biotin-NH$_2$ to the NHS/EDC activated PAA surface, but the N1s peak position shifted from 402.2 eV to 401.1 eV. The N signals centered at 402.2 eV agrees with the more electron-withdrawing nature N in NHS[39], and the lower BE (401.1 eV) N1s is also in accordance with the N present in Biotin. The contact angle change (Table 3) of derivatized polymer surface also confirms the success of reaction at each step. The N/C ratio was used instead of N/O or O/C to estimate the reaction yield because N is only present after the activation and amidation reaction and surface contaminants are of high O content, which will overestimate the O atomic composition. The theoretical yield of EDC/NHS activation step was calculated to be 0.143 assuming all surface —COOH groups are linked to NHS after activation. Experimental N/C ratio was obtained from XPS multiplex scan taken at take-off angle 45° was 0.035, and the reaction yield of this activation step was estimated 0.035/ 0.143=24.5%. A theoretical maximum N/C ratio of 0.222 is obtained similarly by assuming each PAA unit was linked with one Biotin molecule after amidation reaction. Taking into account that only ~24.5% of PAA groups are EDC/NHS activated and available for Biotin linkage, the theoretical maximum N/C ratio was reduced to 0.222×24.5%=0.054, very close to experimental N/O ratio of 0.063 after the amidation reaction. This suggests that the amidation reaction linking Biotin to PAA-NHS proceeded close to completion. The yield of both activation and amidation steps are in good agreement with Chilkoti's results.[13e]

TABLE 3

XPS and Water contact angle measurement results on derivatized polymer surfaces at each stage.

| Surfaces | C % | O % | N % | N/C | Yield | Sessile drop water contact angle θs (°) |
|---|---|---|---|---|---|---|
| PtBA | 81.50 | 18.50 | 0 | 0 | N/A | 90 |
| PAA | 74.04 | 25.96 | 0 | 0 | N/A | 35 |
| PAA-NHS | 69.76 | 27.8 | 2.44 | 0.035 | 24.5% | 42 |
| PAA-Biotin | 67.22 | 28.54 | 4.25 | 0.063 | ~100% | 57 |

Note:
1) Sessile drop water contact angles of several reference surfaces measured from spun coat thin film are: θs(PS) = 85°, θs(PtBMA) = 90°, θs(PAA) = 15°.
2) The uncertainty of contact angle values is ±2° obtained from multiple measurements.
3) All the elemental compositions are obtained from XPS multiplex high resolution scan at a take-off angle of 45°.

Characterization of azobenzene SAMs

Table 4 summarizes the water contact angle measurement results on azobenzene SAMs. As expected, sessile drop water contact angle of SAM-azo-tBu is 92°, typical of a hydrophobic surface, while that of SAM-azo-COOH is 34°, typical of a hydrophilic surface. The deprotected SAM-azo-tBu by cleavage of photogenerated acid shows a dramatic change of water contact angle from 92° to 32°, which is exactly the contact angle of SAM-azo-COOH surfaces. That confirms the success of the photochemistry of photoacid generation and its role to cleave and deprotect tert-butyl group of SAM-azo-tBu. A control experiment was run with SAM-azo-tBu spun coated with a layer of PS but without PAG, exposed to UV and postbaked, the contact angle does not change in this case. Two other experiments were performed to confirm the acid nature of this hydrophilic surface of deprotected SAM-azo-tBu. Contact angle titration of unbuffered aqueous solution showed a typical pH titration curve of surface of deprotected SAM-azo-tBu (results not shown), the break-point of pH titration curve is roughly estimated as pH=10.2 in agreement with that of other surface —COOH groups[40a]. The deprotected SAM-azo-tBu and undeprotected SAM-azo-tBu sample was soaked in a 1M NaOH solution in water for overnight. XPS showed that deprotected SAM-azo-tBu adsorbs more than 10 times amount of NaOH than undeprotected SAM-azo-tBu.

Table 4 also summarizes the elemental composition of C, N, O and S of azobenzene SAMs. The elemental composition of major element (C, O) agrees with theoretical prediction.

The BE peak position of N agrees with N of azobenzene nature (BE~399.7 eV)[42], the sulfur peak (two split peak at 162.0 eV and 163.2 eV, area ratio is 1:2, spectra not shown) also agrees with literature values of Au bound sulfur atoms[43]. There is no oxidized sulfur ($RSO_3^-$, XPS S(2p) BE~168 eV) observed either before and after UV exposure which eliminates any possibility of photo-induced sulfur oxidation[24a,b,44] under these experimental conditions.

Figure 29A:
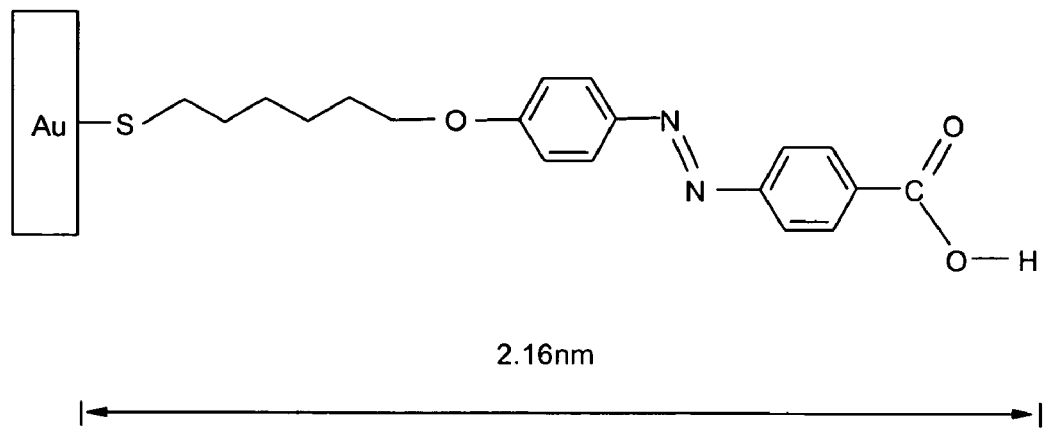
FIG. 29A and FIG. 29B are a thickness estimate of all trans SAM-azo-COOH (FIG. 29A) and C1s band assignment of SAM-azo-COOH and SAM-azo-tBu (FIG. 29B).

The XPS measured thickness of SAM-azo-COOH and SAM-azo-tBu is tabulated in Table 4. Both are close to theoretically predicted value of 2.16±0.30 nm from modeling of all trans molecular structure (FIG. 29A) from known bond lengths and angles[49] indicating that azobenzene SAMs possess molecular orientation with a small tilting angle. This is in accordance with increasing packing density, molecular order, and stability due to additional π-π interaction of azobenzene unit. Progressing upright molecular orientation was also found previously for other thioaromatic monolayers on Au(111)[50]. The XPS measured thickness also agrees with thickness of other azobenzene SAMs with similar molecular structure measured by other techniques including X-ray reflectivity and ellipsometry[51].

TABLE 4

XPS results of elemental composition at 45° take-off angle, sessile drop water contact angle and ADXPS estimated thickness of SAM-azo-COOH and SAM-azo-tBu.

|  |  | C % | O % | S % | N % | θ(° c.) | d(nm) |
|---|---|---|---|---|---|---|---|
| SAM-azo-tBu | Theory | 79.31 | 10.34 | 3.44 | 6.9 | 99 | 2.13 |
|  | Experiment | 79.34 | 15.66 | 1.41 | 3.59 |  |  |
| SAM-azo-COOH | Theory | 76 | 12 | 4 | 8 | 32 | 2.10 |
|  | Experiment | 82.83 | 12.59 | 2.12 | 2.17 |  |  |

Note: The theoretical value of elemental composition is calculated from the molecular structure.
1) The uncertainty of abundant element (C and O) is 5%, the uncertainty of trace element (S and N) is 15%.
2) The uncertainty of contact angle values is ±2° obtained from multiple measurements.

Figure 29B:
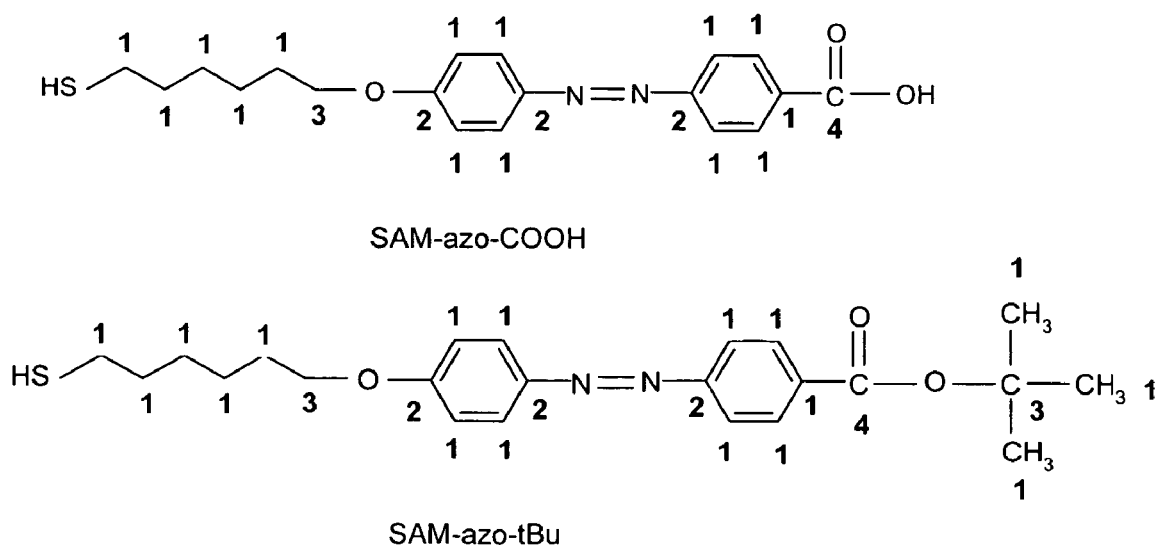

High resolution C1s and O1s spectra results are summarized in Table 5 and reveal more information about details of molecular structure of azobenzene SAMs. For both SAM-azo-COOH and SAM-azo-tBu, O1s high resolution spectra splits into 3 peaks (BE at 532.7 eV, 532.1 eV and 531.7 eV, spectra not shown here) with area ratio close to 1:1:1. O1s peaks are ascribed to O (C=O*—O), ether O next to benzene ring ($CH_2$—O*-φ)[34a,45] and ester O (C=O—O*) respectively from high BE to low BE. The main aliphatic C(C*$H_2$) composition is calculated to be 73.7% for SAM-azo-COOH (14 C atoms out of 19 total C atoms) and 73.9% for SAM-azo-tBu (17 C atoms out of 23 total C atoms) and is very close to the experimentally measured main aliphatic C composition in Table 4. The C with BE 286.8 eV (BE shift=2.2 eV) originates from C next to ether O (HS—($CH_2$)$_5$—C*—O-φ), while the C (C in the benzene ring)[45] next to ether C and azobenzene N=N shifts about 1.1 eV (BE=285.7 eV). In summary, peak assignments are C4(288.7 eV), C3(286.8 eV), C2(285.7 eV) and C1(284.6 eV) with area ratio 1:1:3:14 for SAM-azo-COOH and area ratio 1:2:3:17 for SAM-azo-tBu as shown in FIG. 29B. Experimental results are in good agreement with this assignment of C1s bands.

Angle-dependent XPS (ADXPS) is a popular technique to measure the physical thickness of ultrathin organic and inorganic and investigate the molecular orientation in SAMs.[47] To evaluate the thickness of the SAMs, the photoelectron intensity ratio between overlayer (C1s) and substrate (Au4$f_{7/2}$) is monitored as a function of take-off angle. For a flat and uniform layer, the uniform overlayer model predicts the following relation under the assumption that the mean free paths of photoelectron from both substrate and overlayer are close enough[36,48]: I(overlayer)/I(substrate)=K*($e^{d/(\lambda * \sin\theta)}$−1).

K is an instrumental constant encompassing all the factors including the atomic concentration, photoelectron mean free path, intensity from an infinite thick sample and d is the physical overlayer thickness and $\lambda$ is the photoelectron mean free path or attenuation length defined as the distance normal to the surface at which the probability of an electron escaping without significant energy loss due to inelastic scattering processes drop to 1/e of its original value. $\lambda$ is a function of kinetic energy and material electron density and often measured experimentally. Thus, ln(I(C_overlayer)/I(Au_substrate)+K')=(d/$\lambda$)*(1/sin $\theta$).

Figure 30:
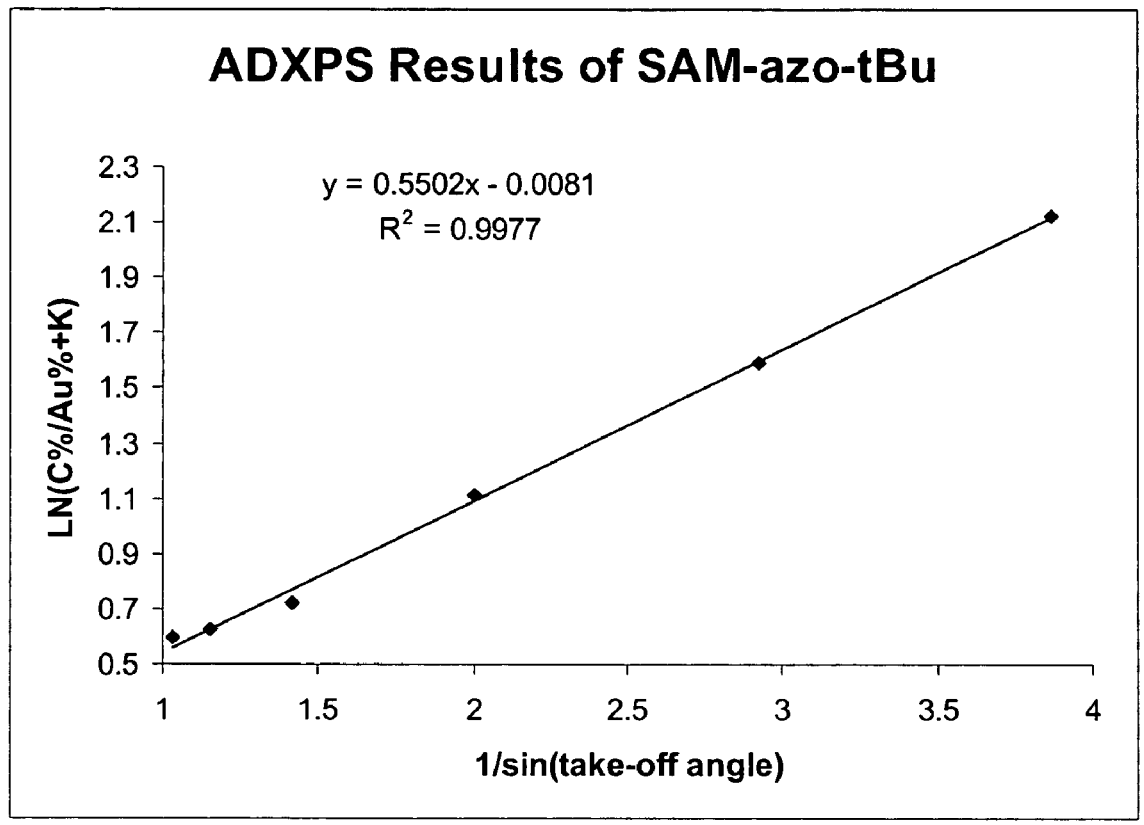
FIG. 30 shows ADXPS results of SAM-azo-tBu.

Plotting ln(I(C_overlayer)/I(Au_substrate)+K') vs. 1/sin $\theta$, the slope of the curve should be d/$\lambda$ and the overlayer thickness d can be obtained. K' here is determined by C overlayer to Au substrate intensity ratio of thickness standard sample (sample of known thickness, in this case we use SAM of dodecanthiol (HS-$C_{12}H_{23}$) which has a nominal thickness of 1.7 nm[33,47]). FIG. 30 gives an example of such plot. The value of $\lambda$=3.88 nm here is the average value of $\lambda$(Au)=4.2 nm and $\lambda$(C)=3.55 nm from literature[37].

TABLE 5

XPS results of high resolution C1s and O1s deconvolution at 45° take-off angle of SAM-azo-COOH and SAM-azo-tBu

| | Types of C1s and O1s | Peak Position (eV) | Chemical shifts | FWHM (eV) | C % (theory) | C % (experiment) |
|---|---|---|---|---|---|---|
| SAM-azo-COOH | C*H$_2$ | 284.6 | 0 | 1.16 | 73.68 | 75.08 |
| | O=C*—O | 288.6 | 4.0 | 1.33 | 5.26 | 3.82 |
| | C*H$_2$—O | 286.5 | 1.9 | 1.55 | 5.26 | 8.91 |
| | Other C* | 285.4 | 0.8 | 1.40 | 15.79 | 12.2 |
| | C=O*—OH | 533.0 | 1.6 | 1.53 | 33.33 | 33.64 |
| | CH$_2$—O*-φ | 532.7 | 1.3 | 1.38 | 33.33 | 31.60 |
| | C=O—O*H | 531.4 | 0 | 1.41 | 33.33 | 34.76 |
| SAM-azo-tBu | C*H$_2$ | 284.6 | 0 | 0.98 | 73.91 | 74.66 |
| | O=C*—O | 288.6 | 4.0 | 0.85 | 4.35 | 3.81 |
| | C*H$_2$—O | 285.4 | 0.8 | 0.81 | 8.70 | 8.13 |
| | Other C* | 286.6 | 1.8 | 1.48 | 13.04 | 13.4 |
| | CH$_2$—O*-φ | 533.0 | 1.6 | 1.24 | 33.33 | 33.33 |
| | C=O*—OH | 532.7 | 1.3 | 1.18 | 33.33 | 33.28 |
| | C=O—O*H | 531.4 | 0 | 1.23 | 33.33 | 33.39 |

Figure 31A:
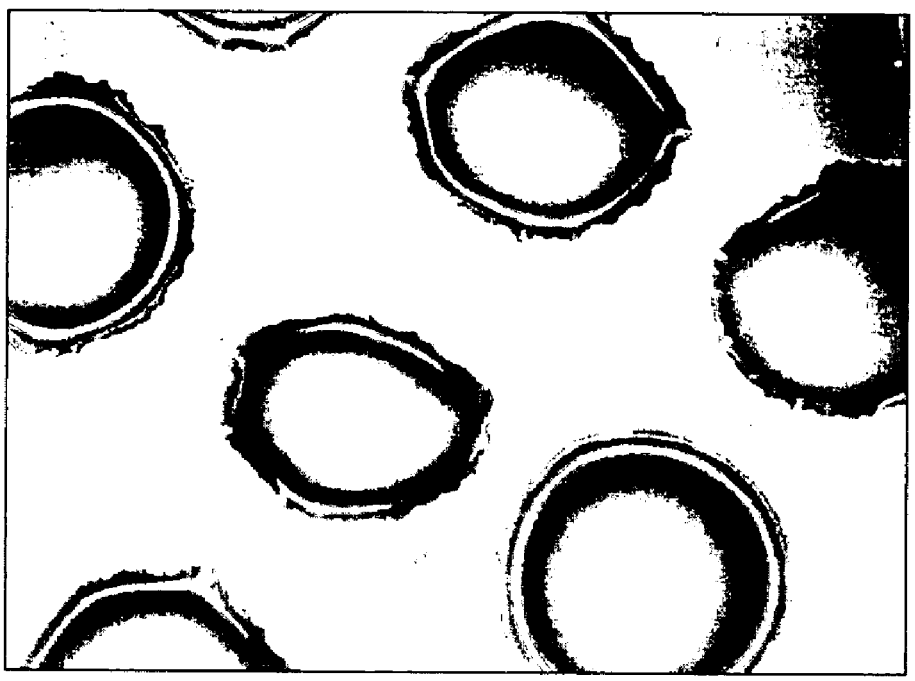
FIG. 31A and FIG. 31B are optical micrographs of water condensation images of patterned SAM-azo-tBU/SAM-azo-COOH using 5× (FIG. 31A) and 20× (FIG. 31B) objective.
Figure 31B:
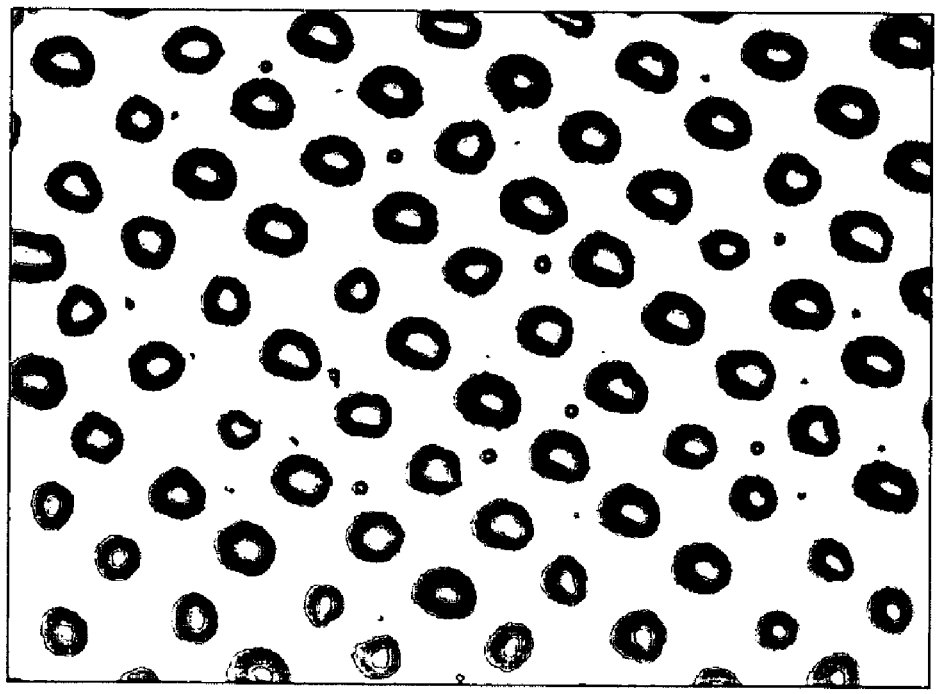

Water condensation imaging of surface pattern with different wetting property is a valuable nondestructive technique.[54] Water vapor from breath or from heated water condense into liquids on a cold surface selectively at hydrophilic surface regions to form a ordered array of droplets. Thus the pattern of droplets of water delineates the underlying surface pattern with spatially different wetting property. The images of water condensation are taken immediately after pattern formation. FIG. 31 shows two images of water condensation with different magnification. The spatial periodicity here is 500 µm.

Surface modification of usually low surface-energy polymers has attracted much research attention in order to improve their adhesion, wettability, printability, and biocompatibility without affecting the desirable their bulk properties. The ability to modify and control chemical functionality on polymer surfaces in a precise manner is highly desirable because a change of surface chemistry changes the surface free energy and other material properties of interest and also allows further surface derivaization of external ligands, which is an important way to build molecular assemblies with confined positions for more complex nanoscale and biomolecular devices.

Besides controlling surface chemical functionalities in a homogeneous way, it is also desirable to be able to control the spatial distributions of the surface chemical functionalities, i.e. patterning polymer surfaces into heterogeneous surfaces with different chemical functionalities or hydrophobicity at well-defined regimes with usually micron or submicron pattern feature size. This has tremendous potential application in thin film device fabrication for modem technology, particularly in microelectronics, information storage, optics and sensors. Patterned surfaces are also useful as universal templates to assist self-assembly and selective deposition of an object of interest.

Methods of modifying the surface functionality and pattern surfaces of two systems by photoactive diblock copolymer polymer brushes and end-functional azobenzene self-assembled monolayers based on the chemical amplification deep UV photolithography are provided. One embodiment of chemical amplified resist technology is the use of the photoacid generator, which produces a strong acid upon exposure to deep UV radiation. When coupled with thermolysis, the photogenerated strong acid catalyzes the chemical reactions that fragments the polymers with acid-labile pendant groups in the resists, and changes the solubility of resists for further developing steps. As a consequence of this chemical amplification concept, the DUV photoresist is more sensitive and thus shortens drastically the exposure time from several hours to a few minutes or even seconds. The chemical amplification concept is also applicable to change the chemical functionality at the surfaces of polymers and self-assembled monolayers. PAG generates a small amount of strong acid and deprotects the initial tert butyl groups to form carboxylic acid groups at polymer brush surfaces. When such surface modification is done in a patternwise fashion using photomasks during the DUV exposure step, surface patterns with alternate hydrophobic tert butyl groups and hydrophilic carboxylic acid groups are generated.

This technique is a unique way to introduce chemical functionality to the surface through surface segregation of the surface-active block of a diblock copolymer. This approach of surface modification and micropatterning exhibits advantages compared to other approaches: 1) it allows molecular level control of the top surface layer containing the surface functionality by controlling the annealing time, temperature and the amount of spin-casted diblock copolymer. 2) It has wide applicability due to its easiness and universality. The surface tension of PTBA and PtBMA is smaller than most common polymers, so the surface segregation should still happen and thus it is a universal and generic way to modify the surface on other polymers. 3) It is implantable from mature microelectronic technology. Pattern feature resolution can be extended to the resolution of current commercial chips. 4) The process is amenable to patterning biomolecules. PtBA is a biocompatible photoresist; water or ethanol is used as solvent in every step for biomolecules immobilization, and UV exposure and residue photoresist removal are carried out prior to biomolecule immobilization. These features minimize the risk of reducing biological reactivity. 5) Well-defined and reliable DUV photochemistry allows the selective physisorption and covalent bonding of external ligands.

Surface Micropatterning to Regulate Cell Functions

Micropatterning is amenable to various types of biomolecules, including cell adhesion or growth factors. The peptide RGD (Arg-Gly-Asp) is a well-documented cell adhesion promoter and is covalently conjugated to an active surface functionality such as a carboxylic acid groups. Cell growth is then regulated with two dimensional micron size resolution. The ability to control the cell interaction and modulation provides tools for understanding the mechanism of modulate cellular activities.

Micropatterning of Metal Nanoparticles

Due to their small size, metal nanoparticles often have properties that are different from those of bulk metals. These novel properties find applications in areas such as photoelectronics, catalysis, magnetism and sensing. Metal nanoparticles are selectively deposited in defined areas of the surface patterns described herein through metal-substrate complex interactions, including the interaction between zinc oxide nanoparticles and surface carboxylic groups.

Micropatterning of Multilayered Polyelectrolyte Films

The layer-by-layer (LBL) self-assembly of polyelectrolytes is a general and powerful method to build tailored ultrathin films of defined thickness, composition and structure. The LBL approach has been used extensively to prepare thin films for a variety of applications including biosensing, catalysis, separations and optics. In conventional LBL, substrates are alternately dipped in solutions containing anionic and cationic species, usually polyelectrolytes with opposite electrostatic charges. The polyelectrolytes self-assemble into alternating films on top of the solid support primarily via electrostatic interactions. This film deposition method allows good control of thickness at molecular level. Nanoparticles can also be incorporated into the multilayered polyelectrolytes through metal-polymer complex systems. Patterned polymer substrates with coexisting hydrophilic, carboxylic and hydrophobic, tert-butyl ester groups as described herein are amenable to LBL processes for patterning multilayered polyelectrolytes, including nanoparticles embedded in the film or deposited on the top of the film.

Photophysical Patterning

Azobenzene cis-trans photoisomerization property is useful for photophysical patterning in addition to the chemical patterning strategy described above. Photophysical patterning is useful for photoswitching devices, and for demonstrating the directionality of hydrogen bonding.

References for Example 5

1) (a) Blaaderen A. V.; Ruel R.; Wiltzius P. *Nature,* 1997, 385, 321. (b) Singhvi R. et al., *Science,* 1994, 264, 696. (c) Roxlo C. B. et al., *Science,* 1987, 235, 1629. (d) Hayashi et al., *J. Colloid Interface Sci.* 1991, 144, 538. (e) Burmeister et al., *Langmuir* 1997, 13, 2983.

2) (a) Seok C.; Freed K. F. *J. Chem. Phys.* 2000, 112, 6452. (b) Karim, A.; Douglas J. F.; Lee B. P.; Glotzer S. C.; Rogers J. A.; Jackman R. J.; Amis E. J.; Whitesides G. M. et al, *Phys. Rev. E.* 1998, 57, R6273.

3) Kokkoli E.; Zukoski C. F. *Langmuir* 2001, 12, 369.

4) (a) Sun Y; Walker G. C. *J. Phys. Chem. B* 2002, 106, 2217 (b) Aizenberg J.; Braun P. V.; Wiltzius P. *Phys. Rev. Lett.* 2000, 84, 2997 (c) Jonas U.; Campo A. D.; Kruger C.; Glasser G.; Boss D. *Proc. Natl. Acad. Sci.* 2002, 99(8), 5034.

5) Aizenberg J.; Black A. J.; Whitesides G. M. *Nature* 1999, 398, 495.

6) Abbott N. J.; Whitesides G. M.; Racz L. M.; Szekely J. *J. Am. Chem. Soc.* 1995, 117, 12050.

7) (a) Yin Y.; Lu Y.; Gates B.; Xia Y. *J. Am. Chem. Soc.* 2001, 123, 8718 (b) Guo Q.; Aroux C.; Palmer R. E. *Langmuir* 2001, 12, 369 (c) Qin D.; Xia Y.; Xu B.; Yang H.; Zhu C.; Whitesides, G. M. *Adv. Mater.* 1999, 11, 1433.

8) (a) Himmelhaus M; Takei H. *Phys. Chem. Chem. Phys.* 2002, 4, 496. (b) Hata, K.; Fujita M.; Yoshida S.; Yasuda S.; Makimura T.; Makimura K.; Shigekawa, H. *Appl. Phys. Lett.* 2001, 79, 692.

9) (a) van Blaaderen, A.; Reul, R.; Wiltzius, P.; *Nature* 1997, 385, 321. (b) van Blaaderen, A.; Wiltzius, P. *Adv. Mater.* 1997, 9, 833.

10) Gillmor S. D.; Thiel A. J.; Strother T. C.; Smith L. M.; Lagally M. G. *Langmuir* 2000, 16, 7223

11) (a) Blawas A. S.; Reichert W. M., *Biomaterials* 1998, 19, 595 (b) Tan J. L.; Tien J; Chen C. S. *Langmuir* 2002, 18, 519 (c) Bernard A.; Delamarche E.; Schmid H.; Michel B.; Bosshard H. R.; Biebuyck H. *Langmuir* 1998, 14, 2225 (d) Nicolau D. V.; Suzuki H.; Mashiko S.; Taguchi T.; Yoshikawa S. *Biophysical J.* 1999, 77, 1126 (e) Nicolau D. V.; Taguchi T.; taniguchi H.; Yoshikawa S. *Colloids and Surfaces A* 1999, 155, 51.

12) (a) Dewez J. L.; Lhoest J. B.; Detrait E.; Berger V.; Dupont-Gillain C. C.; Vincent L. M.; Schneider Y. J. Bertrand P.; Rouxhet, P. G. *Biomaterials* 1998, 19, 1441 (b) Hyun J.; Ma H.; Banerjee P.; Cole J.; Gonsalves K.; Chilkoti A. *Langmuir* 2002, 18, 2975.

13) (a) Schwarz A.; Rossier J. S.; Roulet E.; Mermod N.; Roberts M. A.; Girault H. H. *Langmuir* 1998, 14, 5526 (b) Hyun J.; Zhu Y.; Liebmann-Vinson A.; Beebe T. P.; Chilkoti A. *Langmuir* 2001, 17, 6358 (c) Hyun J.; Chilkoti A. *J. Am. Chem. Soc.* 2001, 123, 6943 (d) Nicolau D. V.; Taguchi T.; Taniguchi H.; Yoshikawa S. *Langmuir* 1998, 14, 1927. (e) Yang Z.; Belu A. M.; Liebmann-Vinson A.; Sugg H.; Chilkkoti A. *Langmuir* 2000, 16, 7482. (f) Yang Z.; Chilkoti A. *Adv. Mater.* 2000, 12, 413.

14) (a) Zhao B.; Brittain W. J.; Zhou W. Cheng S. Z. D. *J. Am. Chem. Soc.* 2000, 122, 2407 (b) Husemann M.; Mecerreys D.; Hawker C. J.; Hedrick J. L.; Shah R.; Abbott N. L. *Angew. Chem. Int. Ed.* 1999, 38, 647 (c) Husemann M.; Morrison M.; Benoit D.; Frommer J.; Mate C. M.; Hinsberg W. D.; Hederick J. L.; Hawker C. J. *J. Am. Chem. Soc.* 2000, 122, 1844.

15) Revzin A.; Russell R.; Yadavalli V. K.; Koh W.; Deister C.; Hile D. D.; Mellott M. B.; Pishko M. V. *Langmuir* 2001, 17, 5440

16) Kumar, A.; Biebuyck, H. A.; Whitesides, G. M. *Langmuir* 1994, 10, 1498

17) Zhao X. K.; Fendler J. H. *J. Phys. Chem.* 1991, 95, 3716.

18) (a) Flouders A. W.; Brandon, D. L.; Bates, A. H. *Biosensors & Bioelectronics* 1997, 12, 447. (b) Mooney J. F.; Hunt A. J.; Mcintosh J. R.; Liberko C. A.; Walba D. M.; Rogers C. T. *Proc. Natl. Acad. Sci.* 1996, 93, 12287

19) (a) Kumar A; Whitesides G. M. *Appl. Phys. Lett.* 1993, 63, 2002. (b) Kumar A. et al., *Acc. Chem. Res.* 1995, 28, 219.

20) Werwa E.; Seraphin A. A.; Chiu L. A.; Zhou C.; Kolenbrander K. D. *Appl. Phys. Lett.* 1994, 64, 1821.

21) Peters R. D.; Yang X. M.; Kim T. K.; Sohn B. H.; Nealey P. F. *Langmuir* 2000, 16, 4625.

22) (a) Wybourne M. N.; Yan M.; Keana J. F. MW; Wu J. C. *Nanotechnology* 1996, 7, 302. (b) Gillen G.; Wight, S.; Bennett, J; Tarlov, M. *Appl. Phys. Lett.* 1994, 65, 534. (c) Tiberio, R. C.; Craighead H. G.; Lercel M.; Lau T.; Sheen C. W.; Allara D. L. *Appl. Phys. Lett.* 1993, 62, 476.

23) (a) Abbott N. L.; Folkers J. P.; Whitesides G. M. *Science* 1992, 257, 1380. (b) Ross C. R.; Sun L.; Crooks R. M. *Langmuir* 1993, 9, 632.

24) (a) Tarlov M. J.; Burgress D. R.; Gillen G. *J. Am. Chem. Soc.* 1993, 115, 5305. (b) Huang J.; Dahlgren D. A.; Hemminger J. C. *Langmuir* 1994, 10, 626. (c) Sundberg, S. A.; Barret R. W.; Pirrung M.; Lu A. L.; Kiangsoontra B.; Holmes, C. P. *J. Am. Chem. Soc.* 1995, 117, 12050. (d) Hengsakul M.; Cass, A. E. G. *Bioconjugate Chem.* 1996, 7, 249. (e) Dulcey C. S.; Georger J. H.; Chen M. S.; McElvany S. W.; O' Ferrall C. E.; Benezra V. I.; Calvert J. M. *Langmuir* 1996, 12, 1638. (f) Nakagawa M.; Oh S. K.; Ichimura K. *Adv. Mater.*, 2000, 12, 403.

25) Wallraff G. M.; Hinsberg W. D. *Chem. Rev.* 1999, 99, 1801.

26) Palacin S.; Hidber P. C.; Whitesides G. M. et al, *Chem. Mater.* 1996, 8, 1316.

27) Dou as A.; Argitis P.; Misiakos K.; Dimotikali D.; Petrou P. S.; Kakabakos S. E. *Biosensors & Bioelectronics* 2002, 17, 269.

28) Pappas, S. P. *J. Imaging. Tech.* 1985, 11(4), 146.

29) Rasmussen J. R.; Stedronsky E. R.; Whitesides G. M. *J. Am. Chem. Soc.* 1977, 99, 4736.

30) Yang Z.; Galloway J.; Yu H. *Langmuir* 1999, 15, 8405.

31) (a) Bhatia Q. S.; Pan, D. H.; Koberstein J. T. *Macromolecules* 1988, 21, 2166. (b) Koberstein J. T. *MRS. Bull.* 1996, 21, 16.

32) Bramdrup J.; Immergwt E. H. *Polymer Handbook*, 4$^{th}$ ed. John Wiley&Sons Inc. New York, 1999.

33) Bain C. D.; Troughton E. B.; Tao Y. T.; Evall J.; Whitesides G. M.; Nuzzo R. G. *J. Am. Chem. Soc.* 1989, 111, 321.

34) (a) Briggs D.; Beamson G. *Anal. Chem.* 1993, 65, 1517. (b) Guiomar A. J.; Guthrie J. T.; Evans S. D. *Langmuir* 1999, 15, 1198. (c) Yang Z.; Engquist I.; Wirde M.; Kauffmann J.; Gelius U.; Liedberg B. *Langmuir* 1997, 13, 3210.

35) (a) Mansky P.; Russell T. P.; Hawker C. J. Pitsikalis M.; Mays J. *Macromolecules* 1997, 30, 6810. (b) Bates, F. S.; Fredrickson, G. H. *Annu. Rev. Phys. Chem.* 1990, 41, 525. (b) Coulon, G.; Deline, V. R.; Green, P. F.; Russell, T. P. *Macromolecules* 1989, 22, 2581. (c) Anastasiadis, S. H.; Russell, T. P.; Satija, S. K.; Majkrzak, C. F. *Phys. Rev. Lett.* 1989, 62, 1852. (d) Henkee, C. S.; Thomas, E. L.; Fetters, L. J. *J. Mater. Sci.* 1988, 23, 1685. (e) Brown G. Chakrabarti A. *Macromolecules* 1995, 28, 7817.

36) Andrade J. D. *Surface interfacial aspects of biomedical polymer* v1 1985, Plenum Press, New York, Chpt. 5, P178.

37) (a) Bain C. D.; Whitesides G. M. *J. Phys. Chem.* 1989, 93, 1670 (b) Laibinis P. E.; Bain, C. D.; Whitesides G. M.; *J. Phys. Chem.* 1991, 93, 7017 (c) Nelson K. E.; Gamble L.; Stayton P. et al, *Langmuir* 2001, 17, 2807 (d) Tamada K.; Ishida T.; Knoll W.; Fukushima H.; Colorodao R.; Groupe M.; Shmakova O. E.; Lee T. R. *Langmuir* 2001, 17, 1913.

38) Ito H.; Ueda M.; Ebina M.; *Polymers in Microlithography: Materials and processes*; ACS Symposium Series 412; American Chemical Society: Washington, DC, 1990; p57.

39) Delamarche E.; Sundarababu G.; Biebuyck H.; Michel B.; Gerber Ch.; Sigrist H.; Wolf H.; Ringsdorf H.; Xanthopoulos N.; Mathieu H. J. *Langmuir* 1996, 12, 1997.

40) (a) Randall S.; Farley H.; Reamey R. H.; MaCarthy T. J.; Deutch J.; Whitesides G. M. *Langmuir* 1985, 1, 725.

41) (a) Nelson K. J.; Gamble L.; Jung L. S.; Boecki M. S.; Naeemi E.; Golledge S. L.; Sasaki T.; Caster D. G.; Campbell C. T.; Stayton P. S. *Langmuir* 2001, 17, 2807. (b) Geyer, W.; Stadler, V.; Eck, W.; Zharnikov, M.; Gölzhäuser, A.; Grunze, M. *Appl. Phys. Lett.* 1999, 75, 2401. (c) Zharnikov, M.; Frey, S.; Heister, K.; Grunze, M. *Langmuir* 2000, 16, 2697.

42) Zhang Q.; Huang H.; He H.; Chen H.; Shao H.; Liu Z. *Surface Science* 1999, 440, 142.

43) (a) Castner D. G.; Hinds K.; Grainger D. W. *Langmuir* 1996, 12, 5083. (b) Bourg M. C.; Badia A.; Lennox R. B. *J. Phys. Chem. B* 2000, 104, 6562. (c) Taso M. W.; Pfeifer K. H.; Rabolt J. F. Castner D. G.; Haussling L.; Ringsdorf H. *Macromolecules* 1997, 30, 5913.

44) (a) Gillen G.; Bennett J.; Tarlov M. J.; Burgess D. R. F. *Anal. Chem.* 1994, 66, 2170. (b) Huang J.; Hemminger J. C. *J. Am. Chem. Soc.* 1993, 115, 3342.

45) Eynde X. V.; Bertrand P. *Surf Interface Anal.* 1999, 27, 157.

46) Beamson, G; Briggs D.; *High Resolution XPS of Organic Polymers;* John Wilney&Sons; New York, 1992.

47) (a) Kondo T.; Yanagida M.; Shimazu K.; Uosaki K. *Langmuir* 1998, 14, 5656 and the references therein. (b) Dannenberger O.; Weiss K.; Himmel H. J.; Jager B.; Buck M.; Woll Ch. *Thin solid films* 1997, 307, 183.

48) (a) Fadley C. S. *Porg. Solid. State. Chem.* 1976, 11, 265. (b) Ulman, A. *Characterization of organic thin film*, Butterworth-Heinemann Inc, P221, Boston, 1995.

49) C—C=1.545 Å, ∠CCC=110.5°, C—S=1.81 Å, C—H=1.1 Å, C—O=1.36 Å, Au—S=1.5 Å, C—C(in benzene ring)=1.399 Å, C—N(in azobenzene)=1.482 Å, N—N(in azobenzene)=1.247 Å, ∠CNN (in azobenzene)=112.3°, C—O(in —COOH)=1.364 Å, O—H≈1 Å. All value taken from CRC, Handbook of Chemistry and Physics, 3rd Electronic Edition.

50) (a) Tour, J. M.; Jones, L., II; Pearson, D. L.; Lamba, J. S.; Burgin, T. P.; Whitesides, G. M.; Allara, D. L.; Parikh, A. N.; Atre, S. V. *J. Am. Chem. Soc.* 1995, 117, 9529. (b) Sabatani, E.; Cohen-Boulakia, J.; Bruening, M.; Rubinstein, I. *Langmuir* 1993, 9, 2974. (c) Tao, Y.-T.; Wu, C.-C.; Eu, J.-Y.; Lin, W.-L. *Langmuir* 1997, 13, 4018. (d) Dhirani, A.-A.; Zehner, W.; Hsung, R. P.; Guyot-Sionnest, P.; Sita, L. *J. Am. Chem. Soc.* 1996, 118, 3319. (e) Ishida, T.; Choi, N.; Mizutani, W.; Tokumoto, H.; Kojima, I.; Azehara, H.; Hokari, H.; Akiba, U.; Fujihira, M. *Langmuir* 1999, 15, 6799. (f) Frey, S.; Stadler, V.; Heister, K.; Eck, W. Zharnikov, M.; Grunze, M.; Zeysing B.; Terfort, A. *Langmuir* 2001, 17, 2408.

51) (a) Siewierski L. M.; Brittain W. J.; Petrash S.; Foster M. D. *Langmuir* 1996, 12 5838. (b) Han S. W.; Kim C. H.; Hong S. H.; Chung Y. K.; Kim K. *Langmuir* 1999, 15, 1579.

52) (a) Rabek J. F.; *Photochemistry and Photophysics*, Chapter 4. 1990, CRC Press. Inc. (b) Wyman, C. *Chem.*

Rev. 1955, 55, 625. (c) Ross D. L.; Blanc J. *Photochromism* Brown G. H. Interscience, 1971, New York.

53) (a) Vavasour, J. D.; Whitmore M. D. *Macromolecules* 1992, 25, 5477. (b) Leibler L. *Macromolecules* 1992, 25, 5477.

54) (a) Lopez G. P.; Biebuyck H. A.; Frisbie C. D.; Whitesides G. M. *Science* 1993, 260, 647. (b) Kumar A.; Whitesides G. M. *Science* 1994, 262, 647.

EXAMPLE 6

Self-Assembled Monolayers

In one embodiment, the invention provides a method for modifying a surface comprising coating a monolayer on a substrate; wherein the monolayer is formed by self-assembly of end-functionalized surfactant molecules, thereby positioning a photoactive functional group at the air-monolayer interface; and exposing the monolayer to radiation, thereby modifying the surface of the monolayer, provided that if the monolayer is a self-assembled monolayer of organic groups, then each organic group contains a first functionality that is not capable of being converted to a second functionality by exposure to an acid to functionally modify the surface.

Photochemical techniques can be used to attach polymers to surfaces. These techniques can stabilize thin films against dewetting by photochemically immobilizing on the surface. For example, antigens can be immobilized on a glass surface. These techniques can also allow control of polymer deposition, for example, by using a photomask to selectively pattern the surface. In one embodiment, the SAM can be patterned using standard photolithographic techniques that are known in the art. For example, SAMs can be patterned with light in the presence of a photomask. Photochemically patterned surfaces can serve as a means for templating two-dimensional geometric patterns of a variety of objects and molecules.

Figure 32:
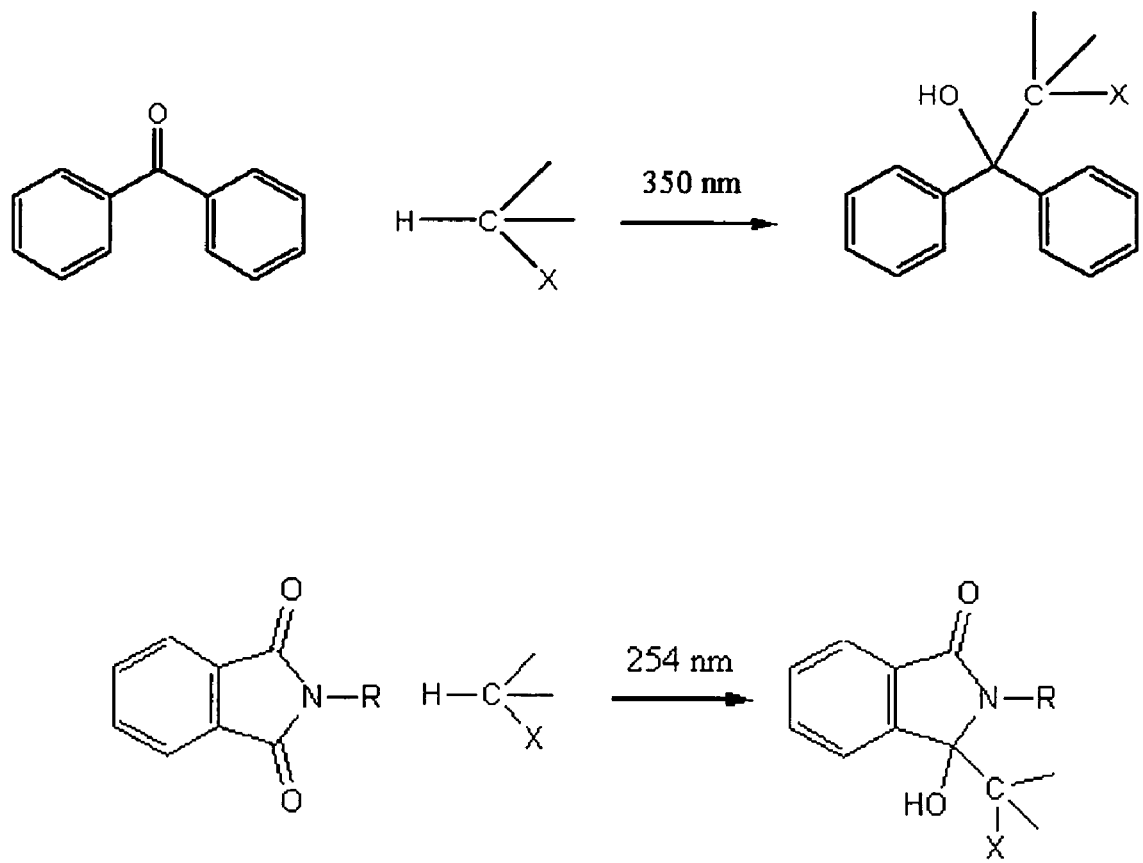
FIG. 32 shows compounds useful for the photochemical attachment of polymer films.

For example, carbonyl-containing compounds such as benzophenone and phthalimide are useful for the photochemical attachment of polymer films. As shown in FIG. 32, the carbonyl group of benzophenone can be exposed to radiation at 350 nm and in the presence of an activated carbon, denoted as "C—X" to form the corresponding alcohol. Similarly, FIG. 32 demonstrates that a carbonyl group of phthalimide can be exposed to radiation at 254 nm in the presence of an activated carbon to form the corresponding alcohol.

Figure 33A:
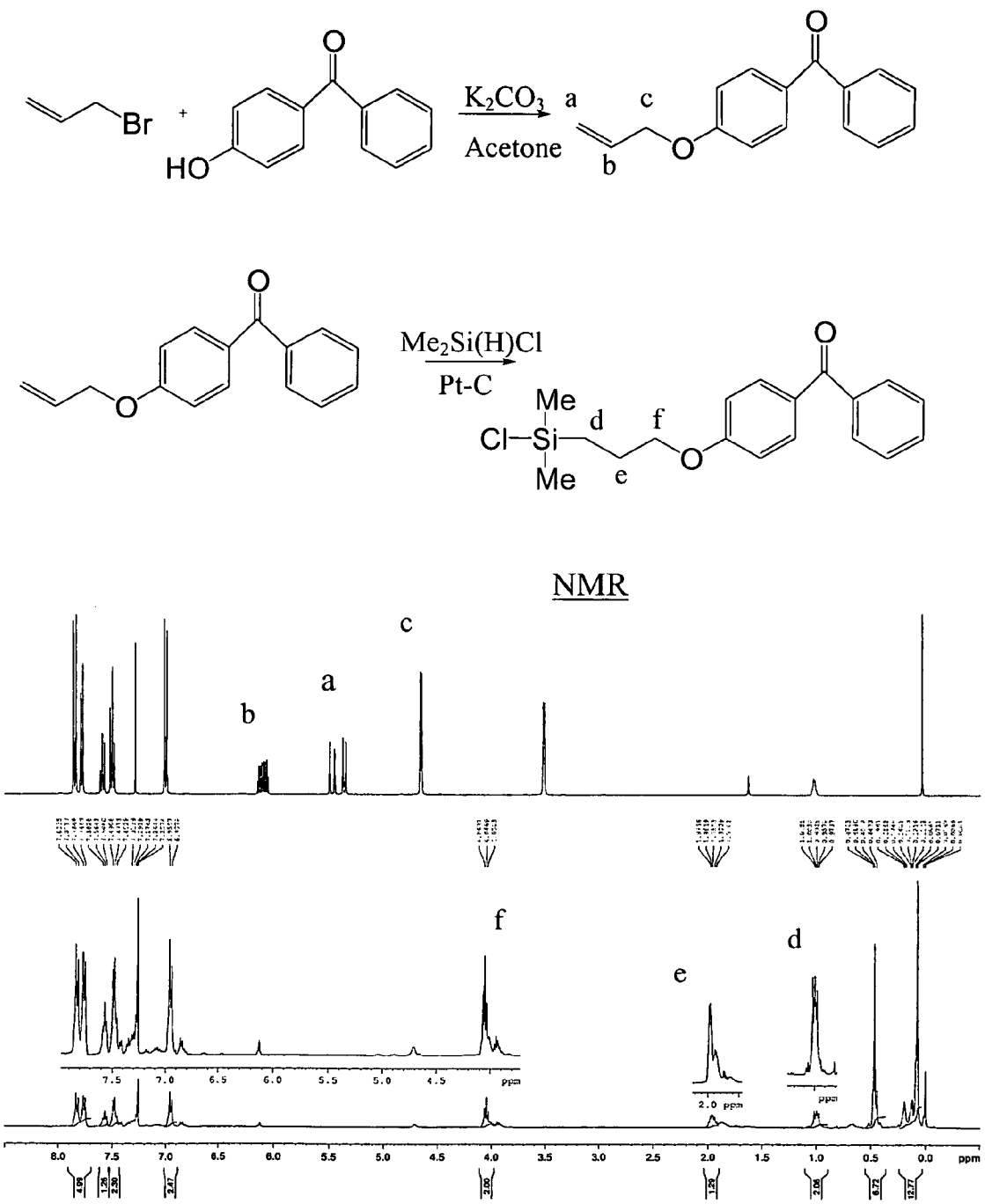
FIG. 33A and FIG. 33B demonstrate the preparation of a benzophenone SAM.
Figure 33B:
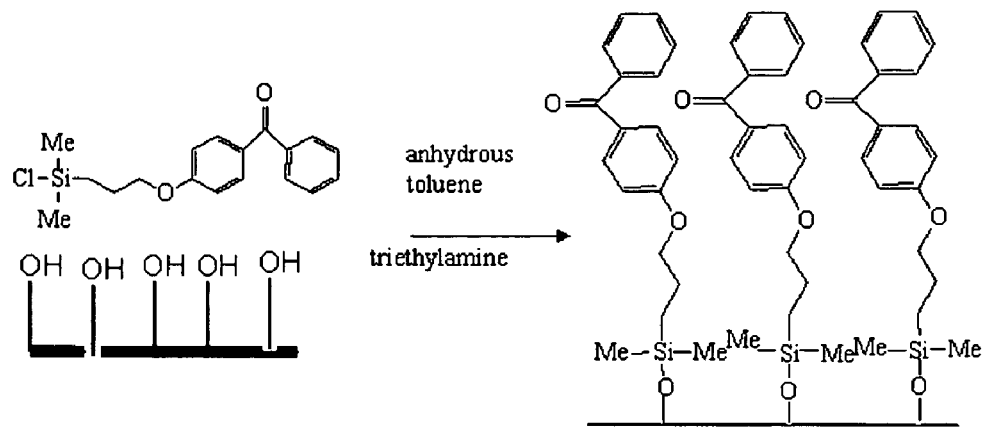
Figure 33B:
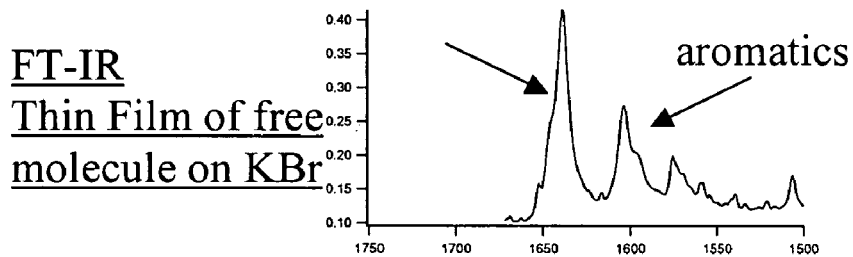
Figure 33B:
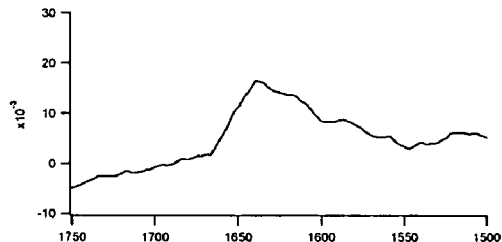

A benzophenone self-assembled monolayer can be synthesized as outlined in FIGS. 33A and 33B. For example, hydroxyl-substituted benzophenone can be reacted with allyl bromide in the presence of $K_2CO_3$ in acetone, and the resulting alkene can be reacted with chlorodimethylsilane in the presence of Pt/C to form a silyl-tethered benzophenone. Silyl-tethered benzophenone monomers can assemble on a hydroxyl-containing surface in the presence of anhydrous toluene and triethylamine to provide a benzophenone SAM.

Figure 34A:
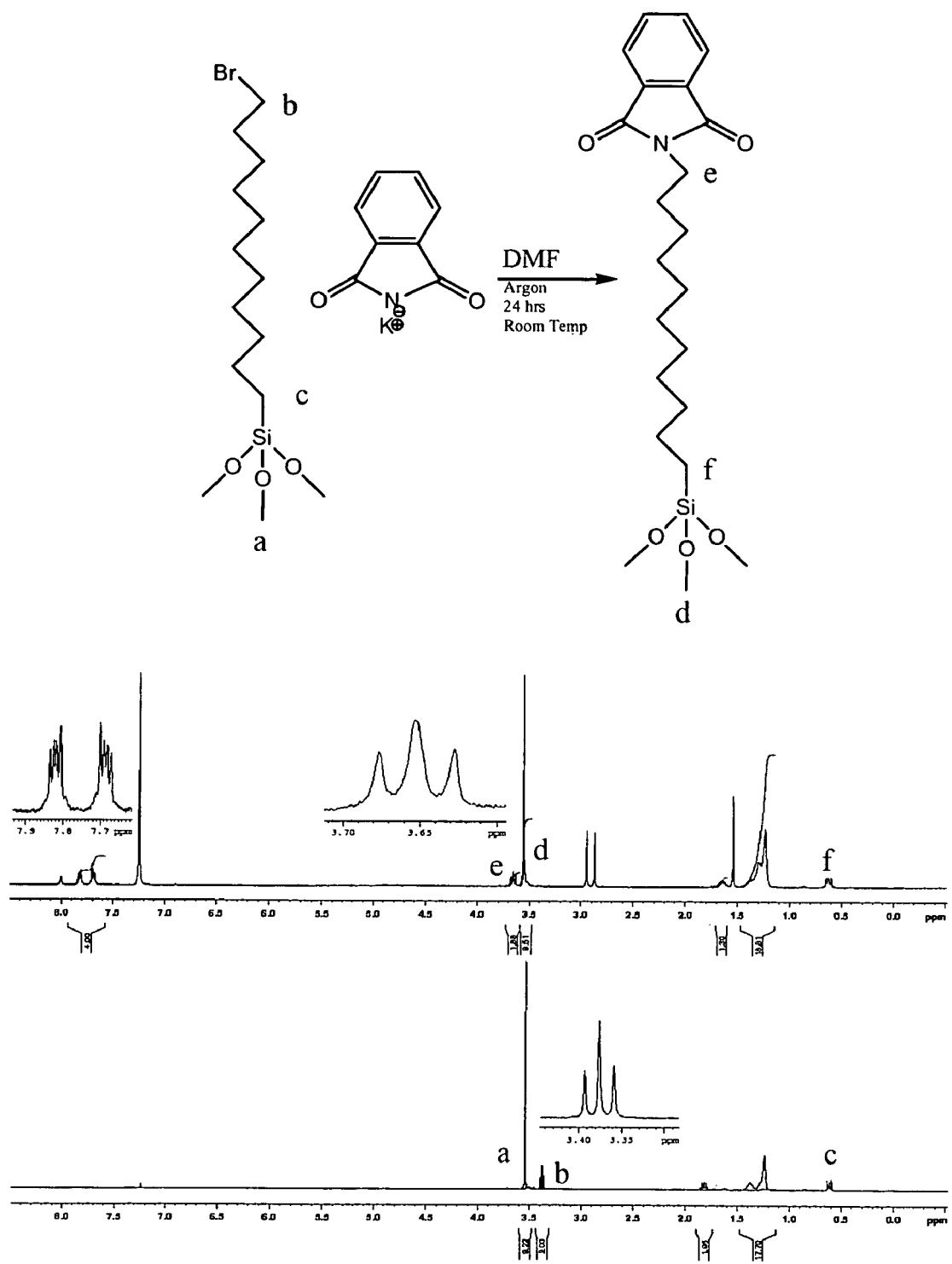
FIG. 34A through FIG. 34C show the preparation of a phthalimide SAM.
Figure 34B:
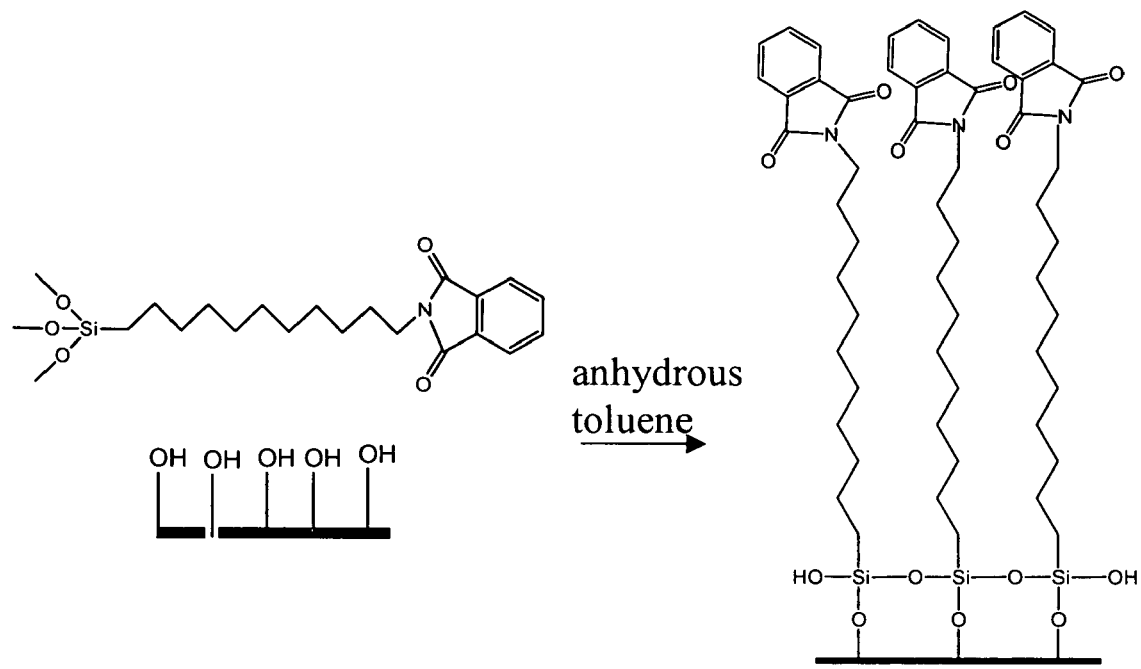
Figure 34C:
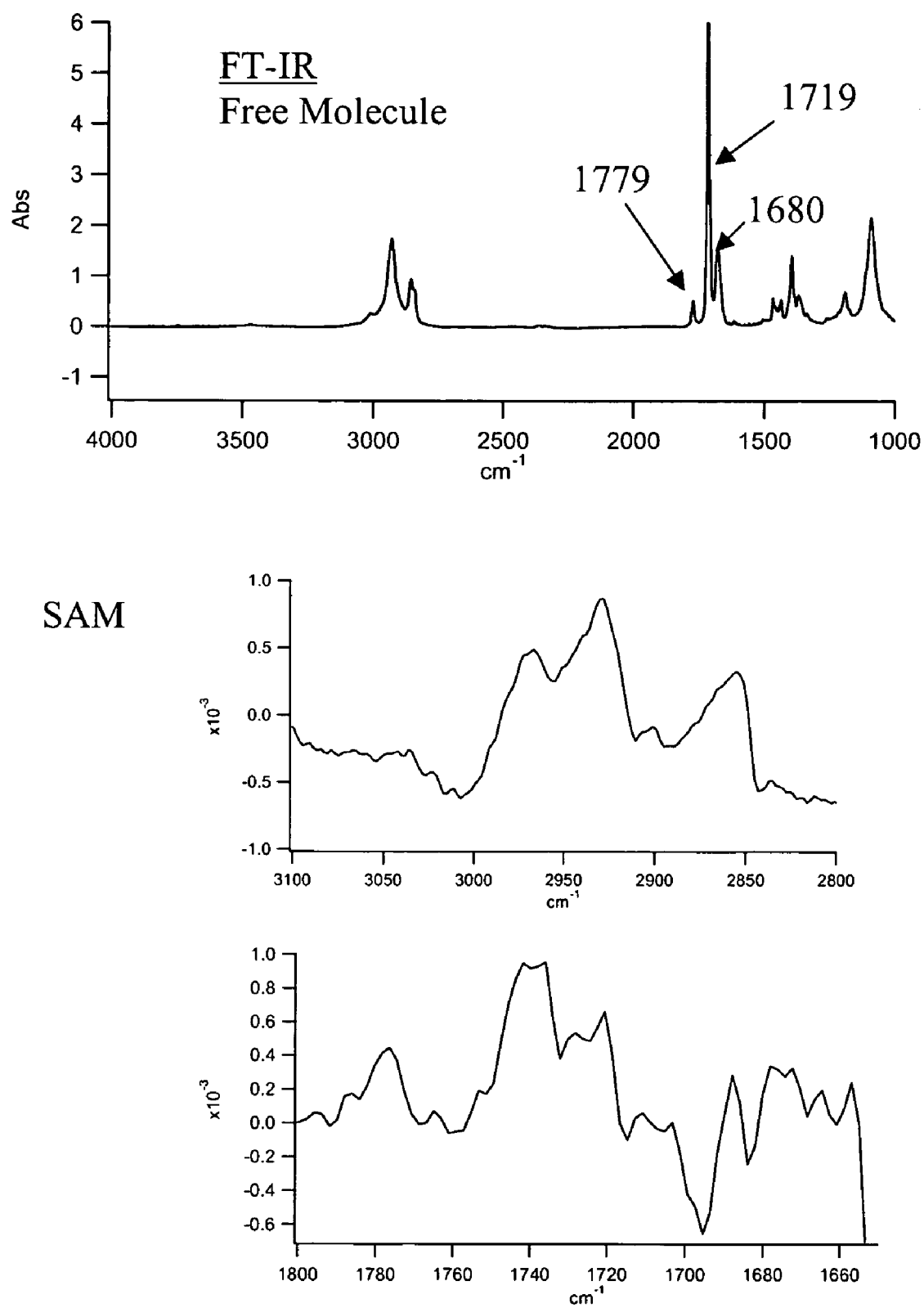

A phthalimide SAM can be synthesized as outlined in FIGS. 34A through 34C. Reaction of phthalimide with the desired alkyl silane bromide in DMF produces a silyl-tethered phthalimide. Silyl-tethered phthalimide monomers can assemble on a hydroxyl-containing surface in the presence of anhydrous toluene to provide a phthalimide SAM.

Figure 35A:
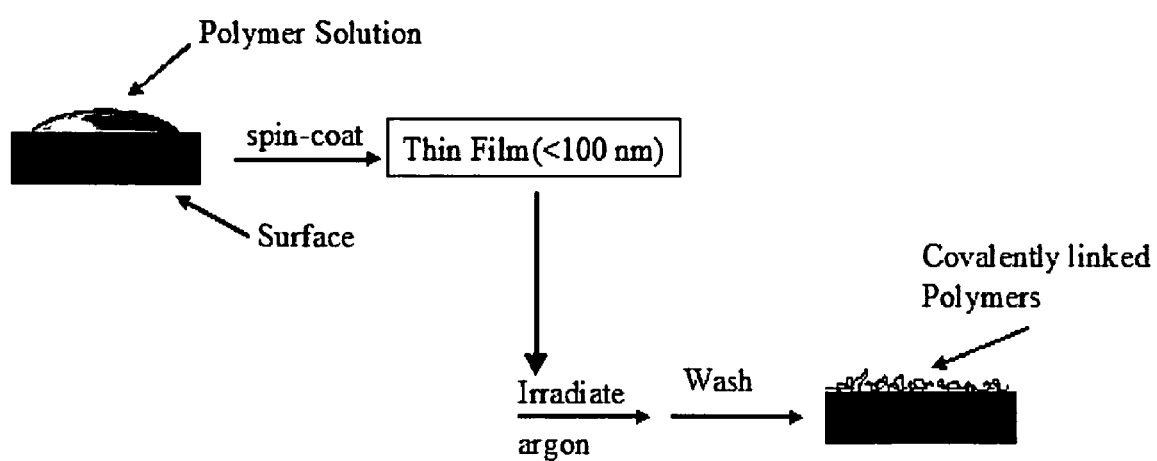
FIG. 35A and FIG. 35B show an exemplary procedure for grafting polymers onto the surface of a SAM.
Figure 35B:
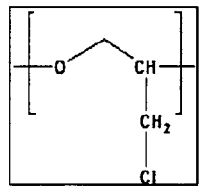
Figure 35B:
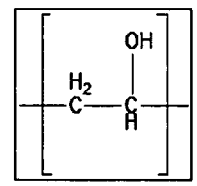
Figure 35B:
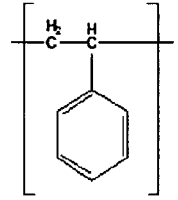

The SAM can also be coated with a macromolecular surfactant such as a polymer. In one embodiment, as set forth in FIGS. 35A and 35B. This is accomplished by grafting the polymer onto the SAM surface, for example by spin-coating a polymer solution to produce a thin film. The thin film can be irradiated and washed to provide a polymer that is covalently linked to the SAM surface. In each case, the resulting polymer coating can be examined by XPS or other techniques known in the art.

Figure 36A:
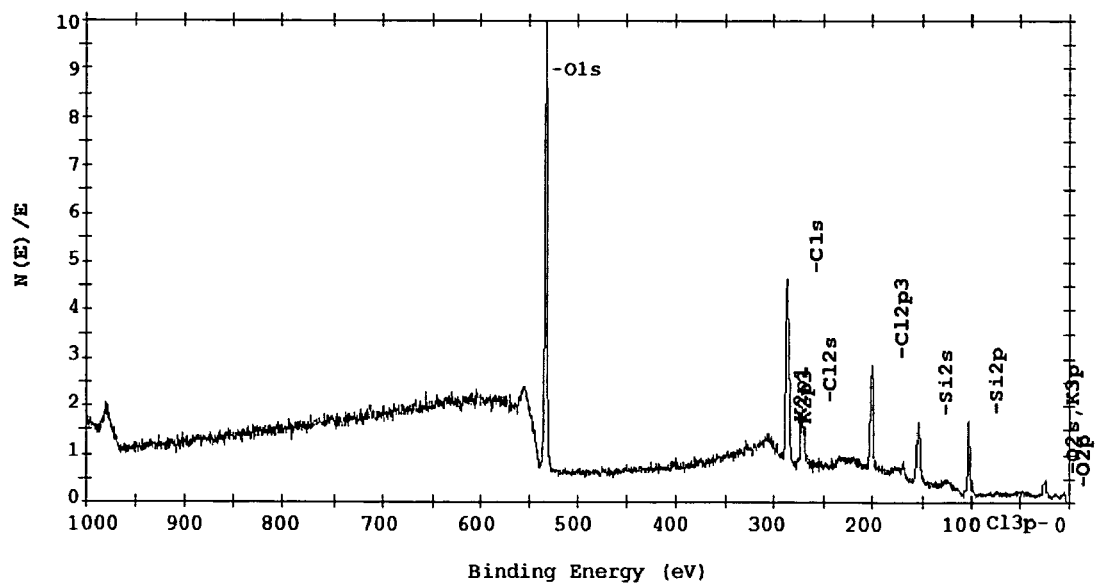
FIG. 36A through FIG. 36C demonstrate features of a PECH-tethered benzophenone SAM.
Figure 36B:
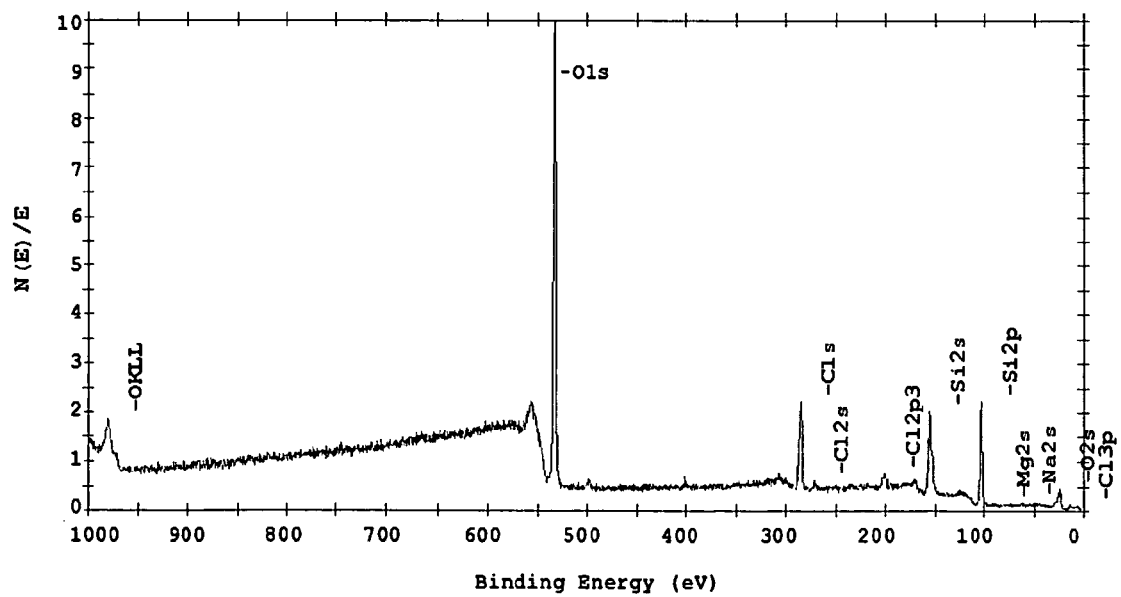
Figure 36C:
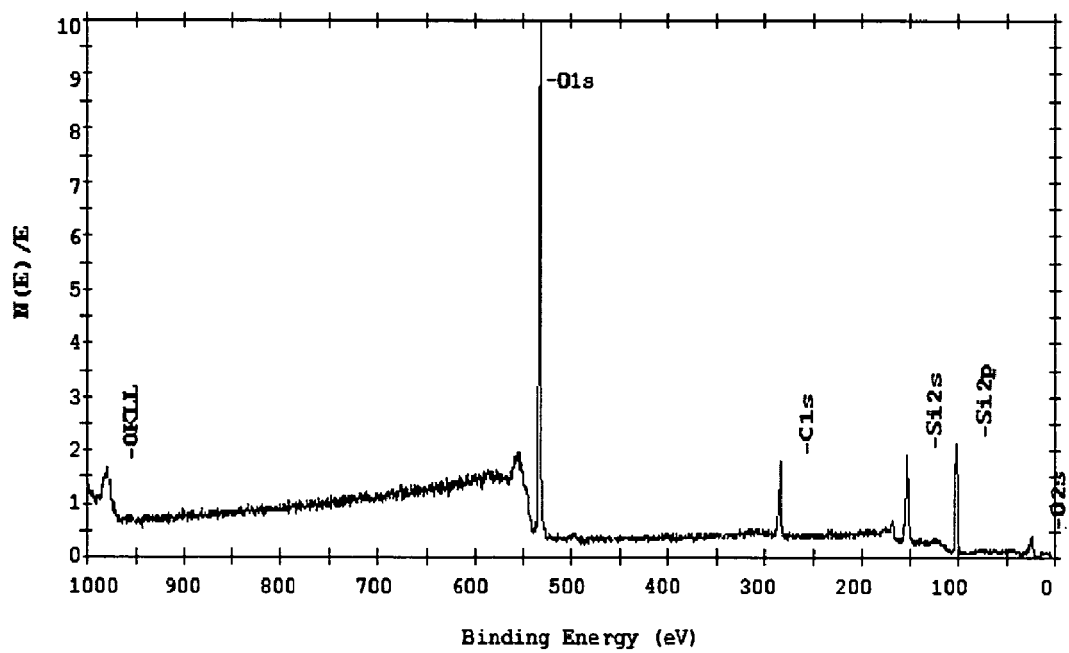
Figure 37:
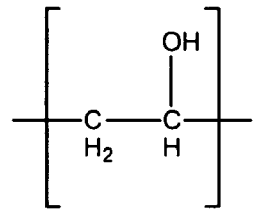
FIG. 37 shows features of a PVA-tethered phthalimide SAM.
Figure 38:
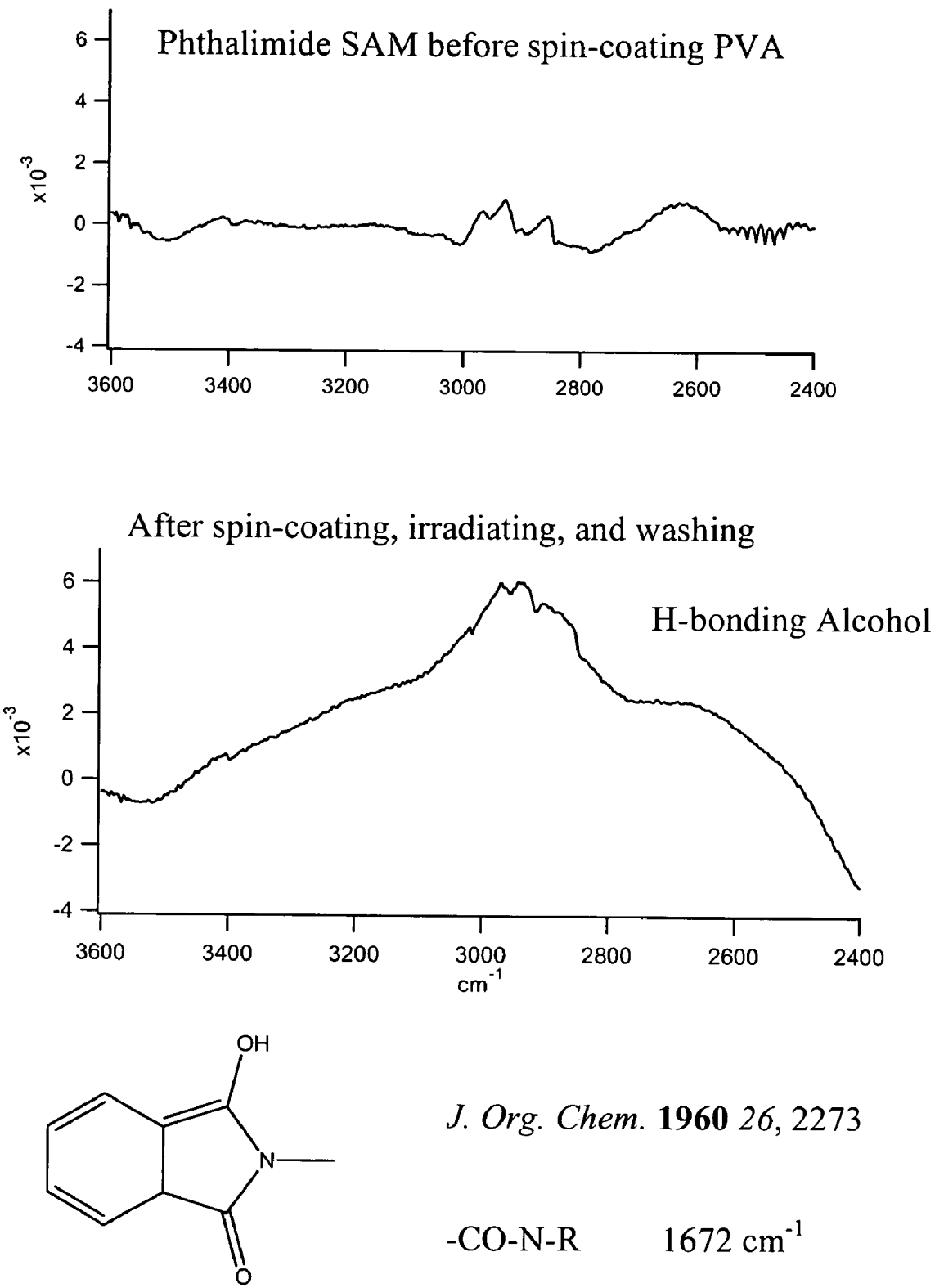
FIG. 38 shows the infrared spectrometry of a PVA-grafted phthalimide SAM.

For example, a solution of poly(epichlorohydrin) (PECH) can be coated onto a benzophenone SAM. Various features of a PECH tethered benzophenone SAM are set forth in FIGS. 36A through 36C. Polymers including poly(vinylalcohol) (PVA) or poly(styrene) can be coated onto a phthalimide SAM. Features of a PVA tethered phthalimide SAM and a PVA grafted phthalimide SAM are set forth in FIG. 37 and FIG. 38, respectively. Various features of a PS tethered phthalimide SAM are demonstrated in FIG. 39. For comparison, benzophenone SAM has a radius of gyration of 2 and a thickness of 1.5 nm. (*J. Am. Chem. Soc.*, 1999, 121, 8766).

For both hydrophilic and hydrophobic polymers, irradiated phthalimide and benzophenone SAMs retain a thicker layer of polymer after rinse than do their non-irradiated counterparts. Contact angles of the surfaces formed change according to the polymer coated on the SAM surface. In some cases, PS is more difficult to remove following irradiation, which is likely due to cross-linking that occurs upon radiation at 254 nm. The film thickness can be correlated to the molecular weight of the starting polymer.

Figure 40A:
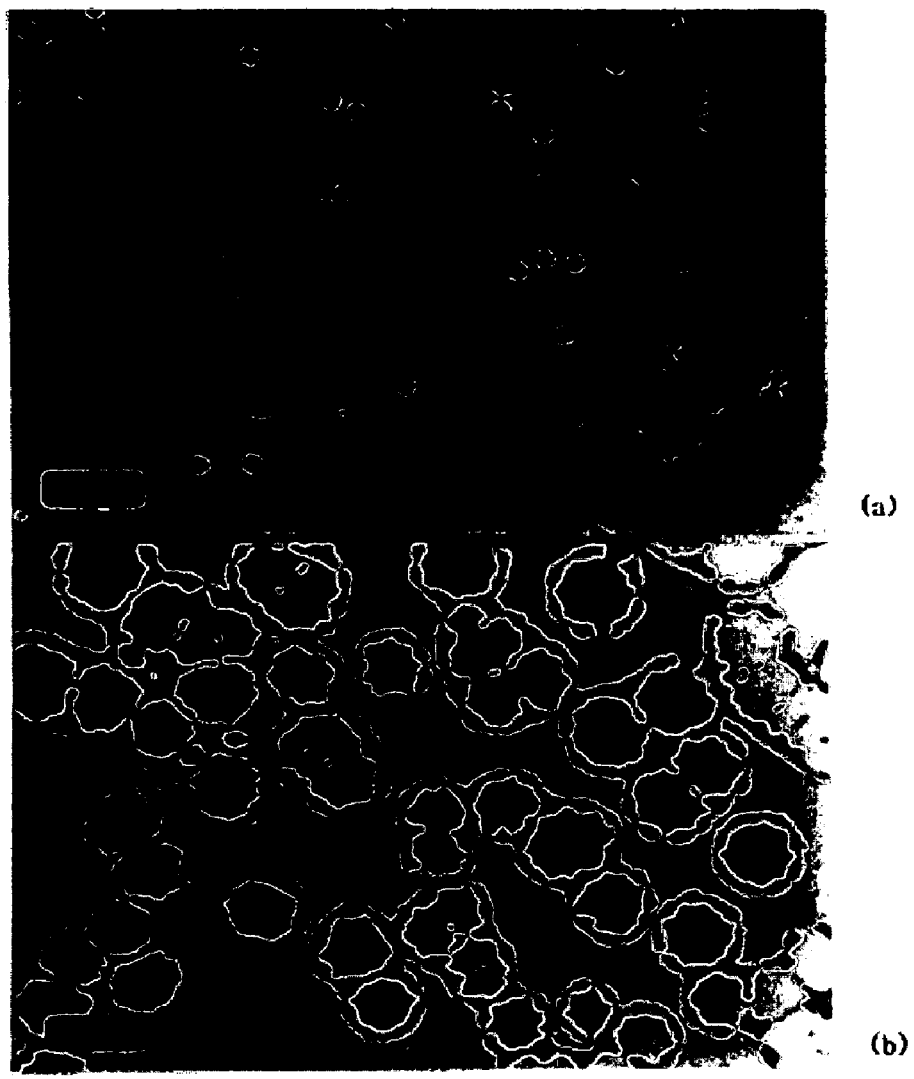
FIG. 40A and FIG. 40B demonstrate the results of dewetting thin films under various conditions.
Figure 40B:
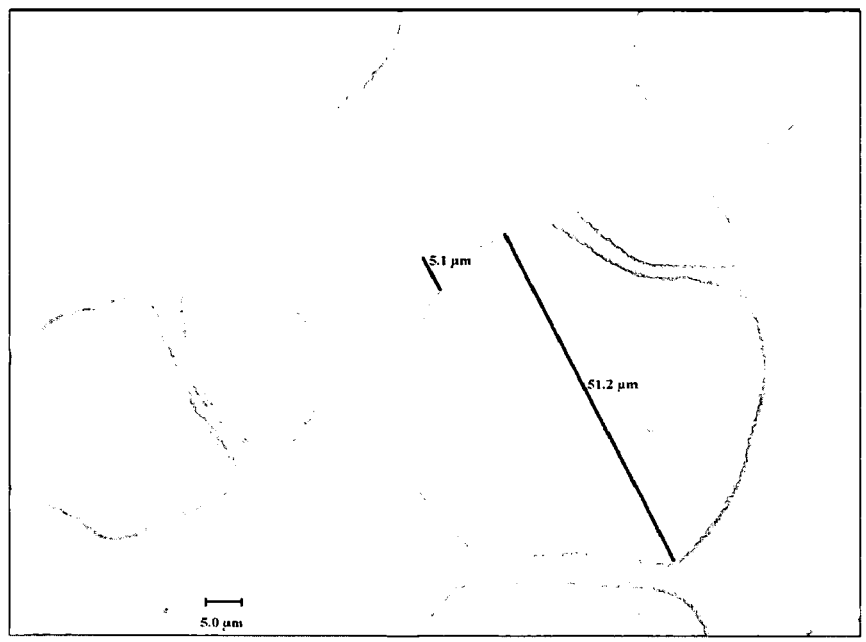
Figure 40B:
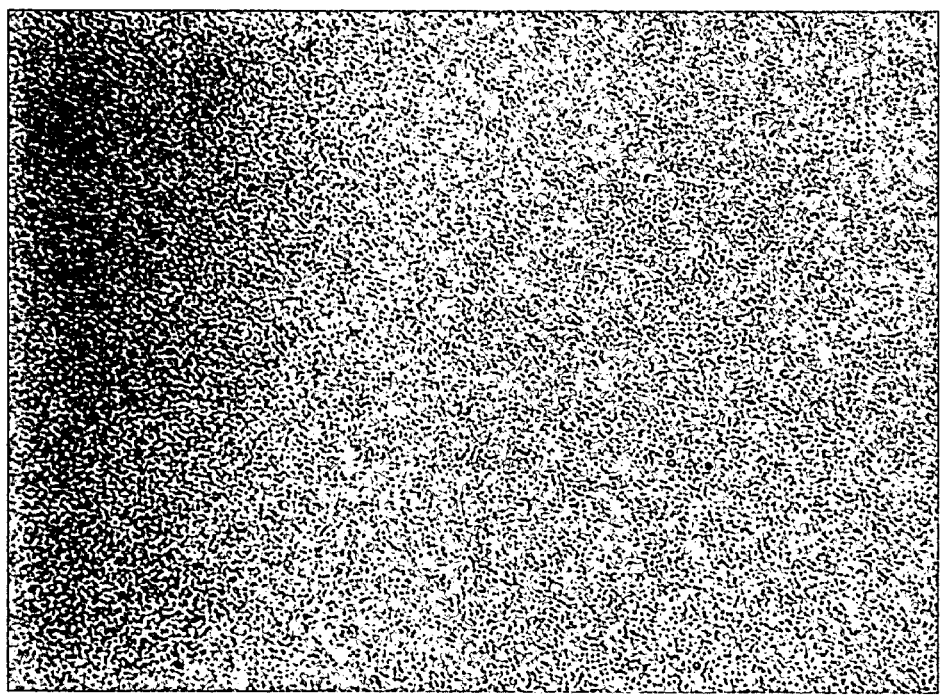
Figure 41A:
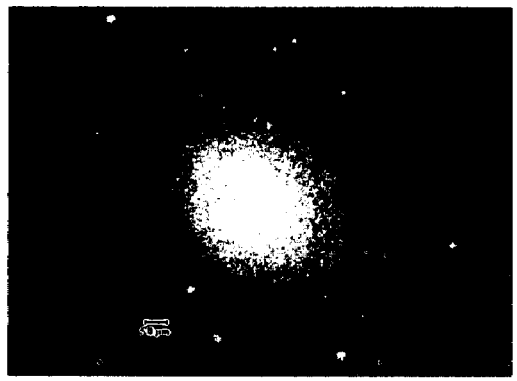
FIG. 41A and FIG. 41B show the results of dewetting tests on PS polymer film on either a phthalimide or benzophenone SAM.
Figure 41A:
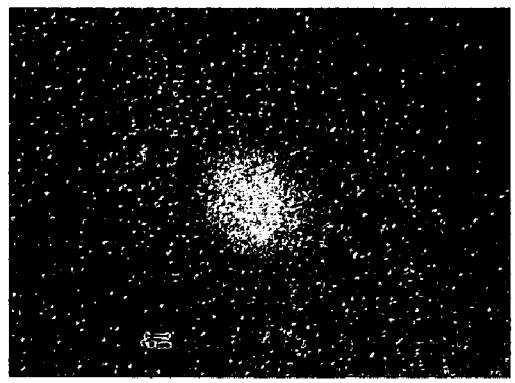
Figure 41A:
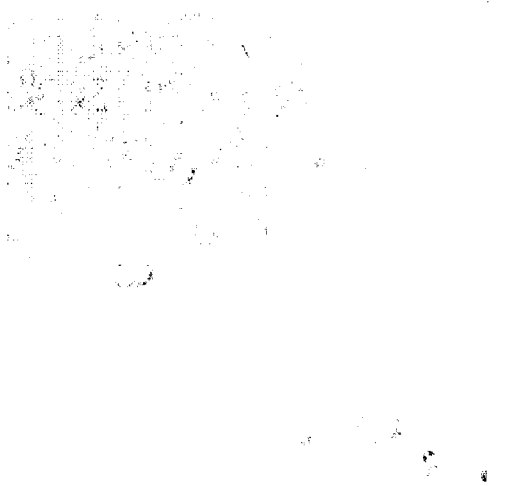
Figure 41A:
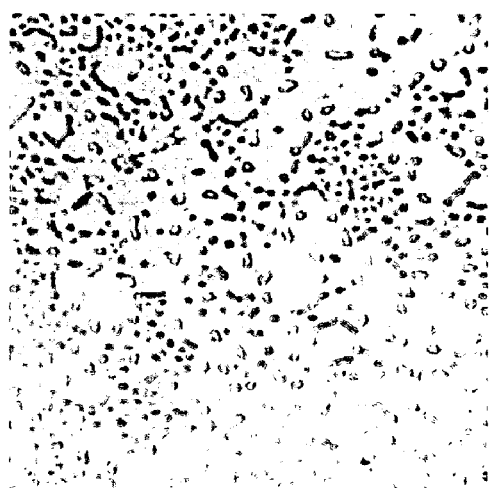
Figure 41B:
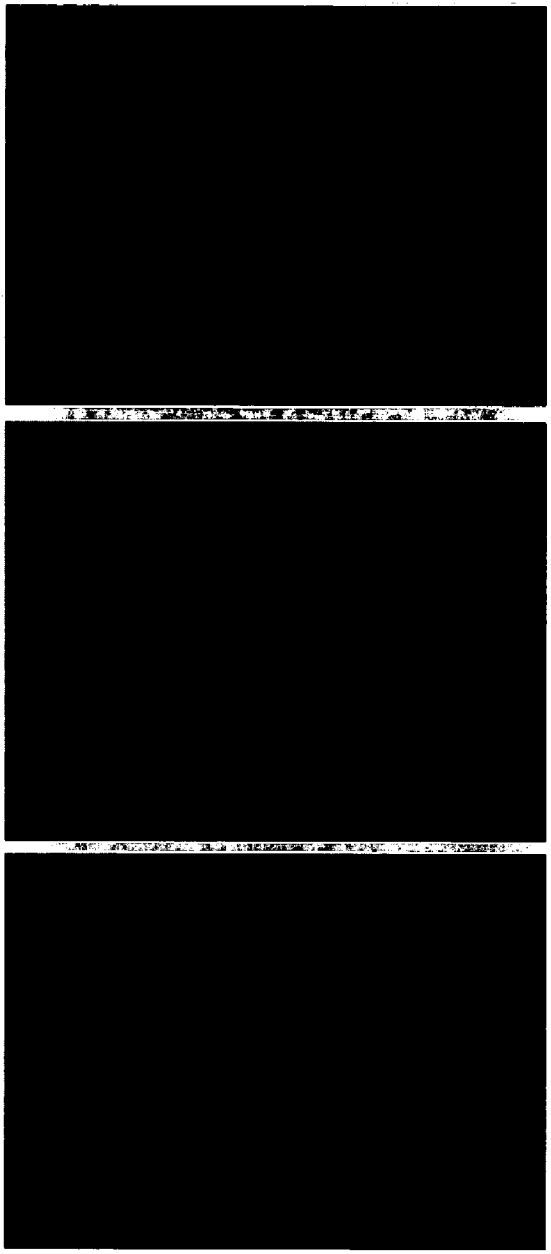
Figure 42A:
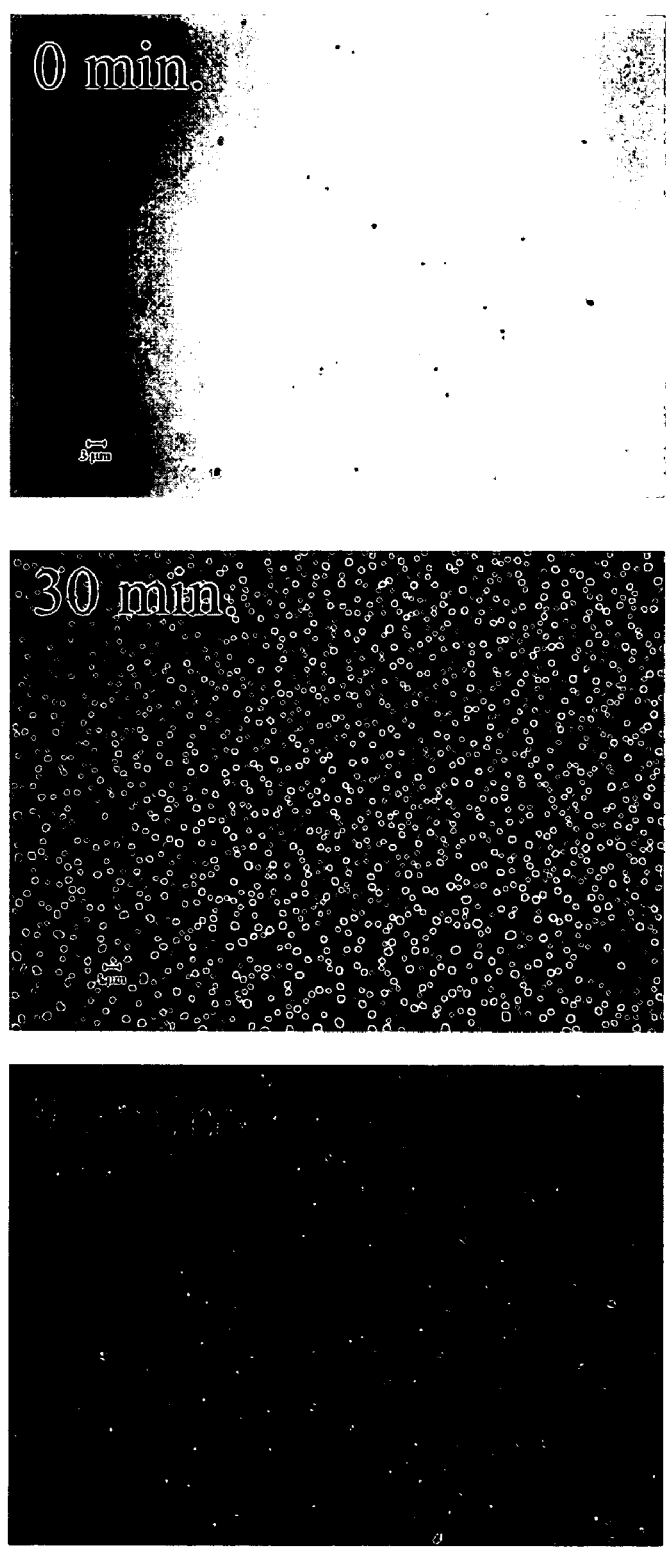
FIG. 42A through FIG. 43B show the results of a competition study comparing the time dependent dewetting data for PS coated on various surfaces.
Figure 42B:
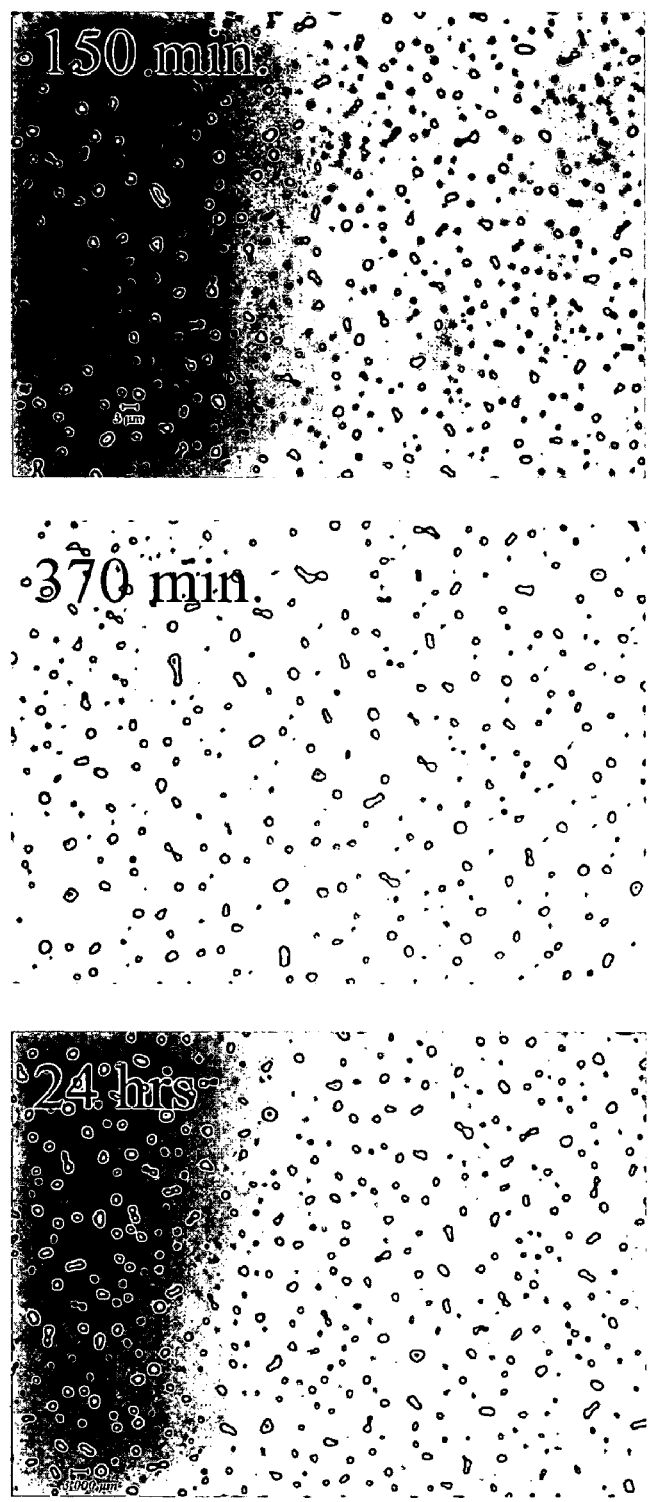
Figure 43A:
Figure 43A:
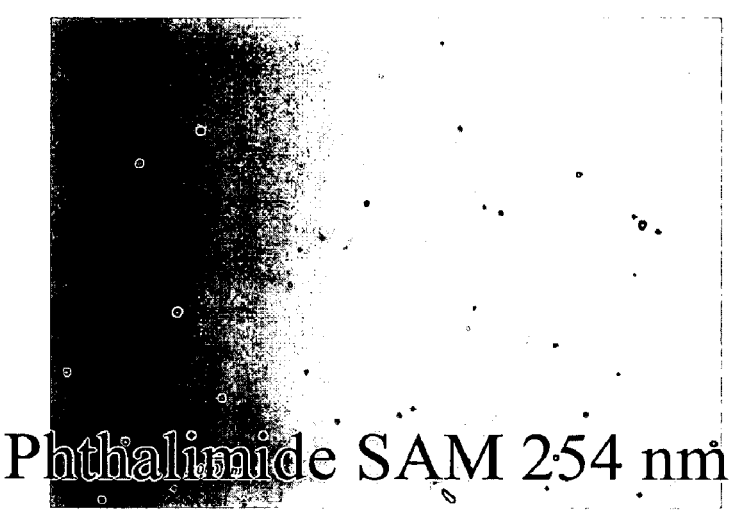
Figure 43A:
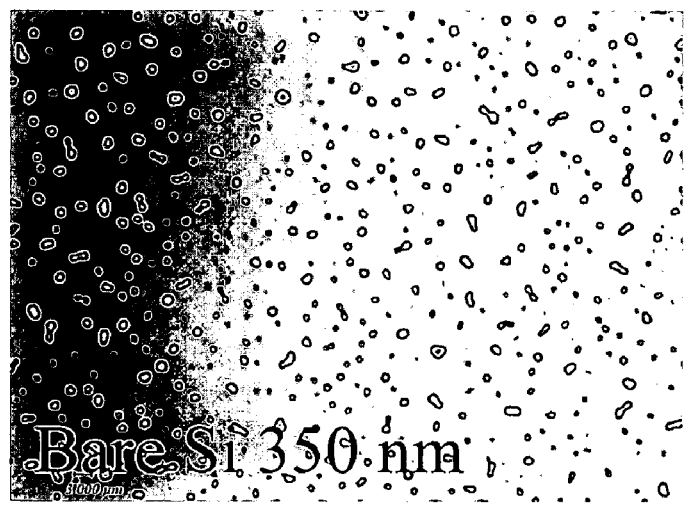
Figure 43B:
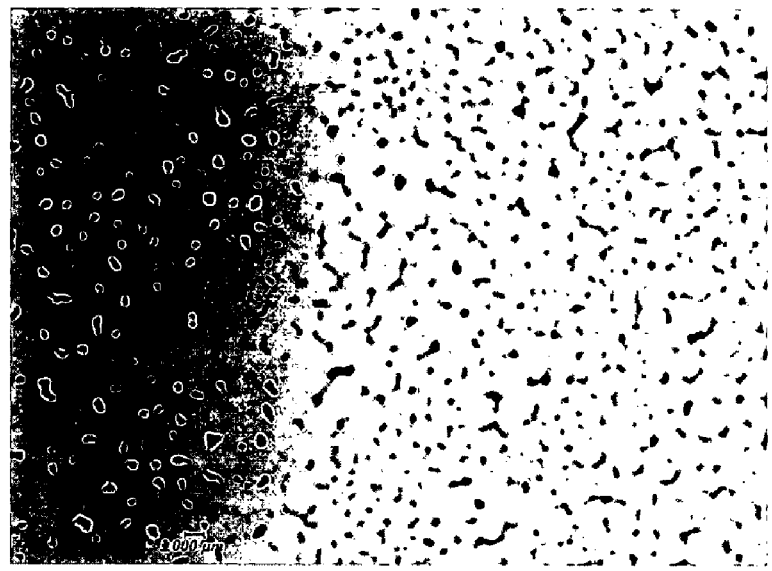
Figure 43B:
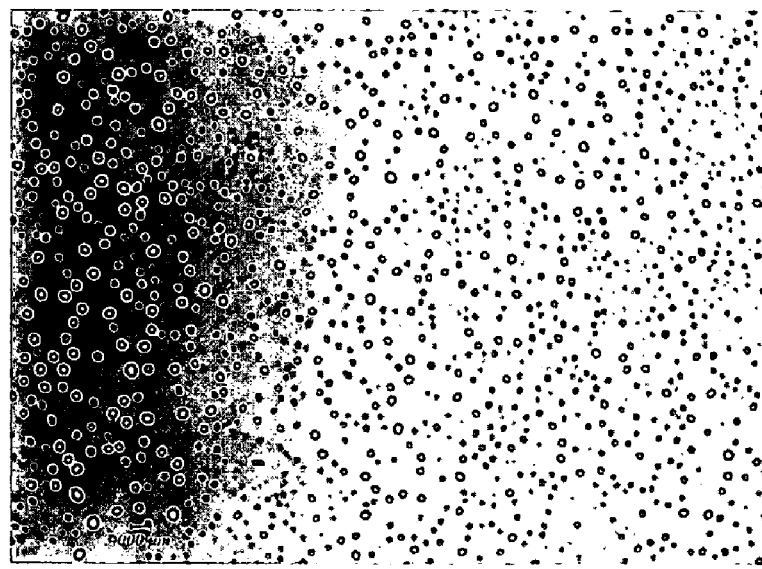

Thin films can be dewetted as shown in FIGS. 40A and 40B. This can be accomplished by heating above the glass transition temperature of the polymer, which results in the formation of holes, followed by the formation of droplets, and can also result in spinodal decomposition of the polymer. (see also *Phys. Rev. Lett.* 1992, 68, 75). FIGS. 41A and 41B show the results of dewetting tests on PS polymer film on either a phthalimide or benzophenone SAM. FIGS. 42A through 43B show the results of a competition study comparing the time dependent dewetting data for phthalimide SAM, benzophenone SAM, and underivatized silicon wafers. FIGS. 42A and 42B show bare silicon wafer followed by exposure for the indicated times. FIGS. 43A and 43B show PS films after 24 hours of exposure, as compared to bare silicon wafers at the indicated wavelengths. In each case, the polymer is PS of MW 30K, the substrate is silicon wafer, the film thickness is 11 nm. Phthalimide SAM can slow down de-wetting, and in some cases can completely prevent dewetting.

These experiments show that photochemical techniques such as exposure to irradiation at 254 nm can stabilize thin polymer film, regardless of the SAM used. The molecular weight of the polymer may also play a role in this stabilization. Benzophenone SAM can slow down droplet formation in dewetting experiments, or at a minimum can produce a change in droplet shape formed.

Figure 44:
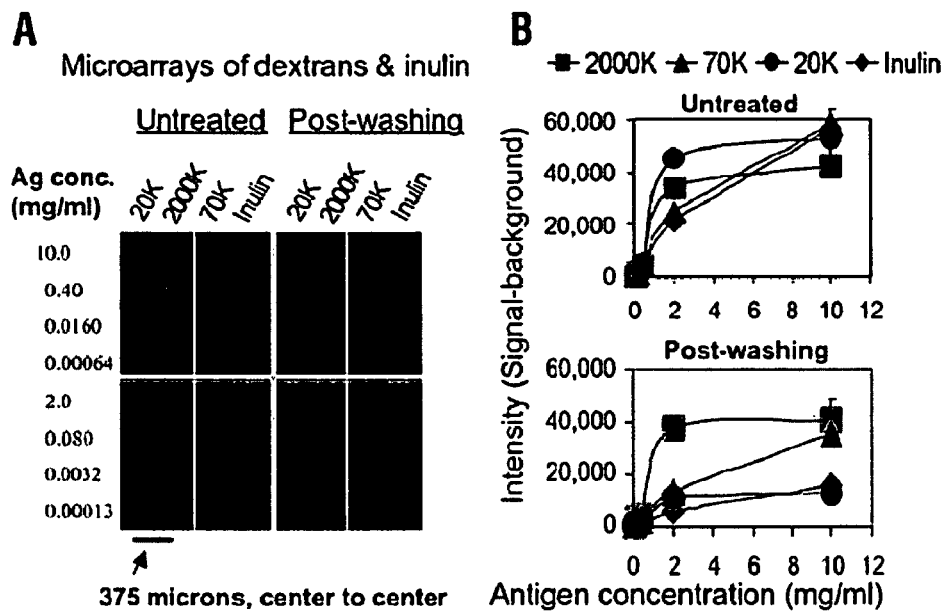
FIG. 44 shows exemplary carbohydrate microarrays.
Figure 44:
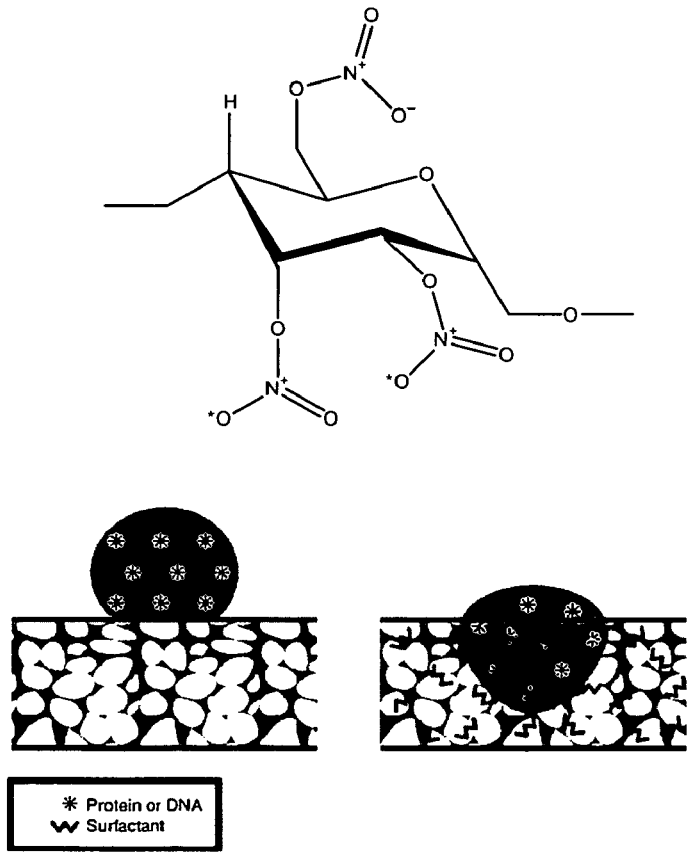

The present invention is also applicable to carbohydrate microarrays. Exemplary carbohydrate microarrays are presented in FIG. 44. (D. Wang, *Nature Biotechnology*, 2002 20, 275).

Figure 45A:
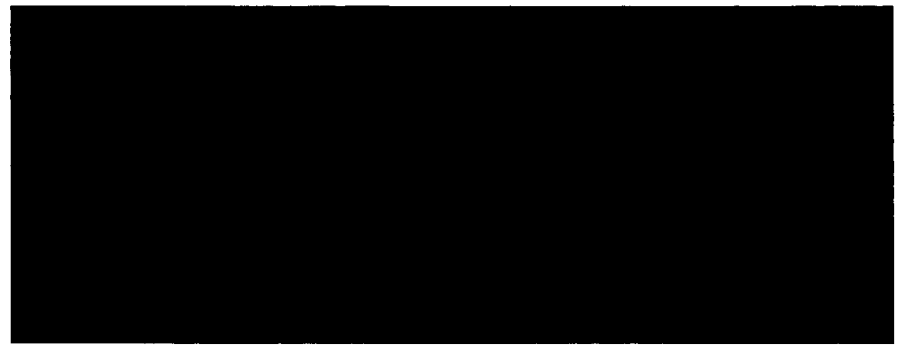
FIG. 45A through FIG. 45C demonstrate the increased hydrophilicity of various surfaces.
Figure 45A:
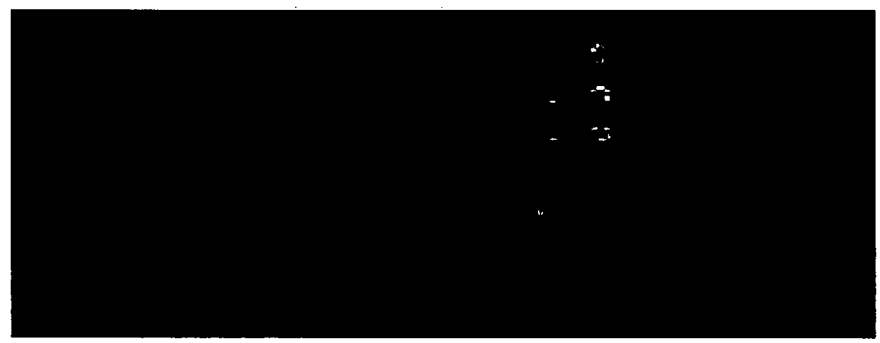
Figure 45A:
Figure 45B:
Figure 45B:
Figure 45B:
Figure 45C:
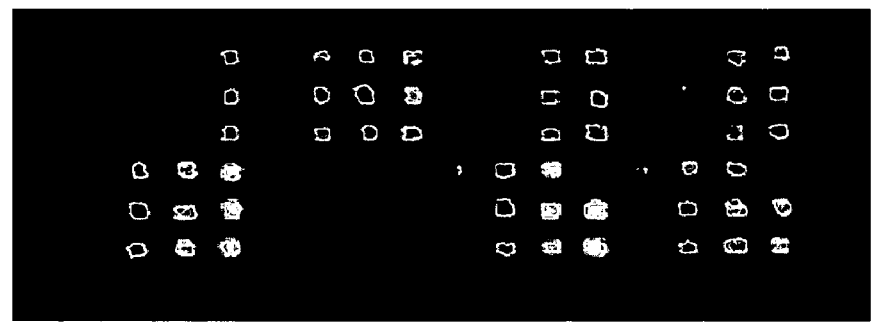
Figure 45C:
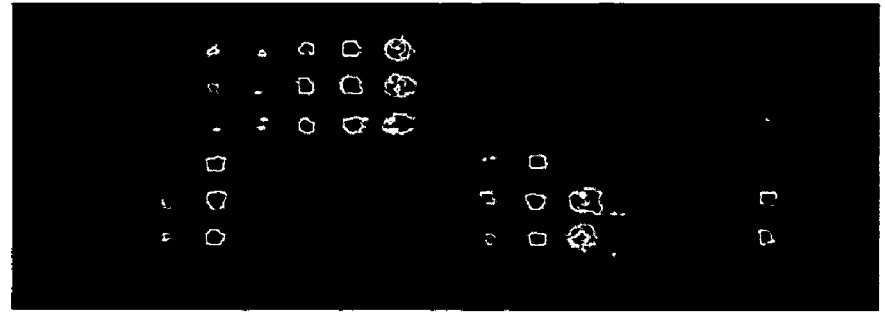

The hydrophilicity of a surface is a function of surface composition, e.g., benzophenone SAM as compared to nitrocellulose, and can also be affected by treatment with light and/or by washing, as shown in FIGS. 45A through 45C.

Figure 46:
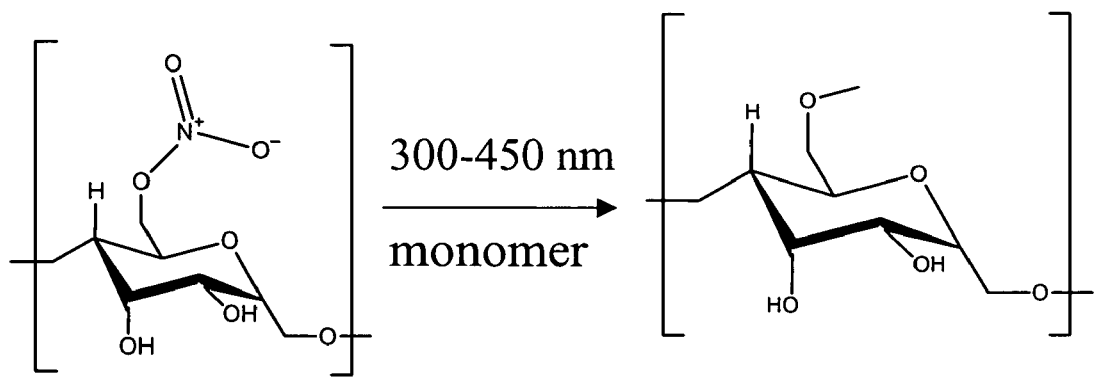
FIG. 46 shows a mechanism for modifying nitrocellulose.
Figure 46:
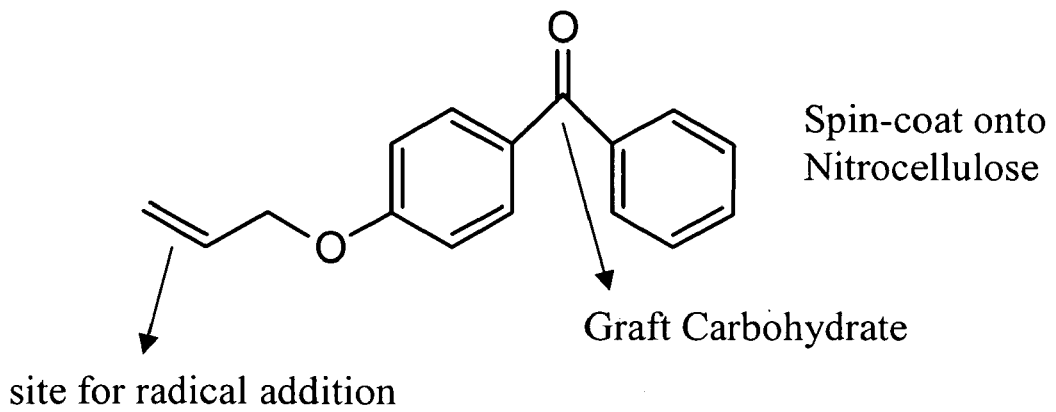
Figure 47A:
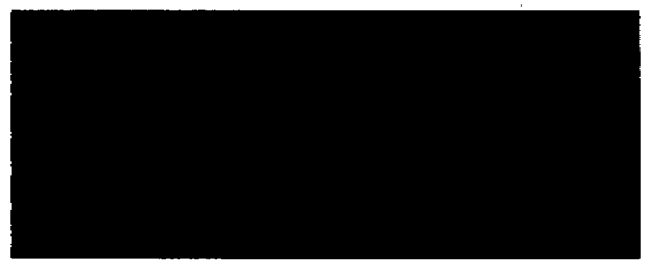
FIG. 47A and FIG. 47B show features of nitrocellulose and nitrocellulose-benzophenone surfaces.
Figure 47A:
Figure 47A:
Figure 47B:
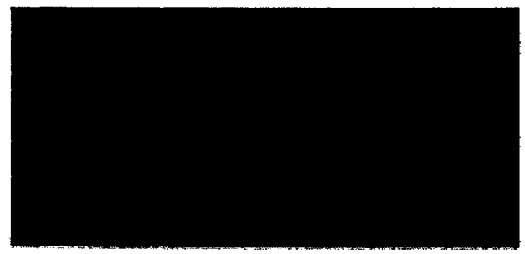
Figure 47B:
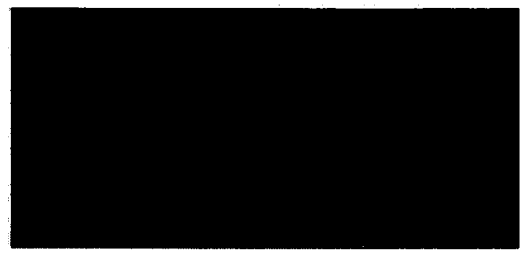
Figure 47B:
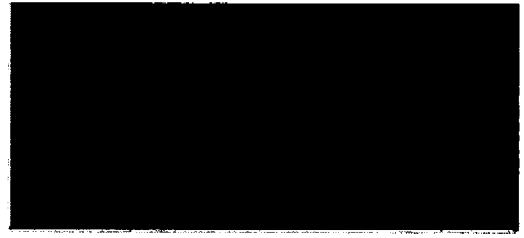

Nitrocellulose surfaces can be modified, for example by exposure to light at 300-450 nm, as in FIG. 46. In one embodiment of the invention, benzophenone monomer can be coated onto a nitrocellulose surface to provide a site for additional modification, including grafting carbohydrates, which is also shown in FIG. 46. Features of exemplary surfaces containing nitrocellulose and benzophenone-nitrocellulose blends are shown in FIGS. 47A and 47B. These surfaces can then exposed to carbohydrates to modify the benzophenone moieties at the carbonyl carbon. In some experiments, however, cross-linking between the benzophenone moiety and the nitrocellulose moiety occurred, which may have prevented attachment of additional carbohydrates.

Figure 48:
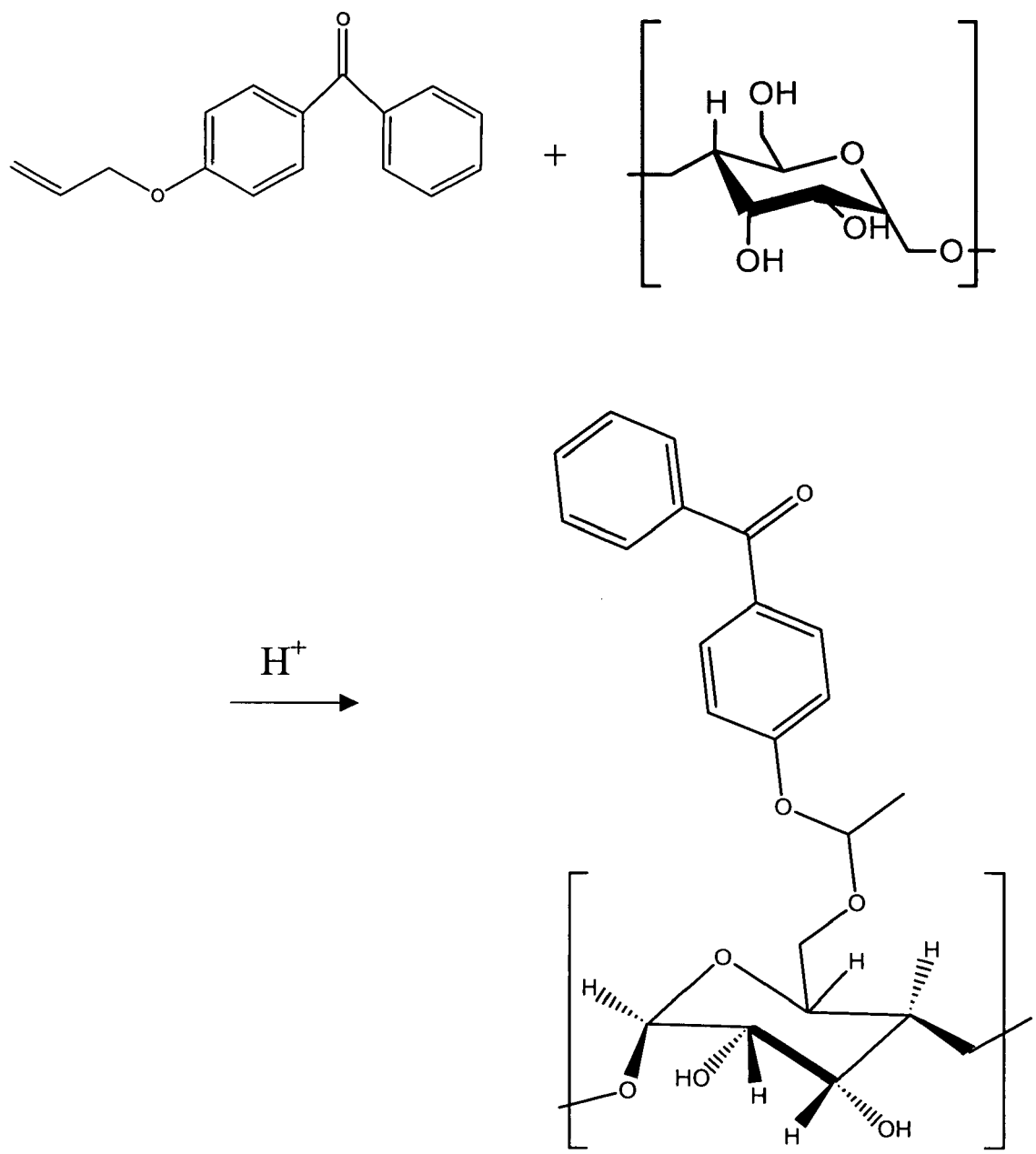
FIG. 48 demonstrates the benzophenone modification of a carbohydrate.

In another example, benzophenone monomer can be coated onto a carbohydrate surface in the presence of acid, as in FIG. 48. These surfaces can then be exposed to carbohydrates to modify the benzophenone moieties at the carbonyl carbon.

Figure 49:
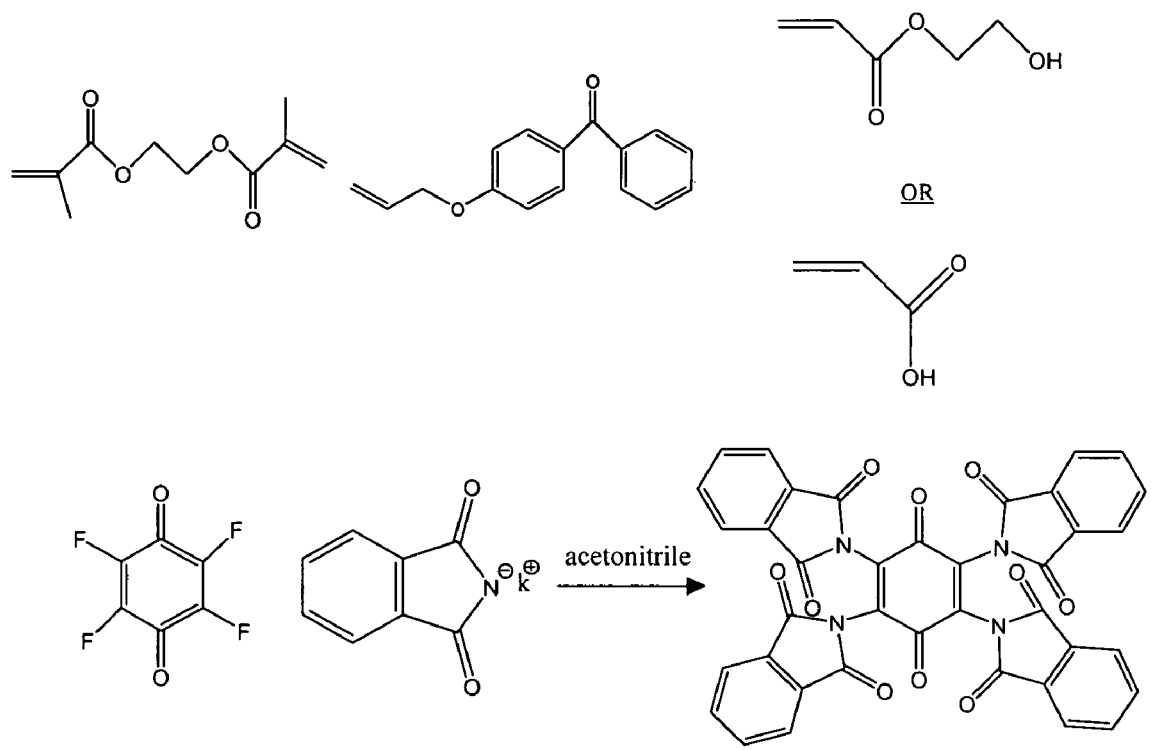
FIG. 49 shows compounds applicable to the SAM and surface modification techniques of the present invention.

FIG. 49 shows compounds that are applicable to the SAM and surface modification techniques of the present invention.

While the invention has been described in detail with reference to certain embodiments thereof, it will be understood that the invention is not limited to these embodiments. Indeed, modifications and variations are within the spirit and scope of that which described and claimed.

What is claimed is:

1. A method for modifying a surface of a monolayer, comprising:
   a) coating a monolayer on a substrate; wherein the monolayer is formed by self-assembly of end-functionalized surfactant molecules, thereby positioning a photoactive functional group at the air-monolayer interface; and
   b) exposing the monolayer to radiation, thereby modifying the surface of the monolayer, wherein the monolayer is a self-assembled monolayer of organic groups comprising a benzophenone moiety, a phthalimide moiety, a benzoin moiety, a photogenerated aldehyde moiety, or a combination thereof, wherein each organic group contains a first functionality that is not converted to a second functionality upon exposure to acid.

2. The method of claim 1, further comprising photodeprotection of the photoactive functional group.

3. The method of claim 1, wherein the self-assembled monolayer surface comprises a coating on a substrate surface.

4. The method of claim 3, wherein the substrate surface comprises glass, metal, metalloid, ceramic, or a combination thereof.

5. The method of claim 3, wherein the substrate surface comprises silicon, gold, or a combination thereof.

6. The method of claim 1, wherein the radiation comprises ultraviolet radiation.

7. The method of claim 1, wherein the radiation comprises deep ultraviolet radiation.

8. The method of claim 1, further comprising coating on the monolayer a macromolecular surfactant.

9. The method of claim 8, wherein the macromolecular surfactant is a polymer.

10. The method of claim 8, wherein the macromolecular surfactant is a hydrophilic polymer.

11. The method of claim 8, wherein the macromolecular surfactant is a hydrophobic polymer.

12. The method of claim 8, further comprising immobilizing on the monolayer a compound selected from the group consisting of a carbohydrate, a peptide, a protein, DNA, an enzyme, an aptamer, a colloidal particle, a nanoparticle, a metal oxide, or a combination thereof.

13. The method of claim 12, wherein the immobilized compound comprises a carbohydrate.

14. The method of claim 1, wherein the self-assembled monolayer comprises a phthalimide moiety.

15. The method of claim 1, wherein the substrate surface comprises glass.

* * * * *